(12) United States Patent
Zhang et al.

(10) Patent No.: US 8,748,352 B2
(45) Date of Patent: Jun. 10, 2014

(54) PEPTIDE AND PROTEIN BIOMARKERS FOR TYPE 1 DIABETES MELLITUS

(75) Inventors: Qibin Zhang, West Richland, WA (US); Thomas O. Metz, Kennewick, WA (US)

(73) Assignee: Battelle Memorial Institute, Richland, WA (US)

(*) Notice: Subject to any disclaimer, the term of this patent is extended or adjusted under 35 U.S.C. 154(b) by 0 days.

(21) Appl. No.: 13/586,321

(22) Filed: Aug. 15, 2012

(65) Prior Publication Data

US 2013/0045887 A1 Feb. 21, 2013

Related U.S. Application Data

(60) Provisional application No. 61/524,173, filed on Aug. 16, 2011.

(51) Int. Cl.
| | | |
|---|---|---|
| G01N 27/62 | (2006.01) | |
| G01N 33/573 | (2006.01) | |
| C07K 7/06 | (2006.01) | |
| C40B 40/10 | (2006.01) | |

(52) U.S. Cl.
USPC ............ 506/7; 435/23; 435/7.4; 435/6.4

(58) Field of Classification Search
CPC .............. G01N 2800/60; C07K 14/4713
USPC ................................. 506/7; 435/6.4
See application file for complete search history.

(56) References Cited

U.S. PATENT DOCUMENTS

| | | | |
|---|---|---|---|
| 2009/0117578 A1 | 5/2009 | Metz et al. | |
| 2012/0077209 A1* | 3/2012 | Chance et al. | 435/7.4 |
| 2012/0149022 A1* | 6/2012 | Aw | 435/6.12 |
| 2012/0208218 A1* | 8/2012 | Nagalla et al. | 435/7.94 |

FOREIGN PATENT DOCUMENTS

WO WO 2009/140390 A2 11/2009

OTHER PUBLICATIONS

Van der Heul Nieuwenhieijsen et al.,Journal Clinical Endocrinology and Metabolism, Apr. 2010, 95 (4), pp. 1962-1971.*
Doherty et al,Proteomics Clinical Applications, 2008, 2, pp. 135-141.*
Chatzigeorgiou et al.,In Vivo, 23, 2009, pp. 245-258.*
Hoenig,M.,Molecular and Cellular Endocrinology,197, 2002, pp. 221-229.*
Bonora et al, Diabetes Care, vol. 34, Supplement 2, May 2011, p. S184-S190.*
Anderson & Hunter, "Quantitative Mass Spectrometric Multiple Reaction Monitoring Assays for Major Plasma Proteins," *Mol. Cell Proteomics* 5:573-588 (2006).
Barker, et al., "Prediction of Autoantibody Positivity and Progression to Type 1 Diabetes: Diabetes Autoimmunity Study in the Young (DAISY)," *J. Clin. Endocrinol. Metab.*89:3896-3902 (2004).

(Continued)

*Primary Examiner* — Larry Riggs
*Assistant Examiner* — Karla Dines
(74) *Attorney, Agent, or Firm* — Klarquist Sparkman, LLP

(57) ABSTRACT

A method for identifying persons with increased risk of developing type 1 diabetes mellitus, or having type I diabetes mellitus, utilizing selected biomarkers described herein either alone or in combination. The present disclosure allows for broad based, reliable, screening of large population bases. Also provided are arrays and kits that can be used to perform such methods.

11 Claims, 15 Drawing Sheets
(15 of 15 Drawing Sheet(s) Filed in Color)

(56) References Cited

OTHER PUBLICATIONS

Bingley et al., "Diabetes Antibody Standardization Program: First Assay Proficiency Evaluation," *Diabetes* 52:1128-1136 (2003).
Bingley et al., "Measurement of Islet Cell Antibodies in the Type 1 Diabetes Genetics Consortium: Efforts to Harmonize Procedures Among the Laboratories," *Clin. Trials* 7:S56-S64 (2010).
Bucki et al., "Plasma Gelsolin: Function, Prognostic Value, and Potential Therapeutic Use," *Curr. Protein Pept. Sci.* 9:541-551 (2008).
Callister et al., "Normalization Approaches for Removing Systematic Biases Associated with Mass Spectrometry and Label-Free Proteomics," *J. Proteome. Res.* 5:277-286 (2006).
Davis et al., "Biological Activities of C1 Inhibitor," *Mol. Immunol.* 45:4057-4063 (2008).
D'Hertog et al., "Type 1 Diabetes: Entering the Proteomic Era," *Expert Rev. Proteomics* 3:223-236 (2006).
Dziarski & Gupta, "The Peptidoglycan Recognition Proteins (PGRPs)," *Genome Biol.* 7:232 (2006).
Gonzalez et al., "Development of a Fibrinogen-Specific Sandwich Enzyme-Linked Immunosorbent Assay Microarray Assay for Distinguishing Between Blood Plasma and Serum Samples," *Anal Biochem* 414:99-102 (2011).
Hagopian et al., "The Environmental Determinants of Diabetes in the Young (TEDDY): Genetic Criteria and International Diabetes Risk Screening of 421,000 Infants," *Pediatr. Diabetes* 12:733-743 (2011).
Hoijer et al., "Inflammatory Properties of Peptidoglycan are Decreased After Degradation by Human N-acetylmuramyl-L-alanine Amidase," *Eur. Cytokine Netw.* 8:375-381 (1997).
Horn et al., "Allelic Sequence Variation of the HLA-DQ loci: Relationship to Serology and to Insulin-Dependent Diabetes Susceptibility," *Proc. Natl. Acad. Sci. USA* 85:6012-6016 (1988).
Hortin et al., "High-Abundance Polypeptides of the Human Plasma Proteome Comprising the Top 4 Logs of Polypeptide Abundance," *Clin. Chem.* 54:1608-1616 (2008).
Jaitly et al. "Decon2LS: An Open-Source Software Package for Automated Processing and Visualization of High Resolution Mass Spectrometry Data," *BMC Bioinformatics* 10:87 (2009).
Knip et al., "Environmental Triggers and Determinants of Type 1 Diabetes," *Diabetes* 54:S125-S136 (2005).
Krijgsveld et al., "Thrombocidins, Microbicidal Proteins From Human Blood Platelets, are C-terminal Deletion Products of CXC Chemokines," *J. Biol. Chem.* 275:20374-20381 (2000).
Kuzyk et al., "Multiple Reaction Monitoring-Based, Multiplexed, Absolute Quantitation of 45 Proteins in Human Plasma," *Mol. Cell Proteomics* 8:1860-1877 (2009).
Lathem et al., "Potentiation of C1 Esterase Inhibitor by StcE, a Metalloprotease Secreted by *Escherichia coli* O157:H7," *J. Exp. Med.* 199:1077-1087 (2004).
Livesay et al., "Fully Automated Four-Column Capillary LC-MS System for Maximizing Throughput in Proteomic Analyses," *Anal. Chem.* 80:294-302 (2008).

Maclean et al., "Effect of Collision Energy Optimization on the Measurement of Peptides by Selected Reaction Monitoring (SRM) Mass Spectrometry," *Anal. Chem.* 82:10116-10124 (2010).
Metz et al., "Application of Proteomics in the Discovery of Candidate Protein Biomarkers in a Diabetes Autoantibody Standardization Program Sample Subset," *J. Proteome Res* 7:698-707 (2008).
Monroe et al., "VIPER: An Advanced Software Package to Support High-Throughput LC-MS Peptide Identification," *Bioinformatics* 23:2021-2023 (2007).
Nesvizhskii & Aebersold, "Interpretation of Shotgun Proteomic Data: the Protein Inference Problem," *Mol. Cell Proteomics* 4:1419-1440 (2005).
Petritis et al., "Improved Peptide Elution Time Prediction for Reversed-Phase Liquid Chromatography-MS by Incorporating Peptide Sequence Information," *Anal. Chem.* 78:5026-5039 (2006).
Pietropaolo et al., "Primer: Immunity and Autoimmunity," *Diabetes* 57:2872-2882 (2008).
Qian et al., "Enhanced Detection of Low Abundance Human Plasma Proteins Using a Tandem IgY12-SuperMix Immunoaffinity Separation Strategy," *Mol. Cell. Proteomics* 7:1963-1973 (2008).
Refai et al., "Transthyretin Constitutes a Functional Component in Pancreatic β-cell Stimulus-Secretion Coupling," *Proc. Natl. Acad. Sci. USA* 102:17020-17025 (2005).
Schiess et al., "Targeted Proteomic Strategy for Clinical Biomarker Discovery," *Mol. Oncol.* 3:33-44 (2009).
Schlosser et al., "Diabetes Antibody Standardization Program: Evaluation of Assays for Insulin Autoantibodies," *Diabetologia* 53:2611-2620 (2010).
Schutzer et al., "Distinct Cerebrospinal Fluid Proteomes Differentiate Post-Treatment Lyme Disease from Chronic Fatigue Syndrome," *PLoS One* 6:e17287 (2011).
Stene et al., "Enterovirus Infection and Progression from Islet Autoimmunity to Type 1 Diabetes: the Diabetes and Autoimmunity Study in the Young (DAISY)," *Diabetes* 59:3174-3180 (2010).
Tisch & McDevitt, "Insulin-Dependent *Diabetes mellitus*," *Cell* 85:291-297 (1996).
Torn et al., "Diabetes Antibody Standardization Program: Evaluation of Assays for Autoantibodies to Glutamic Acid Decarboxylase and Islet Antigen-2," *Diabetologia* 51:846-852 (2008).
Walz & Baggiolini, "Generation of the Neutrophil-Activating Peptide NAP-2 from Platelet Basic Protein or Connective Tissue-Activating Peptide III Through Monocyte Proteases," *J. Exp. Med.* 171:449-454 (1990).
Wenzlau et al., The Cation Efflux Transporter ZnT8 (S1c30A8) is a Major Autoantigen in Human Type 1 Diabetes, *Proc. Natl. Acad. Sci. USA* 104:17040-17045 (2007).
Zhang, "Prediction of Low-Energy Collision-Induced Dissociation Spectra of Peptides," *Anal. Chem.* 76:3908-3922 (2004).
Zimmer et al., "Advances in Proteomics Data Analysis and Display Using an Accurate Mass and Time Tag Approach," *Mass Spectrom. Rev.* 25:450-482 (2006).

* cited by examiner

Fold Change Analysis

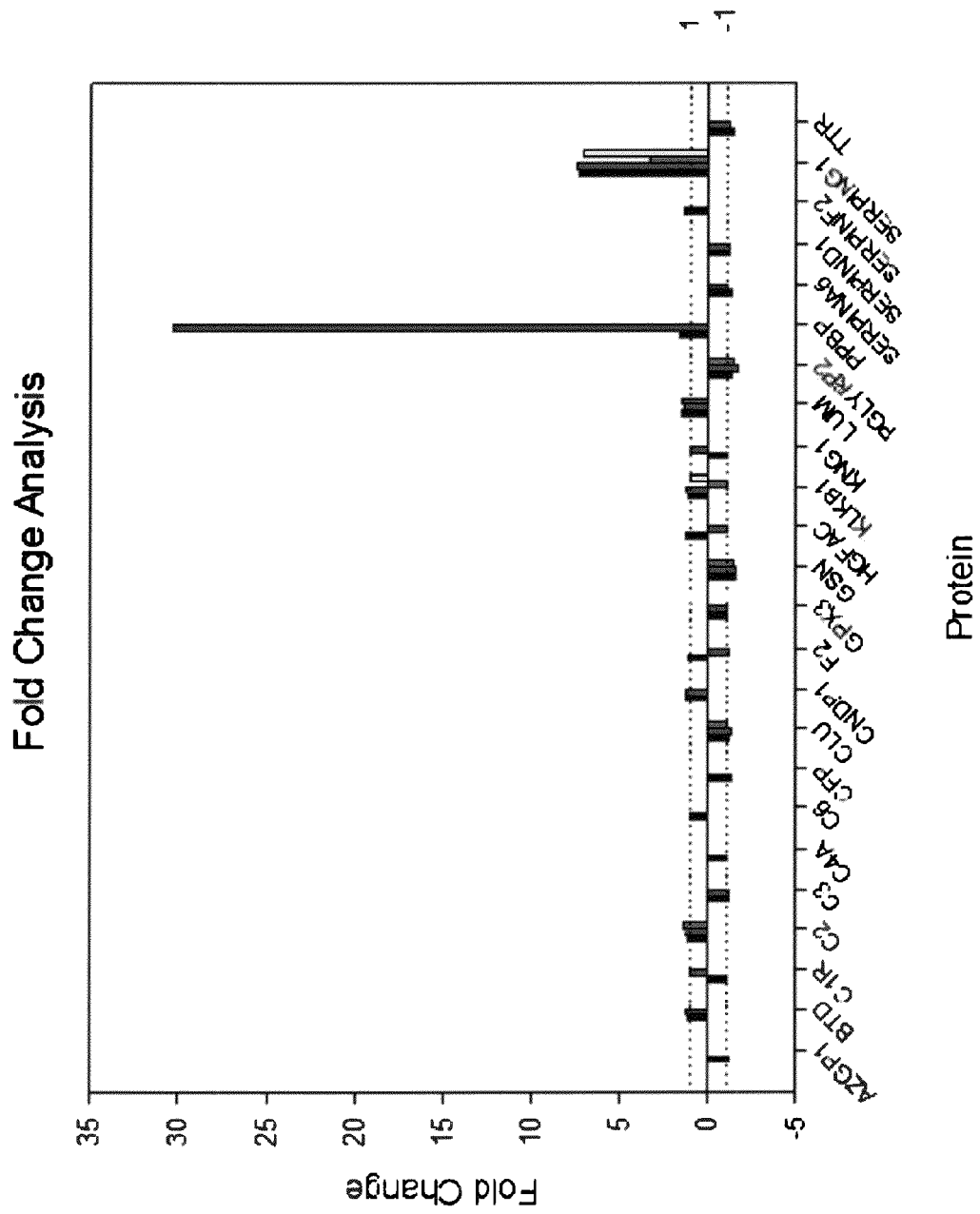

PEPTIDE AND PROTEIN BIOMARKERS FOR TYPE 1 DIABETES MELLITUS

CROSS-REFERENCE TO RELATED APPLICATION

This application claims priority to U.S. Provisional Application No. 61/524,173 filed Aug. 16, 2011, herein incorporated by reference in its entirety.

ACKNOWLEDGMENT OF GOVERNMENT SUPPORT

This invention was made with Government support under Contract DE-AC0576RL01830 awarded by the U.S. Department of Energy. The government has certain rights in the invention.

FIELD

The present disclosure generally relates to methods and systems for the screening and detection of persons having or at risk for developing type 1 diabetes mellitus (T1DM).

BACKGROUND

Type 1 diabetes mellitus (T1DM) is caused primarily by autoimmune destruction of insulin-producing pancreatic beta-cells,[1-3] and in some cases, also by non-immune related severe insulin deficiency.[4] Although the presence of several genotypes on the human leukocyte antigen alleles indicate predisposition to T1DM,[5-8] and increasing evidence points to environmental triggers such as exposure to enterovirus and the composition of early childhood diet,[9-14] the etiology of T1DM remains unknown.

It has been estimated that only 20% of β cell mass remains at the time of presentation of clinical T1D symptoms,[1] which is typically preceded by an asymptomatic period of highly variable duration from a few months to more than 10 years.[15] The appearance of several autoantibodies to specific islet antigens is the first detectable sign of emerging beta-cell autoimmunity.[9] These autoantigens include glutamic acid decarboxylase (GAD), protein tyrosine phosphatase (IA-2), insulin and most recently, the zinc transporter Slc30A8 protein.[4,6,16] Multiple autoantibody positivities and their persistence are unequivocally related to the risk of progression to overt T1DM, both in family studies and also in surveys of general population cohorts.[1,17,20] However, islet autoantibody assays are difficult to perform with consistent high sensitivity and specificity, and performance at different sites varies considerably despite multiple efforts to standardize these assays by the Diabetes Antibody Standardization Program (DASP) and the Type 1 Diabetes Genetics Consortium.[21-23] In addition, not all islet autoantibody-positive subjects progress to T1DM.[17,20,24]

SUMMARY

Type 1 diabetes mellitus (T1DM) results from autoimmune destruction of insulin-producing pancreatic β-cells triggered by complex interactions of environmental factors in genetically predisposed individuals. The autoantibody assays used to predict the progression and confirm clinical diagnoses of T1DM suffer from sometimes poor inter-laboratory reproducibility and predicting power.

The inventors used proteomics technologies to identify novel protein biomarkers of T1DM that can be more accurate and precise than the currently available autoantibody measurements and provide additional insight into the pathogenesis of this disease. Liquid chromatography-mass spectrometry (LC-MS)-based bottom-up proteomics analyses were used to identify blood serum and plasma peptides/proteins significantly changed between type 1 diabetic and control subjects.[25] 24 human serum proteins showed significant changes between T1DM and control subjects.

These biomarkers (52 surrogate peptides representing these 24 proteins) were further verified using targeted, multiplexed multiple reaction monitoring (MRM)-LC-MS assays in a DASP sample cohort, consisting of 100 control and 50 T1DM subjects. This targeted analysis approach, although recently adopted by the proteomics field,[26-30] has been used for decades in quantification of low molecular weight analytes (<1000 Da) in pharmaceutical, clinical and environmental applications. It is shown herein that 14 peptides (see Table 6b) have very good discriminating power, with areas under the curve >0.8 (Receiver operating characteristic analysis) and p values <0.001 (Mann-Whitney U test). Three proteins (cleavage forms of platelet basic protein (PPBP, C1 inhibitor and N-acetylmuramoyl-L-alanine amidase) are important components of the innate immune response. Two peptides, NIQSLEVIGK (SEQ ID NO: 41) from PPBP and LLDSLPSDTR (SEQ ID NO: 48) from C1 inhibitor were up-regulated 8.5-(p=6.62E-18, U test) and 2.1-fold (p=1.39E-4, U test), respectively, in individuals with T1DM. These two peptides achieved both 100% sensitivity and 100% specificity in diagnosis of T1DM in a subsequent independent cohort of DASP samples (10 control and 10 T1DM subjects) blinded to the investigators, and were 30.4-(NIQSLEVIGK; p=1.08E-5, U test) and 7.5-fold (LLDSLPSDTR; p=1.08E-5, U test) up-regulated in patients versus healthy controls in the blinded cohort. The biological significance of these peptides indicate a role for the innate immune response in the pathogenesis of T1DM.

Based on these results, methods of diagnosing or prognosing T1DM in a mammal are provided. In particular examples, the method includes determining or detecting a quantity of at least one protein or peptide listed in Table 6a or 6b in a blood sample from the mammal, and comparing the quantity of the at least one protein or peptide to a control representing expression of the at least one protein or peptide expected in a subject who does not have T1DM (such as a healthy subject or group of subjects). T1DM is diagnosed or prognosed in the mammal when differential expression of the at least one protein or peptide between the blood sample and the control is detected. In particular examples the method has a specificity of at least 95% and a sensitivity of at least 95%, such as a specificity of at least 97% and a sensitivity of at least 97%, a specificity of at least 99% and a sensitivity of at least 99%, or a specificity of at least 100% and a sensitivity of at least 100%. In some examples, the disclosed method (or the peptides or proteins analyzed) has an AUC of at least 0.90, at least 0.95, or at least 1.

Also provided herein are arrays that include a solid support and antibodies specific for at least five of the T1DM-related protein sequences provided herein (such as those proteins or peptides listed in Tables 6a and 6b). Also provided are kits that include such arrays, and other components, such as a buffer solution in separate packaging. In some examples, the disclosed kits include one or more (such as two or more, three or more, or four or more) T1DM-related peptide sequences provided herein (such as the 52 peptides listed in Tables 6a and 6b, or the 14 peptides in Table 2 or the 8 peptides in Table 3) that are stable isotope labeled.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6a-b. Results of all 52 peptide assays performed in the blind cohort (10 control and 10 T1DM subjects) after revealing of clinical status. Relative peptide abundances were used in the data analysis, which were calculated as the ratio between endogenous peptides and their spiked-in SIS analogs. Significance test was performed with non-parametric Mann Whitney U test, and the p values and other statistical analysis results in Table 5. (a) Fold change in abundance of each peptide, calculated by comparing the mean of peptide abundance in the type 1 diabetic state to that in control. Each column represents a unique peptide, and the peptides are grouped by gene name of each protein. The two dashed lines indicate fold changes of 1.0 and −1.0, which represent no change. (b) Box-Whisker plots of each peptide shows the entire range of relative peptide abundances in control and type 1 diabetic groups, with the lower and upper lines of each box representing the $25^{th}$ and $75^{th}$ percentiles, respectively. The black and red horizontal lines within each box represent the median and mean values, respectively. The crossbars extend to the $10^{th}$ and $90^{th}$ percentile values, with outliers beyond this range shown as individual points. For each peptide, the left box plot represents the control group and the right box the patients. The sequences on the x-axis are shown in SEQ ID NOS: 1-52, respectively.

SEQUENCE LISTING

Figure 1:
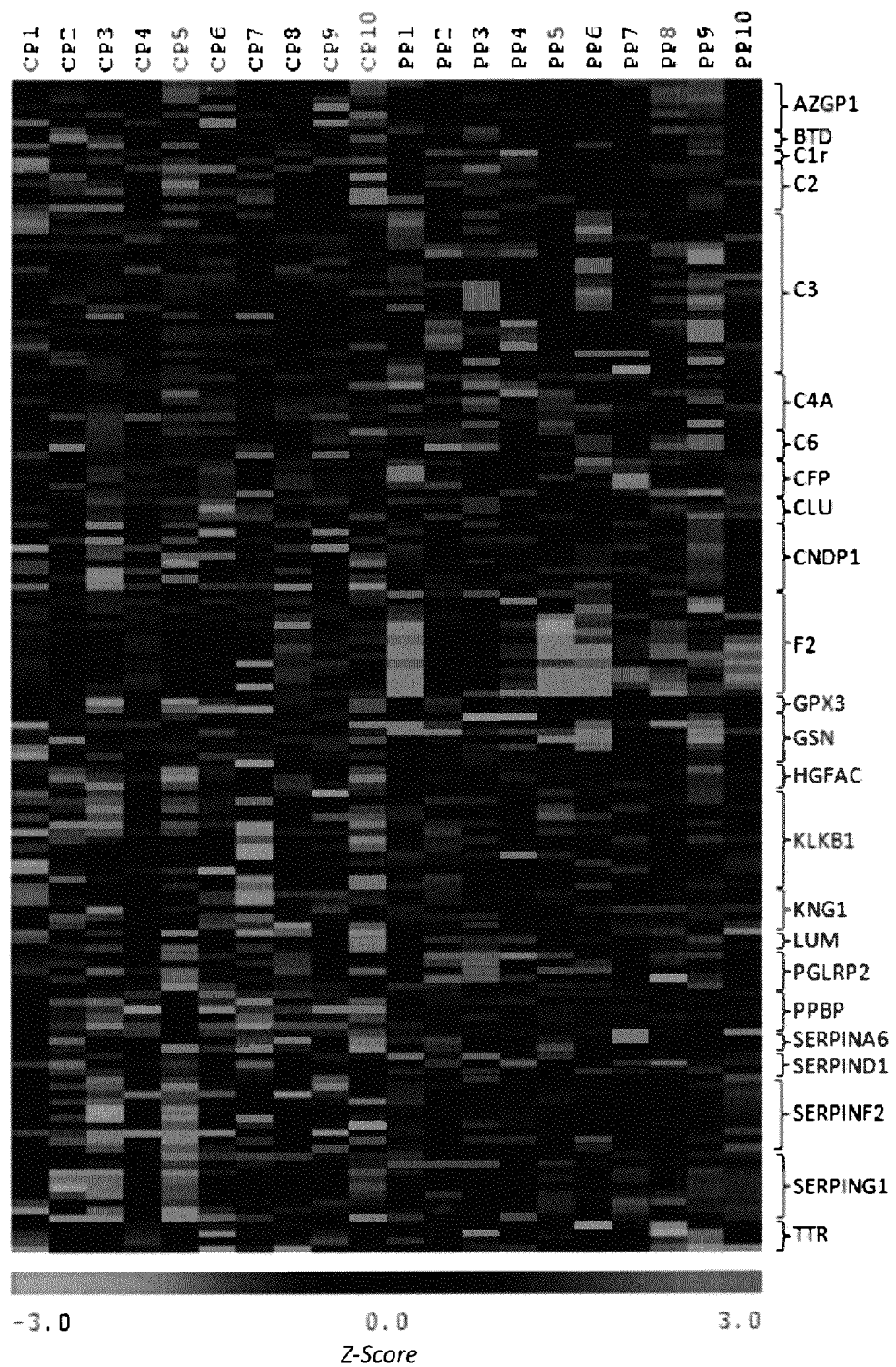
FIG. 1. Candidate protein biomarkers discovered from LC-MS based bottom-up global proteomic profiling in type 1 diabetic patients. Relative protein abundances (Z-Score transformed) are displayed as their constituent relative peptide abundances. Only those proteins with more than 60% of their constitutive peptides passing a t-test on peptide level ($p<0.05$) and followed in the targeted analyses are shown. Each row represents a unique peptide, and each column represents a pooled control or type 1 diabetic patient sample. Ten pooled control and ten pooled patient serum/plasma samples were included in the label-fee quantitative proteomics discovery experiment. CP, control pooled; PP, patient pooled.

The protein sequences listed in the accompanying sequence listing are shown using standard three-letter abbreviations for amino acids.

SEQ ID NO: 1 is an exemplary T1DM-related peptide EIPAWVPFDPAAQITK.

SEQ ID NO: 2 is an exemplary T1DM-related peptide LSSGLVTAALYGR.

SEQ ID NO: 3 is an exemplary T1DM-related peptide SHLIIAQVAK.

SEQ ID NO: 4 is an exemplary T1DM-related peptide LFGEVTSPLFPK.

SEQ ID NO: 5 is an exemplary T1DM-related peptide VSVHPDYR.

SEQ ID NO: 6 is an exemplary T1DM-related peptide GESGGAVFLER.

SEQ ID NO: 7 is an exemplary T1DM-related peptide HAIILLTDGK.

SEQ ID NO: 8 is an exemplary T1DM-related peptide SSGQWQTPGATR.

SEQ ID NO: 9 is an exemplary T1DM-related peptide DFDFVPPVVR.

SEQ ID NO: 10 is an exemplary T1DM-related peptide TGLQEVEVK.

SEQ ID NO: 11 is an exemplary T1DM-related peptide ITQVLHFTK.

SEQ ID NO: 12 is an exemplary T1DM-related peptide ALNHLPLEYNSALYSR.

SEQ ID NO: 13 is an exemplary T1DM-related peptide SISCQEIPGQQSR

SEQ ID NO: 14 is an exemplary T1DM-related peptide ELDESLQVAER.

SEQ ID NO: 15 is an exemplary T1DM-related peptide LFDSDPITVTVPVEVSR

SEQ ID NO: 16 is an exemplary T1DM-related peptide TLLSNLEEAK.

SEQ ID NO: 17 is an exemplary T1DM-related peptide ALEQDLPVNIK

SEQ ID NO: 18 is an exemplary T1DM-related peptide EWVAIESDSVQPVPR

SEQ ID NO: 19 is an exemplary T1DM-related peptide ELLESYIDGR

SEQ ID NO: 20 is an exemplary T1DM-related peptide ETAASLLQAGYK

SEQ ID NO: 21 is an exemplary T1DM-related peptide QEPGENSEILPTLK

SEQ ID NO: 22 is an exemplary T1DM-related peptide YVRPGGGFVPNFQLFEK

SEQ ID NO: 23 is an exemplary T1DM-related peptide AGALNSNDAFVLK

SEQ ID NO: 24 is an exemplary T1DM-related peptide QTQVSVLPEGGETPLFK

SEQ ID NO: 25 is an exemplary T1DM-related peptide TGAQELLR

SEQ ID NO: 26 is an exemplary T1DM-related peptide EALVPLVADHK

SEQ ID NO: 27 is an exemplary T1DM-related peptide VANYVDWINDR

SEQ ID NO: 28 is an exemplary T1DM-related peptide DSVTGTLPK

SEQ ID NO: 29 is an exemplary T1DM-related peptide EIIIHQNYK

SEQ ID NO: 30 is an exemplary T1DM-related peptide IAYGTQGSSGYSLR

SEQ ID NO: 31 is an exemplary T1DM-related peptide IYSGILNLSDITK

SEQ ID NO: 32 is an exemplary T1DM-related peptide DIPTNSPELEETLTHTITK

SEQ ID NO: 33 is an exemplary T1DM-related peptide TVGSDTFYSFK

SEQ ID NO: 34 is an exemplary T1DM-related peptide FNALQYLR

SEQ ID NO: 35 is an exemplary T1DM-related peptide ISNIPDEYFK

SEQ ID NO: 36 is an exemplary T1DM-related peptide NNQIDHIDEK

SEQ ID NO: 37 is an exemplary T1DM-related peptide AGLLRPDYALLGHR

SEQ ID NO: 38 is an exemplary T1DM-related peptide PSLSHLLSQYYGAGVAR

SEQ ID NO: 39 is an exemplary T1DM-related peptide TFTLLDPK

SEQ ID NO: 40 is an exemplary T1DM-related peptide EESLDSDLYAELR

SEQ ID NO: 41 is an exemplary T1DM-related peptide NIQSLEVIGK

SEQ ID NO: 42 is an exemplary T1DM-related peptide AQLLQGLGFNLTER

SEQ ID NO: 43 is an exemplary T1DM-related peptide EENFYVDETTVVK

SEQ ID NO: 44 is an exemplary T1DM-related peptide SVNDLYIQK

SEQ ID NO: 45 is an exemplary T1DM-related peptide TLEAQLTPR

SEQ ID NO: 46 is an exemplary T1DM-related peptide LGNQEPGGQTALK

SEQ ID NO: 47 is an exemplary T1DM-related peptide FQPTLLTLPR

SEQ ID NO: 48 is an exemplary T1DM-related peptide LLDSLPSDTR

SEQ ID NO: 49 is an exemplary T1DM-related peptide LVLLNAIYLSAK

SEQ ID NO: 50 is an exemplary T1DM-related peptide TNLESILSYPK

SEQ ID NO: 51 is an exemplary T1DM-related peptide AADDTWEPFASGK

SEQ ID NO: 52 is an exemplary T1DM-related peptide GSPAINVAVHVFR

Figure 7:
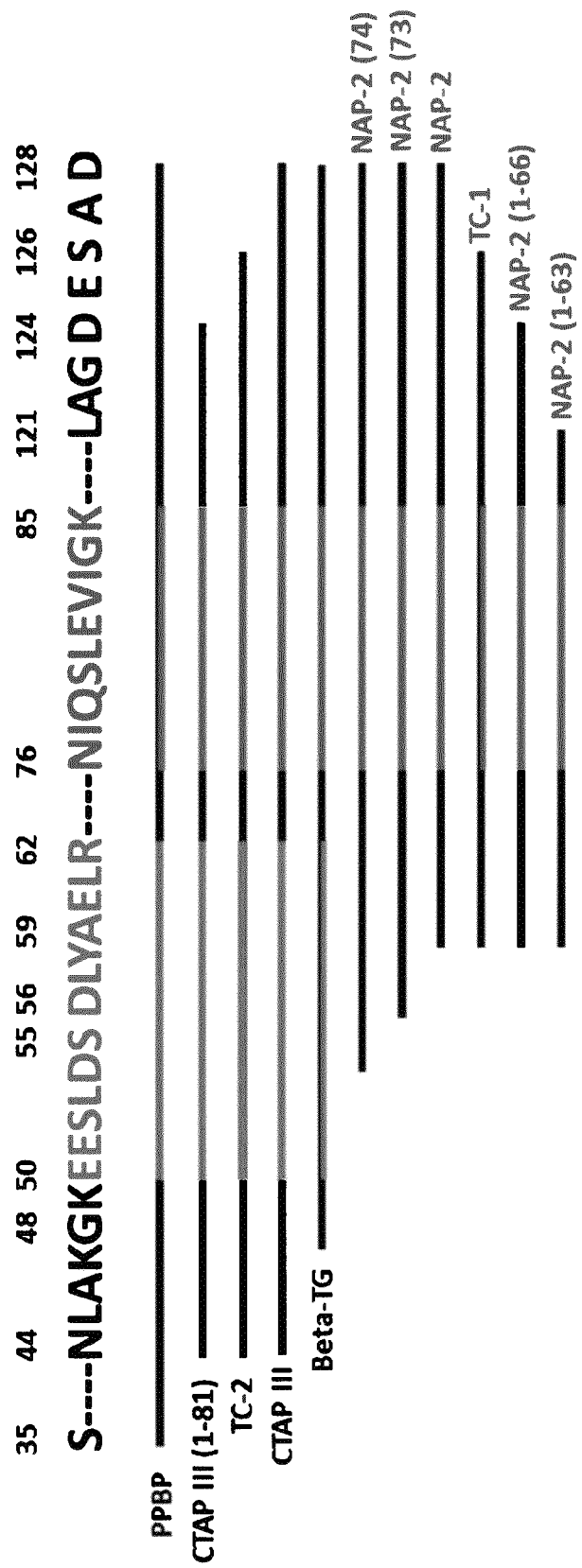
FIG. 7. Sequence alignment of the two peptides representing PPBP (SEQ ID NOS: 40 and 41), with the start (SEQ ID NO: 53) and end (SEQ ID NO: 54) amino acids labeled in the sequence. Both peptides are components of the uncleaved form of PPBP, and CTAPIII, TC-2 and Beta-TG, while peptide NIQSLEVIGK (SEQ ID NO: 41) also exists in TC-1 and the five forms of NAP-2.

SEQ ID NOS: 53 and 54 are the start and end amino acid sequences, respectively, of the PPBP precursor (see FIG. 7).

DETAILED DESCRIPTION

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a protein" includes single or plural proteins and is considered equivalent to the phrase "comprising at least one protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. While the methods have been described and were utilized in testing, it is to be distinctly understood that the disclosure is not limited to any particular form of testing utilized, but is intended to include all methods that are capable of detecting the materials that are set forth in the claims. All references and sequences available on Aug. 12, 2011 associated with the Uniprotein Accession Nos. in Table 2 and the GenBank Accession Nos. listed herein, are herein incorporated by reference.

Antibody: A polypeptide ligand including at least a light chain or heavy chain immunoglobulin variable region which specifically recognizes and binds an epitope of an antigen, such as an endothelial marker or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. In one example, an antibody (such as a monoclonal or polyclonal antibody) specifically binds to one of the proteins or peptides listed in Tables 6a or 6b, but not other proteins (such as other proteins found in human serum or plasma).

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen which are then purified from the mammal's serum.

A "chimeric antibody" has framework residues from one species, such as human, and CDRs (which generally confer antigen binding) from another species, such as a murine antibody that specifically binds an endothelial marker.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585, 089).

Array: An arrangement of molecules, such as biological macromolecules (such as peptides or nucleic acid molecules), in addressable locations on or in a substrate. A "microarray" is an array that is miniaturized so as to require or be aided by microscopic examination for evaluation or analysis.

The array of molecules ("features") makes it possible to carry out a very large number of analyses on a sample at one time. In certain example arrays, one or more molecules (such as oligonucleotide probes or antibodies) will occur on the array a plurality of times (such as twice), for instance to provide internal controls. The number of addressable locations on the array can vary, for example from at least two, to at least 10, at least 20, at least 30, at least 50, at least 75, at least 100, at least 150, at least 200, at least 300, at least 500, least 550, at least 600, at least 800, at least 1000, at least 10,000, or more, such as 5 to 20, 5 to 100, or 5 to 1000 locations. In particular examples, an array includes nucleic acid molecules, such as oligonucleotide sequences that are at least 15 nucleotides in length, such as about 15-40 nucleotides in length, and a specific for nucleic acid molecules encoding the T1DM-related proteins (or peptide fragments of such proteins) listed in Table 6a or 6b. In particular examples, an array includes antibodies or proteins which can be used to detect T1DM-associated nucleic acids. For example, such arrays can be used to detect any combination of at least 2 of the T1DM-related nucleic acid molecules or proteins (or peptide fragments of such proteins) listed in any of Tables 6a or 6b, such as at least 3, at least 4, at least 5, at least 6, at least 7, at least 8, at least 9, at least 10, at least 15, at least 20, at least 24, at least 25, at least 30, at least 35, at least 40, at least 45, at least 50, or at least 52 of the molecules listed in Table 6a or 6b.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Binding affinity: Affinity of one molecule for another, such as an antibody for an antigen (for example, the proteins and peptides shown in Tables 6a or 6b). In one example, affinity is calculated by a modification of the Scatchard method described by Frankel et al., *Mol. Immunol.*, 16:101-106, 1979. In another example, binding affinity is measured by an antigen/antibody dissociation rate. In yet another example, a high binding affinity is measured by a competition radioimmunoassay. In several examples, a high binding affinity is at least about $1 \times 10^{-8}$ M. In other examples, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Control: A sample or standard used for comparison with a test sample, such as a biological sample, e.g., a biological sample obtained from a patient (or plurality of patients) or a cell culture. In some embodiments, the control is a sample obtained from a healthy patient (or plurality of patients) (also referred to herein as a "normal" control), such as a normal sample (e.g., one that does not have T1DM). In some embodiments, the control is a historical control or standard value (i.e. a previously tested control sample or group of samples that represent baseline or normal values). In some embodiments the control is a standard value representing the average value (or average range of values) obtained from a plurality of patient samples, such as an average value of the quantity for each protein or peptide listed in Table 6a or 6b.

A control can also be represented by a reference value or range of values representing an amount of activity or expression determined to be representative of a given condition. Reference values can include a range of values, real or relative expected to occur under certain conditions. These values can be compared with experimental values to determine if a given molecule is up-regulated or down-regulated in a particular sample for instance. In one example, a reference value or range of values represents an amount of activity or expression of a T1DM-related nucleic acid molecule or protein or peptide in a sample, such as a sample from a non-T1DM patient. This value can then be used to determine if the subject from whom a test sample was obtained has T1DM or is predisposed to developing T1DM by comparing this reference value of expression to the level of expression detected in the test sample. In a particular example, a change in expression or activity in one or more T1DM-related molecules (such as those in Table 6a or 6b) in a test sample as compared to such a reference value indicates that the subject has T1DM.

Detecting: To measure or identify the existence, occurrence, presence, or fact of something. General methods of detecting are known to the person of ordinary skill in the art and may be supplemented with the protocols and reagents disclosed herein. For example, included herein are methods of detecting a protein or peptide fragment shown in Table 6a or 6b. Detection can be qualitative or quantitative.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, biopsy and analysis of biological samples obtained from a subject. In one example diagnosis is determining whether a subject has T1DM.

Diabetes mellitus: A disease caused by a relative or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (T1DM; sometimes referred to as "insulin-dependent diabetes" or "juvenile-onset diabetes") is an auto-immune disease characterized by destruction of the pancreatic β cells that leads to a total or near total lack of insulin. In type 2 diabetes (T2DM; sometimes referred to as "non-insulin-dependent diabetes" or "adult-onset diabetes"), the body does not respond to insulin, though it is present.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W.B. Saunders Co., Philadelphia, 1992, 19$^{th}$ ed.).

The methods disclosed herein provide a means of identifying a subject who has T1DM or type I pre-diabetes. A "non-diabetic" or "normal" subject does not have any form of diabetes, such as T1DM or pre-diabetes.

Differential expression: A difference, such as an increase or decrease, in the conversion of the information encoded in a gene (such as a T1DM-related gene) into messenger RNA, the conversion of mRNA to a protein, or both. In some examples, the difference is relative to a control or reference value, such as an amount of protein or peptide expression that is expected in a subject who does not have T1DM, or an amount expected in a subject who has T1DM. Detecting differential expression can include measuring a change in gene or protein expression, such as a change in amount (e.g., qualitative or quantitative) of one or more T1DM-related peptide fragments, such as those listed in Tables 6a and 6b.

Downregulated or inactivation: When used in reference to the expression of a nucleic acid molecule (such as a T1DM-related nucleic acid molecule), such as a gene, refers to any process which results in a decrease in production of a gene product, such as the protein or peptides in Table 6a and 6b with a negative fold change (e.g., EIPAWVPFDPAAQITK, SEQ ID NO: 1). A gene product can be RNA (such as mRNA, rRNA, tRNA, and structural RNA) or protein. Therefore, downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Downregulation includes any detectable decrease in the production of a gene product. In certain examples, production of a gene product decreases by at least 1.2-fold, for example at least 1.3-fold, at least 1.5 fold, at least 2-fold, at least 3-fold, at least 4-fold, or at least 8-fold as compared to a control (such an amount of protein detected in a normal cell). For example the proteins and protein fragments listed in Tables 6a and 6b having a negative fold change value are downregulated in subjects who have T1DM (such as GSN and TTR proteins). In one example, a control is a relative amount of gene expression or protein expression in a blood sample from a subject who does not have T1DM (and in some examples does not have T1DM or T2DM).

Expression: The process by which the coded information of a gene is converted into an operational, non-operational, or structural part of a cell, such as the synthesis of a protein. Gene expression can be influenced by external signals (such as a hormone). Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a T1DM-related nucleic acid molecule or protein can be altered relative to a normal (wild type) nucleic acid molecule or protein (such as in a patient not having T1DM or who is prediabetic). Alterations in gene expression, such as differential expression, include but are not limited to: (1) overexpression (e.g., upregulation); (2) underexpression (e.g., downregulation); or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount (e.g., upregulation); (5) expression of a decreased amount of the protein compared to a control or standard amount (e.g., downregulation); (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have T1DM) as well as laboratory values, even though possibly arbitrarily set, keeping in mind that such values can vary from laboratory to laboratory.

Laboratory standards and values may be set based on a known or determined population value and can be supplied in the format of a graph or table that permits comparison of measured, experimentally determined values.

Gelsolin (GSN): OMIM 137350: A protein of leukocytes, platelets, and other cells, which severs actin filaments in the presence of submicromolar calcium, thereby solating cytoplasmic actin gels. GSN sequences are publicly available. For example, GenBank Accession Nos: NM_000177.4 discloses a human GSN nucleic acid sequence and GenBank Accession Nos: 1211330A and NP_000168.1 disclose human GSN protein sequences.

In one example, a GSN sequence includes a full-length wild-type (or native) sequence, as well as GSN allelic variants that retain the ability to sever actin. In certain examples, GSN has at least 80% sequence identity, for example at least 85%, at least 90%, at least 95%, or at least 98% sequence identity to a native GSN and retains GSN biological activity (or encodes a protein with GSN activity).

Label: A detectable compound. In some examples, a label is conjugated directly or indirectly to another molecule, such as an antibody or a protein, to facilitate detection of that molecule. For example, the label can be capable of detection by ELISA, spectrophotometry, flow cytometry, or microscopy. Specific, non-limiting examples of labels include fluorophores, chemiluminescent agents, enzymatic linkages, and radioactive isotopes. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In a particular example, a label is conjugated to an antibody specific for a protein or peptide disclosed in Table 6a or 6b to allow for the diagnosis of T1DM.

Lateral flow device: A device that absorbs or adsorbs a liquid sample (such as a serum or plasma sample), routes that liquid sample to a detection zone, and uses antibody- or lectin-based detection methods to generate a visible signal in response to the presence or absence of a specific antigen (such as a protein or glycoprotein) or lectin-binding biomolecule (such as a glycoprotein or glycolipid). The device can be a test strip used in lateral flow chromatography, in which a test sample fluid, suspected of containing an analyte (such as one or more of the proteins or peptide fragments in Table 6a or 6b), flows (for example by capillary action) through the strip (which is frequently made of bibulous materials such as paper, nitrocellulose, and cellulose). The test fluid and any suspended analyte can flow along the strip to a detection zone in which the analyte (if present) interacts with a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,258,548; 6,555,390; 6,699,722; and 6,368,876; EP 0810436; and WO 92/12428; WO 94/01775; WO 95/16207; and WO 97/06439.

Many lateral flow devices are one-step lateral flow assays in which a biological fluid is placed in a sample area on a bibulous strip (though, non-bibulous materials can be used, and rendered bibulous by applying a surfactant to the material), and allowed to migrate along the strip until the liquid comes into contact with a specific binding partner (such as a lectin or antibody) that interacts with an analyte (such as one or more of the proteins or peptide fragments in Table 6a or 6b) in the liquid. Once the analyte interacts with the binding partner, a signal (such as a fluorescent or otherwise visible dye) indicates that the interaction has occurred. Multiple discrete binding partners can be placed on the strip (for example in parallel lines) to detect multiple analytes (such as T1DM-related proteins or peptides provided herein) in the liquid. The test strips can also incorporate control indicators, which provide a signal that the test has adequately been performed, even if a positive signal indicating the presence (or absence) of an analyte is not seen on the strip.

Mammal: This term includes both human and non-human mammals. Examples of mammals include, but are not limited to: humans, pigs, cows, goats, cats, dogs, rabbits and mice. In one example, a mammal has or is susceptible to developing T1DM.

N-acetylmuramoyl-L-alanine amidase (PGLYRP2): EC 3.5.1.28. An enzyme that catalyzes a chemical reaction that cleaves the link between N-acetylmuramoyl residues and L-amino acid residues in certain cell-wall glycopeptides. Pglypr2 sequences are publicly available. For example, GenBank Accession No: NM_052890.3 discloses a human Pglypr2 nucleic acid sequence and GenBank Accession No: NP_443122.3 discloses a human Pglypr2 protein sequence.

In one example, a Pglypr2 sequence includes a full-length wild-type (or native) sequence, as well as Pglypr2 allelic variants that retain the ability to function as a protease. In certain examples, Pglypr2 has at least 80% sequence identity, for example at least 85%, at least 90%, at least 95%, or at least 98% sequence identity to a native Pglypr2 and retains Pglypr2 biological activity (or encodes a protein with Pglypr2 activity).

Platelet basic protein (PPBP): The PPBP precursor can be proteolytically cleaved into 10 polypeptide chains with different functions (for example see Uniprot ID No. P02775). PPBP sequences are publicly available. For example, GenBank Accession No: AF349466 discloses a human PPBP nucleic acid sequence and GenBank Accession Nos: AAK29642 and NP_002695.1 disclose human PPBP protein sequences.

In one example, a PPBP sequence includes a full-length wild-type (or native) sequence, as well as PPBP allelic variants that retain the ability to function as a protease. In certain examples, PPBP has at least 80% sequence identity, for example at least 85%, at least 90%, at least 95%, or at least 98% sequence identity to a native PPBP and retains PPBP biological activity (or encodes a protein with PPBP activity).

Plasma protease C1 inhibitor (SerpinG1): OMIM 606860: A protease inhibitor belonging to the serpin superfamily, which inhibits the complement system to prevent spontaneous activation. SerpinG1 sequences are publicly available. For example, GenBank Accession No: NM_000062.2 discloses a human SerpinG1 nucleic acid sequence and GenBank Accession Nos: NP_000053.2 and NP_001027466.1 disclose human SerpinG1 protein sequences.

In one example, a SerpinG1 sequence includes a full-length wild-type (or native) sequence, as well as SerpinG1 allelic variants that retain the ability to function as a protease. In certain examples, SerpinG1 has at least 80% sequence identity, for example at least 85%, at least 90%, at least 95%, or at least 98% sequence identity to a native SerpinG1 and retains SerpinG1 biological activity (or encodes a protein with SerpinG1 activity).

Prognosis: To determine whether a subject will develop a disease in the future, such as the predisposition of a subject to develop T1DM in the future.

Sample: Biological specimens containing genomic DNA, cDNA, RNA, or protein obtained from the cells of a subject, such as those present in peripheral blood, urine, saliva, semen, tissue biopsy, surgical specimen, fine needle aspriates, amniocentesis samples and autopsy material. In one example, a sample includes plasma or serum obtained from a mammalian subject. In one example, the sample is a liquid sample.

Solid support (or substrate): Any material which is insoluble, or can be made insoluble by a subsequent reaction. The arrays and lateral flow devices disclosed herein for detecting T1DM-related molecules can include a solid support. Numerous and varied solid supports are known to those in the art and include, without limitation, nitrocellulose, the walls of wells of a reaction tray, multi-well plates, test tubes, polystyrene beads, magnetic beads, membranes, and microparticles (such as latex particles). Any suitable porous material with sufficient porosity to allow access by detector reagents and a suitable surface affinity to immobilize capture reagents (e.g., lectins or antibodies) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

It is contemplated that porous solid supports, such as nitrocellulose, described herein can be in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

The surface of a solid support may be activated by chemical processes that cause covalent linkage of an agent (e.g., a capture reagent, such as an antibody) to the support. However, any other suitable method may be used for immobilizing an agent (e.g., a capture reagent) to a solid support including, without limitation, ionic interactions, hydrophobic interactions, covalent interactions and the like. The particular forces that result in immobilization of an agent on a solid phase are not important for the methods and devices described herein.

A solid phase can be chosen for its intrinsic ability to attract and immobilize an agent, such as a capture reagent (such as an antibody or oligonucleotide probe). Alternatively, the solid phase can possess a factor that has the ability to attract and immobilize an agent, such as a capture reagent. The factor can include a charged substance that is oppositely charged with respect to, for example, the capture reagent itself or to a charged substance conjugated to the capture reagent. In another embodiment, a specific binding member may be immobilized upon the solid phase to immobilize its binding partner (e.g., a capture reagent). In this example, therefore, the specific binding member enables the indirect binding of the capture reagent to a solid phase material.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

A "lateral flow substrate" is any solid support or substrate that is useful in a lateral flow device.

Subject: Living multicellular vertebrate organisms, a category which includes both human and veterinary subjects that are in need of the desired diagnosis, such as diagnosis of T1DM. Examples include, but are not limited to: humans, apes, dogs, cats, mice, rats, rabbits, horses, pigs, and cows. In some examples a subject is one who has T1DM, or is suspected of having T1DM.

Transthyretin (TTR): OMIM 176300: A serum and cerebrospinal fluid carrier of the thyroid hormone thyroxine (T4) and retinol. TTR sequences are publicly available. For example, GenBank Accession No: NM_000371.3 discloses a human TTR nucleic acid sequence and GenBank Accession Nos: NP_000362.1 and ABI63351.1 disclose human TTR protein sequences.

In one example, a TTR sequence includes a full-length wild-type (or native) sequence, as well as TTR allelic variants that retain the ability to transport T4 and retinol. In certain examples, TTR has at least 80% sequence identity, for example at least 85%, at least 90%, at least 95%, or at least 98% sequence identity to a native TTR and retains TTR biological activity (or encodes a protein with TTR activity).

Upregulated or activation: When used in reference to the expression of a molecule, such as a gene or protein, refers to any process which results in an increase in production of a gene product. A gene product can be RNA (such as mRNA, rRNA, tRNA, and structural RNA) or protein. Therefore, upregulation or activation includes processes that increase the presence of a T1DM-related protein or peptide in the blood, such as one or more of those shown in Tables 6a or 6b with a positive fold-change value (such as TNLESILSYPK, SEQ ID NO: 50).

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Upregulation can include inhibition of repression as well as stimulation of expression above an existing level. Examples of processes that increase translation include those that increase translational initiation, those that increase translational elongation and those that increase mRNA stability.

Upregulation includes any detectable increase in the production of a gene product, such as a T1DM-associated protein or peptide. In certain examples, detectable T1DM-related protein or peptide in the blood increases by at least 1.5 fold, such as at least 2-fold, at least 3-fold, at least 4-fold, at least 5-fold, at least 6-fold, at least 7-fold, or at least 8-fold, as compared to a control (such an amount of detectable T1DM-related protein or peptide in the blood in a non-T1DM sample). For example these proteins and peptides listed in Tables 6a and 6b having a positive fold change value are upregulated in subjects who have T1DM. In one example, a control is a relative amount of expression in a blood sample observed in a subject who does not have T1DM (and in some examples does not have T2DM).

Type 1Diabetes Mellitus-Related Molecules

The inventors have identified at least 24 different proteins whose expression is altered (such as upregulated or downregulated) in patients having type I diabetes mellitus (T1DM), relative to patients not having T1DM or who are prediabetic (see Table 6a). These 24 proteins and their corresponding 52 peptide fragments (and nucleic acid molecules) are referred to herein as "type I diabetes mellitus-related molecules" and includes type I diabetes mellitus-related nucleic acid molecules (such as DNA, RNA, for example cDNA or mRNA) and proteins. The term includes those molecules listed in Tables 6a and 6b.

Based on this observation, methods are provided for screening for T1DM by detecting or measuring an amount of one or more of these proteins or peptide fragments thereof, such as the specific peptide fragments listed in the tables herein, as well as the corresponding encoding nucleic acid molecules. The disclosed methods provide a rapid, straightforward, and accurate screening method performed in one assay for diagnosis of T1DM (for example to determine if a subject is predisposed to develop T1DM or has T1DM). It allows identification of subjects who may require treatment for T1DM. For example, by establishing that an individual has T1DM, effective therapeutic measures, such as insulin therapy or diet modifications, can be instituted. Arrays and kits that can be used in such methods are also provided.

The results of shown herein using non-diabetic, diabetic and control samples showed the presence of each of these proteins at significantly elevated or decreased levels in persons diagnosed with T1DM, while the normal and control samples did not have these altered levels. Thus a method wherein a blood sample (such as serum or plasma) from a mammal (such as a human) is tested for at least one protein or peptide fragment thereof from Table 6a or 6b serves as an effective predictive or diagnostic screen or test for T1DM. In addition, the disclosed T1DM-related proteins can be further explored in targeted proteomic studies utilizing isotopically-labeled peptide internal standards for absolute quantitation, which enable the determination of laboratory-defined sensitivity and specificity with blinded samples. Further embodiments of the disclosure can be made by combining different combinations of these T1DM-related proteins, either alone or in combination with other biomarkers or housekeeping genes.

Various methods for performing the quantitative and qualitative analysis of the T1DM-related proteins (or corresponding nucleic acid molecules) may be utilized. In one embodiment, LC-MS/MS analyses were performed, however it is to be distinctly understood that the disclosure is not limited thereto. Any reliable manner of performing quantitative or qualitative analysis of a sample for the presence and quantity of any of the preselected T1DM-related biomarkers set forth herein and discussed may be utilized. In one example, a suitably programmed computer is used to measure the amounts (quantitative or qualitative) of one or more T1DM-related biomarkers set forth herein, to compare the amount of T1DM-related biomarker to a control, or both. In some examples, a suitably programmed computer provides an output to a user, for example a value or range of values relating to an amount of expression of the measured T1DM-related biomarkers.

In particular examples, the following proteins and their corresponding peptides were found to be downregulated in patients having T1DM as compared to a normal (non-diabetic) subject (see Table 6a): AZGP1; BTD; C1R; C2; C3; C4A; C6; CFP; CLU; F2; GPX3; GSN; HGFAC; KLKB1; KNG1; LUM; PGLYRP2; SERPINA6; SERPIND1; and TTR. In particular examples, the following proteins and their corresponding peptides were found to be downregulated in patients having T1DM as compared to a normal (non-diabetic) subject (see Table 6b): GSN, PGLYRP2, and TTR. Thus, in some examples detection of downregulation of GSN, PGLYRP2, or TTR, or combinations thereof (such as PGLYRP2 and TTR, alone or in combination) diagnoses the subject with T1DM. In particular examples, the following proteins and their corresponding peptides were found to be upregulated in patients having T1DM as compared to a normal (non-diabetic) subject (see Table 6a): C2; CNDP1; HGFAC; PPBP; SERPINF2; and SERPING1. In particular examples, the following proteins and their corresponding peptides were found to be upregulated in patients having T1DM as compared to a normal (non-diabetic) subject (see Table 6b): PPBP and SERPING1. Thus, in some examples detection of upregulation of PPBP and/or SERPING1 diagnoses the subject with T1DM. In some examples, detection of downregulation of GSN, PGLYRP2, TTR, or combinations thereof and detection of upregulation of PPBP and/or SERPING1 diagnoses the subject with T1DM. In some examples, detection of downregulation of PGLYRP2 and detection of upregulation of PPBP, SERPING1, or both PPBP and SERPING1 diagnoses the subject with T1DM.

One skilled in the art will appreciate that a full-length protein can be detected, or individual peptides thereof. For example SERPING1 was found to be upregulated in subjects having T1DM relative to subjects not having type I diabetes. Therefore, to determine whether expression of SERPING1 is increased in a test sample, the full-length SERPING1 protein can be detected (e.g., using an antibody), or one or more of the individual SERPING1 peptide sequences can be detected (such as any of SEQ ID NOs: 47-50, or combinations thereof), for example using mass spec methods. Thus, in some examples detection of downregulation of SEQ ID NO: 23, 24, 25, 37, 38, 39, 51 or 52, or combinations thereof (such as SEQ ID NO: 37, 38, 39, 51 or 52, alone or in combination) diagnoses the subject with T1DM. Thus, in some examples detection of upregulation of SEQ ID NO: 40, 41, 47, 48, 49 and/or 50 diagnoses the subject with T1DM. In some examples, detection of downregulation of SEQ ID NO: 23, 24, 25, 37, 38, 39, 51 or 52, or combinations thereof and detection of upregulation of SEQ ID NO: 40, 41, 47, 48, 49 and/or 50 diagnoses the subject with T1DM. In some examples, detection of downregulation of SEQ ID NO: 37, 38, and/or 39, and detection of upregulation of SEQ ID NO: 41, 47, 48, 49 and/or 50 diagnoses the subject with T1DM.

In addition, nucleic acid molecules encoding such peptides can also be detected.

Diagnosis of Type 1 Diabetes Mellitus

Provided herein are methods of diagnosing T1DM. Particular examples of diagnosing T1DM include determining whether a subject, such as an otherwise healthy subject, or a subject suspected or at risk of having T1DM, or who has had T1DM, currently has T1DM or is predisposed to developing T1DM in the future. In some examples, a sample (such as a serum or blood plasma sample) obtained from a mammal (such as a human) is analyzed to detect the presence of particular T1DM-associated molecules (such as those in Tables 6a or 6b). In some examples, detection includes quantification. The disclosed methods can further include selecting subjects having or suspecting of having T1DM, and in some examples obtaining a sample from such a patient, and analyzing the sample as described herein.

In particular examples, the methods include detecting expression (such as an increase or decrease in gene or protein expression) in any combination of at least 2, at least 5, at least 10, at least 15, at least 20, or all 24 of the proteins (or nucleic acids encoding such proteins) listed in Table 6a. In one example, the method includes detecting all of the proteins (or nucleic acids encoding such proteins) in Table 6a or 6b. The amount of protein (or nucleic acid encoding such proteins) detected can be quantified. In particular examples, the methods include detecting expression (such as an increase or decrease in gene or protein expression) in any combination of at least 2, at least 5, at least 10, at lest 14, at least 15, at least 20, at least 24, at least 30, at least 40, at least 50 or all 52 of the peptides (or nucleic acids encoding such proteins) listed in Table 6a or 6b.

Detecting the level of expression can involve measuring an amount of the T1DM-related molecules in a sample obtained or derived from the subject. In some examples, the amount of protein (or nucleic acid encoding such proteins) detected is compared to an amount of the same protein present or expected in a control sample, such as a sample from a subject not having T1DM. For example, a difference (such as an increase or a decrease reflecting an upregulation or downregulation, respectively) in the level of at least 1, at least 2, at least 3, at least 4, at least 5, at least 6, at least 7, at least 8, at least 9, at least 10, at least 14, at least 15, at least 20, at least 24, at least 30, at least 40, at least 50, or all 52 of the T1DM-related peptides listed in Tables 6a or 6b (such as all of the proteins or peptides listed in Table 6a or 6b) in the subject relative to the control indicates that the subject has T1DM. In one example, a difference (such as an increase or a decrease reflecting an upregulation or downregulation, respectively) in the level of 1, 2, 3, 4, 5, 6, 7, 8, 9, 10, 14, 15, 20, 24, 30, 40, 50, or all 52 of the T1DM-related molecules listed in Tables 6a or 6b (such as all of the proteins or peptides listed in Table 6a or 6b) in the subject relative to the control sample indicates that the subject has T1DM. In some examples, the amount of protein or peptide (or nucleic acid encoding such proteins) detected is compared to a reference value or range of values expected if the subject has, does not have, or is predisposed to developing T1DM (or combinations thereof). For example, a reduction of at least 1.1 fold (such as at least 1.2 fold, at least 1.3 fold, at least 1.4 fold, at least 1.5 fold, at least 2 fold, at least 2.5 fold, or at least 3 fold) of a T1DM-related molecule in a test sample relative to the amount of the same T1DM-related molecule in a non-T1DM control (or an amount expected in such a sample), indicates that the particular T1DM-related molecule is downregulated in the test sample. For example, it is shown herein that TTR is downregulated in subjects having T1DM relative to subjects not having T1DM (see Tables 6a and 6b). In contrast, an increase of at least at least 1.1 fold (such as at least 1.2 fold, at least 1.3 fold, at least 1.4 fold, at least 1.5 fold, at least 2 fold, at least 2.5 fold, at least 3 fold, at least 4 fold, at least 5 fold, at least 8 fold or at least 10 fold) of a T1DM-related molecule in a test sample relative to the amount of the same T1DM-related molecule in a non-T1DM control (or an amount expected in such a sample), indicates that the particular T1DM-related molecule is upregulated in the test sample. For example, it is shown herein that PPBP is upregulated in subjects having T1DM relative to subjects not having T1DM (see Tables 6a and 6b).

In particular examples, detection of differential expression in at least 1 T1DM-related nucleic acid molecule (or protein or peptide) listed in Tables 6a or 6b, such as changes in gene (or protein) expression in any combination of at least 2, at least 3, at least 4, at least 5, at least 6, at least 7, at least 8, at least 9, at least 10, at least 14, at least 15, at least 20, at least 24, at least 30, at least 40, at least 50, or at least 52 (such as those in Table 6a or 6b or peptides thereof), indicates that the subject has T1DM or is predisposed to developing T1DM. An appropriate treatment can then be selected or initiated to treat or prevent T1DM. Thus, in some examples, the methods further include treating or preventing T1DM, for example administering insulin to the subject diagnosed with T1DM. Differential expression can be represented by increased or decreased expression in T1DM-related molecule (for instance, a nucleic acid or a protein). For example, differential expression includes, but is not limited to, an increase or decrease in an amount of a nucleic acid molecule or protein, the stability of a nucleic acid molecule or protein, the localization of a nucleic acid molecule or protein, or the biological activity of a nucleic acid molecule or protein.

In particular examples, the number of T1DM-related molecules screened is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, or at least 52 T1DM-related molecules. In other examples, the methods employ screening no more than 52, no more than 40, no more than 35, no more than 30, no more than 25, no more than 22, no more than 20, no more than 15, no more than 14, no more than 13, no more than 12, no more than 11, no more than 10, no more than 9, no more than 8, no more than 7, no more than 6, or no more than 5 T1DM-related molecules, such as 3 to 20 or 3 to 10 T1DM-related molecules.

In particular examples, the T1DM-related molecules detected in the sample to diagnose or prognose T1DM include or consist of, all 52 peptides of SEQ ID NOS: 1-52 (see Table 6a), all 24 proteins listed in Table 6a, all 14 peptides of SEQ ID NO: 23, 24, 25, 37, 38, 39, 40, 41, 47, 48, 49, 50, 51, or 52 (see Table 6b), or all 5 proteins listed in Table 6b. In other examples, the T1DM-related molecules detected in the sample to diagnose or prognose T1DM include or consist of at least 2, 3, 4, 5, 6, 7, 8, 9, 10, 11, 12, 13 or 14 of the peptides shown in SEQ ID NO: 23, 24, 25, 37, 38, 39, 40, 41, 47, 48, 49, 50, 51, or 52 (see Table 6b). In yet other examples, the T1DM-related molecules detected in the sample to diagnose or prognose T1DM include or consist of at least 2, 3, 4, 5, 6, 7, or 8 of the peptides shown in SEQ ID NO: 37, 38, 39, 41, 47, 48, 49, or 50 (see Table 3). In particular examples, the T1DM-related molecules detected in the sample to diagnose or prognose T1DM include or consist of, platelet basic protein (PPBP) or its various cleavage forms; plasma protease C1 inhibitor (SERPING1); N-acetylmuramoyl-L-alanine amidase (PGLYRP2); PPBP and SERPING1; or PGLYRP2, PPBP and SERPING1. In particular examples, the T1DM-related molecules detected in the sample to diagnose or prognose T1DM include or consist of, the peptides shown in SEQ ID NO: 41; SEQ ID NO: 48; SEQ ID NO: 41 and SEQ ID NO: 48; SEQ ID NO: 47; SEQ ID NO: 49; SEQ ID NO: 50; SEQ ID NO: 47, SEQ ID NO: 48, SEQ ID NO: 49, and SEQ ID NO: 50; SEQ ID NO: 41, SEQ ID NO: 47, SEQ ID NO: 48, SEQ ID NO: 49, and SEQ ID NO: 50, or combinations thereof, for example in combination with one or more of SEQ ID NO: 37, 38, and/or 39. Particular levels of up- or down-regulation observed when compared to a healthy control (e.g., population of subjects not having T1DM) for each of these T1DM-related molecules is shown in Tables 1-3 below.

In particular examples, the disclosed method of diagnosing T1DM is at least 85% sensitive (such as at least 90% sensitive, at least 95% sensitive, at least 98% sensitive, at least 99% sensitive, or 100% sensitive) and at least 85% specific (such as at least 90% specific, at least 95% specific, at least 98% specific, at least 99% specific or 100% specific) for determining whether a subject has or is predisposed to developing T1DM. For example, using the methods provided herein, blinded samples can be used to determine the sensitivity and specificity for particular combinations of T1DM-related molecules.

In some examples, the disclosed method of diagnosing T1DM (or the peptides or proteins analyzed) has an AUC of at least 0.90, at least 0.95, or at least 1.

Tables 1-3 below show particular combinations of proteins or peptides that can be analyzed, the resulting change in expression relative to a healthy control that diagnoses T1DM.

TABLE 1

Diagnosis of T1DM by analysis of 22 proteins or 44 peptides as compared to healthy control

| Protein | Peptide (SEQ ID NO:) | Change in Expression Relative to Healthy Control to diagnose T1DM |
|---|---|---|
| AZGP1 | EIPAWVPFDPAAQITK (1) | Downregulated by at least 1.2 fold or decreased expression by at least 5%, at least 10%, or at least 15% |
| C1R | LFGEVTSPLFPK (4) | Downregulated by at least 1.1 fold, at least 1.2 fold, at least 1.4 fold, or at least 1.6 fold or decreased expression by at least 10%, at least 20%, at least 25%, at least 30%, or at least 40% |
| C1R | VSVHPDYR (5) | Downregulated by at least 1.1 fold or decreased expression by at least 5% or at least 10% |
| C2 | HAIILLTDGK (7) | Upregulated by at least 1.2 fold, or at least 1.4 fold, or increased expression by at least 5%, at least 10%, at least 15%, at least 20%, or at least 30% |
| C2 | SSGQWQTPGATR (8) | Upregulated by at least 1.2 fold or at least 1.3 fold, or at least 1.4 fold, or increased expression by at least 5%, at least 10%, at least 15%, at least 20%, or at least 25% |
| C3 | DFDFVPPVVR (9) | Downregulated by at least 1.2 fold, at least 1.3 fold, at least 1.4 fold, or at least 1.7 fold or decreased expression by at least 10%, at least 20%, at least 25%, at least 30%, at least 40%, at least 50%, or at least 60% |
| C3 | TGLQEVEVK (10) | Downregulated by at least 1.2 fold, at least 1.3 fold, at least 1.4 fold, or at least 1.7 fold or decreased expression by at least 10%, at least 20%, at least 25%, at least 30%, at least 40%, at least 50%, or at least 60% |
| C4A | ITQVLHFTK (11) | Downregulated by at least at least 1.2 fold, at least 1.4 fold, or at least 1.6 fold or decreased expression by at least 10%, at least 20%, at least 25%, at least 30%, or at least 40% |
| C6 | ALNHLPLEYNSALYSR (12) | Downregulated by at least at least 1.2 fold, at least 1.3 fold, or at least 1.4 fold, or decreased expression by at least 10%, at least 20%, at least 25%, at least 30%, or at least 35% |

TABLE 1 -continued

Diagnosis of T1DM by analysis of 22 proteins or 44 peptides as compared to healthy control

| Protein | Peptide (SEQ ID NO:) | Change in Expression Relative to Healthy Control to diagnose T1DM |
|---|---|---|
| CFP | SISCQEIPGQQSR (13) | Downregulated by at least 1.2 fold, at least 1.3 fold, at least 1.4 fold, or at least 1.6 fold, or decreased expression by at least 10%, at least 20%, at least 25%, at least 30%, or at least 35% |
| CLU | ELDESLQVAER (14) | Downregulated by at least 1.1 or at least 1.2 fold, or decreased expression by at least 5%, at least 15%, or at least 20% |
| CLU | LFDSDPITVTVPVEVSR (15) | Downregulated by at least 1.2 fold, or at least 1.3 fold, or decreased expression by at least 5%, at least 15%, or at least 20% |
| CLU | TLLSNLEEAK (16) | Downregulated by at least 1.1 fold, at least 1.2 fold or at least 1.3 fold, or decreased expression by at least 5%, at least 15%, at least 20%, or at least 25% |
| CNDP1 | ALEQDLPVNIK (17) | Upregulated by at least 1.2 fold, or increased expression by at least 5%, at least 10%, or at least 15% |
| CNDP1 | EWVAIESDSVQPVPR (18) | Upregulated by at least 1.2 fold or 1.3 fold, or increased expression by at least 5%, at least 10%, at least 15% or at least 20% |
| F2 | ETAASLLQAGYK (20) | Downregulated by at least 1.2 fold, at least 1.4 fold, or at least 1.6 fold, or decreased expression by at least 10%, at least 20%, at least 40%, or at least 60% |
| GPX3 | QEPGENSEILPTLK (21) | Downregulated by at least 1.1 fold, 1.2 fold or decreased expression by at least 5%, at least 10%, or at least 15% |
| GPX3 | YVRPGGGFVPNFQLFEK (22) | Downregulated by at least 1.1 fold, 1.2 fold or at least 1.3 fold, or decreased expression by at least 5%, at least 15%, at least 20%, or at least 25% |
| GSN | AGALNSNDAFVLK (23) | Downregulated by at least 1.2 fold or at least 1.4 fold, at least 1.5 fold, or decreased expression by at least 10%, at least 20%, at least 30%, at least 35%, or at least 50% |
| GSN | QTQVSVLPEGGETPLFK (24) | Downregulated by at least 1.2 fold or at least 1.4 fold, at least 1.5 fold, or decreased expression by at least 10%, at least 20%, at least 30%, at least 35%, or at least 50% |
| GSN | TGAQELLR (25) | Downregulated by at least 1.2 fold, at least 1.4 fold, or at least 1.5 fold, or decreased expression by at least 10%, at least 20%, at least 40%, or at least 50% |
| KLKB1 | IAYGTQGSSGYSLR (30) | Downregulated by at least 1.1 fold or decreased expression by at least 5%, or at least 10% |
| KLKB1 | IYSGILNLSDITK (31) | Downregulated by at least 1.1 fold or decreased expression by at least 5%, or at least 10% |
| KNG1 | DIPTNSPELEETLTHTITK (32) | Downregulated by at least 1.2 fold or decreased expression by at least 5%, at least 10%, or at least 15% |
| KNG1 | TVGSDTFYSFK (33) | Downregulated by at least 1.2 fold or at least 1.3 fold, or decreased expression by at least 5%, at least 15%, at least 20%, or at least 25% |

TABLE 1 -continued

Diagnosis of T1DM by analysis of 22 proteins or 44 peptides as compared to healthy control

| Protein | Peptide (SEQ ID NO:) | Change in Expression Relative to Healthy Control to diagnose T1DM |
|---|---|---|
| LUM | FNALQYLR (34) | Upregulated by at least 1.2 fold, at least 1.4 fold, or at least 1.6 fold, or increased expression by at least 20%, at least 30% or at least 50% |
| LUM | ISNIPDEYFK (35) | Upregulated by at least 1.2 fold, at least 1.4 fold, or increased expression by at least 20%, at least 30% or at least 40% |
| LUM | NNQIDHIDEK (36) | Upregulated by at least 1.2 fold, at least 1.4 fold, or at least 1.5 fold, or increased expression by at least 20%, at least 30% or at least 50% |
| PGLYRP2 | AGLLRPDYALLGHR (37) | Downregulated by at least 1.2 fold, at least 1.3 fold, or at least 1.5 fold or decreased expression by at least 10%, at least 25%, or at least 50% |
| PGLYRP2 | PSLSHLLSQYYGAGVAR (38) | Downregulated by at least 1.2 fold, at least 1.3 fold, at least 1.5 fold, or at least 1.6 fold or decreased expression by at least 10%, at least 25%, or at least 50% |
| PGLYRP2 | TFTLLDPK (39) | Downregulated by at least 1.2 fold, at least 1.3 fold, or at least 1.5 fold or decreased expression by at least 10%, at least 25%, or at least 50% |
| PPBP | EESLDSDLYAELR (40) | Upregulated by at least 1.2 fold, at least 1.4 fold, or at least 1.6 fold, or increased expression by at least 20%, at least 30% or at least 50% |
| PPBP | NIQSLEVIGK (41) | Upregulated by at least 4 fold, at least 5 fold, at least 8 fold, or at least 10 fold, or increased expression by at least 200%, at least 400% or at least 800% |
| SERPINA6 | AQLLQGLGFNLTER (42) | Downregulated by at least 1.2 fold, at least 1.3 fold, or at least 1.4 fold or decreased expression by at least 10%, at least 25%, or at least 40% |
| SERPINA6 | EENFYVDETTVVK (43) | Downregulated by at least 1.1 fold, or decreased expression by at least 5% or at least 10% |
| SERPIND1 | SVNDLYIQK (44) | Downregulated by at least 1.2 fold, at least 1.3 fold, or at least 1.5 fold or decreased expression by at least 10%, at least 25%, or at least 50% |
| SERPIND1 | TLEAQLTPR (45) | Downregulated by at least 1.2 fold, at least 1.3 fold, or at least 1.5 fold or decreased expression by at least 10%, at least 25%, or at least 50% |
| SERPINF2 | LGNQEPGGQTALK (46) | Upregulated by at least 1.2 fold, at least 1.4 fold, or increased expression by at least 20%, at least 30% or at least 40% |
| SERPING1 | FQPTLLTLPR (47) | Upregulated by at least 1.5 fold, at least 2 fold, at least 2.6 fold, at least 5 fold, at least 7 fold, or increased expression by at least 100%, at least 200%, at least 250% or at least 500% |
| SERPING1 | LLDSLPSDTR (48) | Upregulated by at least 1.5 fold, at least 2 fold, at least 2.1 fold, at least 4 fold at least 5 fold or at least 7 fold, or increased expression by at least 75%, at least 150%, at least 200%, at least 400% or at least 600% |

TABLE 1 -continued

Diagnosis of T1DM by analysis of 22 proteins or 44 peptides as compared to healthy control

| Protein | Peptide (SEQ ID NO:) | Change in Expression Relative to Healthy Control to diagnose T1DM |
|---|---|---|
| SERPING1 | LVLLNAIYLSAK (49) | Upregulated by at least 1.2 fold, at least 1.4 fold, at least 1.6 fold, at least 2 fold or at least 3 fold or increased expression by at least 20%, at least 30%, at least 50%, at least 100% or at least 200% |
| SERPING1 | TNLESILSYPK (50) | Upregulated by at least 1.5 fold, at least 2 fold, at least 2.2 fold, at least 4 fold at least 5 fold or at least 7 fold, or increased expression by at least 75%, at least 150%, at least 200%, at least 400%, or at least 600% |
| TTR | AADDTWEPFASGK (51) | Downregulated by at least 1.2 fold, at least 1.4 fold, at least 1.5 fold, or at least 1.7 fold, or decreased expression by at least 10%, at least 20%, at least 50%, or at least 60% |
| TTR | GSPAINVAVHVFR (52) | Downregulated by at least 1.2 fold, at least 1.5 fold, or at least 1.7 fold, or decreased expression by at least 10%, at least 20%, at least 50%, or at least 60% |

TABLE 2

Diagnosis of T1DM by analysis of 5 proteins or 14 peptides as compared to healthy control

| Protein | Peptide (SEQ ID NO:) | Change in Expression Relative to Healthy Control to diagnose T1DM |
|---|---|---|
| GSN | AGALNSNDAFVLK (23) | Downregulated by at least 1.2 fold or at least 1.4 fold, or decreased expression by at least 10%, at least 20%, at least 30%, or at least 35% |
| GSN | QTQVSVLPEGGETPLFK (24) | Downregulated by at least 1.2 fold or at least 1.4 fold, or decreased expression by at least 10%, at least 20%, at least 30%, or at least 35% |
| GSN | TGAQELLR (25) | Downregulated by at least 1.2 fold or at least 1.5 fold, or decreased expression by at least 10%, at least 20%, at least 40%, or at least 50% |
| PGLYRP2 | AGLLRPDYALLGHR (37) | Downregulated by at least 1.2 fold, at least 1.3 fold, or at least 1.5 fold or decreased expression by at least 10%, at least 25%, or at least 50% |
| PGLYRP2 | PSLSHLLSQYYGAGVAR (38) | Downregulated by at least 1.2 fold, at least 1.3 fold, or at least 1.5 fold or decreased expression by at least 10%, at least 25%, or at least 50% |
| PGLYRP2 | TFTLLDPK (39) | Downregulated by at least 1.2 fold, at least 1.3 fold, or at least 1.5 fold or decreased expression by at least 10%, at least 25%, or at least 50% |
| PPBP | EESLDSDLYAELR (40) | Upregulated by at least 1.2 fold, at least 1.4 fold, or at least 1.6 fold, or increased expression by at least 20%, at least 30% or at least 50% |
| PPBP | NIQSLEVIGK (41) | Upregulated by at least 4 fold, at least 5 fold, or at least 8 fold, or increased expression by at least 200%, at least 400% or at least 800% |

TABLE 2-continued

Diagnosis of T1DM by analysis of 5 proteins or 14 peptides as compared to healthy control

| Protein | Peptide (SEQ ID NO:) | Change in Expression Relative to Healthy Control to diagnose T1DM |
|---|---|---|
| SERPING1 | FQPTLLTLPR (47) | Upregulated by at least 1.5 fold, at least 2 fold, or at least 2.6 fold, or increased expression by at least 100%, at least 200% or at least 250% |
| SERPING1 | LLDSLPSDTR (48) | Upregulated by at least 1.5 fold, at least 2 fold, or at least 2.1 fold, or increased expression by at least 75%, at least 150% or at least 200% |
| SERPING1 | LVLLNAIYLSAK (49) | Upregulated by at least 1.2 fold, at least 1.4 fold, or at least 1.6 fold, or increased expression by at least 20%, at least 30% or at least 50% |
| SERPING1 | TNLESILSYPK (50) | Upregulated by at least 1.5 fold, at least 2 fold, or at least 2.2 fold, or increased expression by at least 75%, at least 150% or at least 200% |
| TTR | AADDTWEPFASGK (51) | Downregulated by at least 1.2 fold, at least 1.5 fold, or at least 1.7 fold, or decreased expression by at least 10%, at least 20%, at least 50%, or at least 60% |
| TTR | GSPAINVAVHVFR (52) | Downregulated by at least 1.2 fold, at least 1.5 fold, or at least 1.7 fold, or decreased expression by at least 10%, at least 20%, at least 50%, or at least 60% |

TABLE 3

Diagnosis of T1DM by analysis of 3 proteins or 8 peptides as compared to healthy control

| Protein | Peptide (SEQ ID NO:) | Change in Expression Relative to Healthy Control to diagnose T1DM |
|---|---|---|
| PGLYRP2 | AGLLRPDYALLGHR (37) | Downregulated by at least 1.2 fold, at least 1.3 fold, or at least 1.5 fold or decreased expression by at least 10%, at least 25%, or at least 50% |
| PGLYRP2 | PSLSHLLSQYYGAGVAR (38) | Downregulated by at least 1.2 fold, at least 1.3 fold, or at least 1.5 fold or decreased expression by at least 10%, at least 25%, or at least 50% |
| PGLYRP2 | TFTLLDPK (39) | Downregulated by at least 1.2 fold, at least 1.3 fold, or at least 1.5 fold or decreased expression by at least 10%, at least 25%, or at least 50% |
| PPBP | NIQSLEVIGK (41) | Upregulated by at least 4 fold, at least 5 fold, or at least 8 fold, or increased expression by at least 200%, at least 400% or at least 800% |
| SERPING1 | FQPTLLTLPR (47) | Upregulated by at least 1.5 fold, at least 2 fold, or at least 2.6 fold, or increased expression by at least 100%, at least 200% or at least 250% |
| SERPING1 | LLDSLPSDTR (48) | Upregulated by at least 1.5 fold, at least 2 fold, or at least 2.1 fold, or increased expression by at least 75%, at least 150% or at least 200% |

TABLE 3-continued

Diagnosis of T1DM by analysis of 3 proteins or 8 peptides as compared to healthy control

| Protein Peptide (SEQ ID NO:) | Change in Expression Relative to Healthy Control to diagnose T1DM |
|---|---|
| SERPING1 LVLLNAIYLSAK (49) | Upregulated by at least 1.2 fold, at least 1.4 fold, or at least 1.6 fold, or increased expression by at least 20%, at least 30% or at least 50% |
| SERPING1 TNLESILSYPK (50) | Upregulated by at least 1.5 fold, at least 2 fold, or at least 2.2 fold, or increased expression by at least 75%, at least 150% or at least 200% |

Clinical Specimens

Appropriate specimens for use with the current disclosure in diagnosing or prognosing T1DM include any conventional clinical samples, for instance blood or blood-fractions (such as serum or plasma). In a specific example, the sample is a human plasma or serum sample processed for detecting T1DM-related biomarkers. Techniques for acquisition of such samples are well known in the art (for example see Schluger et al. *J. Exp. Med.* 176:1327-33, 1992, for the collection of serum samples). Serum or other blood fractions can be prepared in the conventional manner. For example, 5 µL to 1000 µl of serum can be used to screen for the presence of proteins, depending on the detection method used (e.g., immunoaffinity methods or targeted mass spectrometry). For discovery-based proteomics methods, more material is required (e.g., >100 µl serum), since immunodepletion is typically used to remove the majority of plasma protein mass, and subsequent sample processing, such as digestion or enrichment of specific peptides, will inherently incur sample losses.

For example, rapid DNA preparation can be performed using a commercially available kit (such as the InstaGene Matrix, BioRad, Hercules, Calif.; the NucliSens isolation kit, Organon Teknika, Netherlands. In one example, the DNA preparation method yields a nucleotide preparation that is accessible to, and amenable to, nucleic acid amplification. Similarly, RNA can be prepared using a commercially available kit (such as the RNeasy Mini Kit, Qiagen, Valencia, Calif.).

Once a sample has been obtained, the sample can be used directly, concentrated (for example by centrifugation or filtration), purified, amplified, treated with enzymes (e.g., proteases, such as trypsin), or combinations thereof. In particular examples, the sample is immunodepleted to remove proteins not of interest (e.g., proteins which need not be detected to practice the methods disclosed herein). In other particular examples, the sample is used without removing proteins not of interest (e.g., proteins which need not be detected to practice the methods disclosed herein), for example, the sample is not immunodepleted prior to analysis (e.g., no prior tryptic digestion of serum or plasma). In particular examples, the sample is processed such that the sample can be analyzed for the presence of T1DM-related molecules using mass spectrometry, such as capillary liquid chromatography-Fourier transform ion cyclotron resonance mass spectrometry of protein digests of human plasma and serum samples. In particular examples, the sample is processed such that the sample can be analyzed for the presence of T1DM-related molecules using mass spectrometry, such as capillary liquid chromatography-multiple reaction monitoring (or selected reaction monitoring) mass spectrometry (LC-MRM-MS) of protein digests of human plasma and serum samples. In some examples, data is analyzed using the accurate Mass and Time tag approach (AMT tag). In some examples, data is analyzed using statistical tools.

Output

In some embodiments, once a patient's diagnosis or prognosis is determined, an indication of that diagnosis or prognosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output.

For example, the output can be a molecular signature that is consistent with T1DM, or a molecular signature that is consistent with an absence of T1DM. Thus, in some examples, the output can be a diagnosis of T1DM or not.

In other examples, the output is a numerical value, such as an amount of T1DM-related molecule (such as those in Tables 1-3) in the sample, for example as compared to a control. In additional examples, the output is a graphical representation, for example, a graph that indicates the value (such as amount or relative amount) of T1DM-related molecule in the sample from the subject on a standard curve. In a particular example, the output (such as a graphical output) shows or provides a cut-off value or level that indicates a diagnosis of T1DM. In some examples, the output is communicated to the user, for example by providing an output via physical, audible, or electronic means (for example by mail, telephone, facsimile transmission, email, or communication to an electronic medical record).

The output can provide quantitative information (for example, an amount of T1DM-related molecule (such as those in Tables 1-3), for example relative to a control sample or value, or can provide qualitative information (for example, a diagnosis of T1DM). In additional examples, the output can provide qualitative information regarding the relative amount of T1DM-related molecule (such as those in Tables 1-3) in the sample, such as identifying presence of an increase in an amount of T1DM-related molecules (such as those in Tables 1-3) relative to a control, a decrease in an amount of T1DM-related molecules (such as those in Tables 1-3) relative to a control, or no change in an amount of T1DM-related molecules (such as those in Tables 1-3) relative to a control.

In some examples, the output is accompanied by guidelines for interpreting the data, for example, numerical or other limits that indicate the presence or absence of T1DM. The guidelines need not specify whether the patient from whom the sample was obtained has T1DM or not, although it may include such a diagnosis. The indicia in the output can, for example, include normal or abnormal ranges or a cutoff, which the recipient of the output may then use to interpret the results, for example, to arrive at a diagnosis or treatment plan. In other examples, the output can provide a recommended therapeutic regimen. In some examples, the test may include determination of other clinical information (such as determining the amount of one or more additional T1DM-related molecules in the sample).

Follow-Up Therapies

In some examples, the methods further include treatment for T1DM, if the sample is diagnosed as a T1DM or diagnosed as having an increased risk for developing T1DM.

In some embodiments, the disclosed methods of diagnosis include one or more of the following depending on the patient's diagnosis: a) prescribing a treatment regimen for the subject if the subject's determined diagnosis is positive for T1DM (such as treatment with insulin, with one or more immunosuppressive drugs, or combinations thereof); b) not prescribing a treatment regimen for the subject if the subject's determined diagnosis is negative for T1DM; or c) administering a treatment (such as treatment with one or more immunosuppressive drugs such as cyclosporine A, anti-CD3 antibodies or anti-CD20 antibodies) to the subject if the subject's determined diagnosis is positive for increased risk for developing T1DM. In an alternative embodiment, the method can include recommending one or more of (a)-(c). Thus, the disclosed methods can further include treating a subject for T1DM, if the sample from the subject is characterized as having T1DM.

Arrays for Detecting Expression

In particular examples, methods for detecting a change in expression or amount of the disclosed T1DM-related proteins, peptides, or nucleic acid molecules listed in Tables 6a or 6b use the arrays disclosed herein. Arrays can be used to detect the presence of molecules whose expression is upregulated or downregulated, for example using specific oligonucleotide probes or antibody probes. The arrays can be used to diagnose T1DM (for example to determine if a person has or is predisposed to developing the disease). In particular examples, the disclosed arrays can include nucleic acid molecules, such as DNA or RNA molecules, or antibodies.

Nucleic Acid Arrays

In one example, the array includes nucleic acid oligonucleotide probes that can hybridize to any combination of at least two of the T1DM genes encoding the proteins listed in Tables 6a or 6b, such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, or at least 52 or even all of the proteins or peptides listed in Table 6a or 6b. In particular examples, an array includes oligonucleotides that can recognize nucleic acid molecules encoding all 24 T1DM-associated proteins listed in Table 6a, all 5 T1DM-associated proteins listed in Table 6b, all 3 T1DM-associated proteins listed in Table 3, all 52 T1DM-associated peptides listed in Table 6a, all 14 T1DM-associated peptides listed in Table 6b, or all 8 T1DM-associated peptides listed in Table 3. Certain of such arrays (as well as the methods described herein) can further include T1DM-related molecules that are not listed in Tables 6a or 6b, such as internal controls (e.g., housekeeping genes such as one or more of β-actin, glyceraldehyde 3-phosphate dehydrogenase (GADPH), succinate dehydrogenase (SDHA), hypoxanthine phosphoribosyl transferase 1 (HRPTI), HBS1-like protein (HBS1L), a cyclophilin family member protein, and alpha haemoglobin stabilizing protein (AHSP)).

In one example, a set of oligonucleotide probes is attached to the surface of a solid support for use in detection of T1DM-associated sequences, such as those nucleic acid sequences (such as cDNA or mRNA) obtained from the subject. Additionally, if an internal control nucleic acid sequence is used (such as nucleic acid molecules obtained from a subject who does not have T1DM or is pre-diabetic) an oligonucleotide probe can be included to detect the presence of this control nucleic acid molecule.

The oligonucleotide probes bound to the array can specifically bind sequences obtained from the subject, or amplified from the subject (such as under high stringency conditions). Thus, sequences of use with the method are oligonucleotide probes that recognize T1DM-related sequences, such as gene sequences (or corresponding proteins) listed in Tables 6a or 6b. Such sequences can be determined by examining the sequences of the different species, and choosing oligonucleotide sequences that specifically anneal to a particular T1DM-related sequence (such as those listed in Tables 6a or 6b), but not others. One of skill in the art can identify other T1DM-associated oligonucleotide molecules that can be attached to the surface of a solid support for the detection of other T1DM-associated nucleic acid sequences.

The methods and apparatus in accordance with the present disclosure take advantage of the fact that under appropriate conditions oligonucleotides form base-paired duplexes with nucleic acid molecules that have a complementary base sequence. The stability of the duplex is dependent on a number of factors, including the length of the oligonucleotides, the base composition, and the composition of the solution in which hybridization is effected. The effects of base composition on duplex stability can be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mismatched duplexes may be substantially reduced.

The length of each oligonucleotide sequence employed in the array can be selected to optimize binding of target T1DM-associated nucleic acid sequences. An optimum length for use with a particular T1DM-associated nucleic acid sequence under specific screening conditions can be determined empirically. Thus, the length for each individual element of the set of oligonucleotide sequences including in the array can be optimized for screening. In one example, oligonucleotide probes are from about 20 to about 35 nucleotides in length or about 25 to about 40 nucleotides in length.

The oligonucleotide probe sequences forming the array can be directly linked to the support. Alternatively, the oligonucleotide probes can be attached to the support by non-T1DM-associated sequences such as oligonucleotides or other molecules that serve as spacers or linkers to the solid support. The oligonucleotide probes can further include one or more detectable labels, to permit detection of hybridization signals between the probe and a target sequence.

Protein Arrays

In another example, an array includes protein sequences (or a fragment of such proteins, or antibodies specific to such proteins or protein fragments), which include at least two of the T1DM-related proteins listed in any of Tables 1-3, such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, or at least 52 or even all of the proteins or peptides listed in Table 6a or 6b. In particular examples, an array includes antibodies that can recognize all 24 T1DM-associated proteins listed in Table 6a, all 5 T1DM-associated proteins listed in Table 6b, all 3 T1DM-associated proteins listed in Table 3, all 52 T1DM-associated peptides listed in Table 6a, all 14 T1DM-associated peptides listed in Table 6b, or all 8 T1DM-associated peptides listed in Table 3. Certain of such arrays (as well as the methods described herein) can further include molecules to detect T1DM-related proteins that are not listed in Tables 6a or 6b, such as internal controls (e.g., housekeeping genes such as beta-actin).

Antibodies specific for such proteins are commercially available, for example from Abcam (Cambridge, Mass.), Creative BioMart (Shirley, N.Y.), Antibodies-Online Inc. (Atlanta, Ga.), Santa Cruz Biotechnology (Santa Cruz, Calif.) or Epitomics (Burlingame, Calif.). For example sc-240782 or sc-240783 from Santa Cruz Biotechnology can be used to detect platelet basic protein (PPBP) or its various cleavage forms; ab81707 and ab54898 from Abcam or T1607 or 6602-1 from Epitomics can be used to detect plasma protease C1 inhibitor (SERPING1); and CAB-1033 MH or CABT-23684 MH from Creative BioMart (Shirley, N.Y.) or ABIN419582 from Antibodies-Online Inc. can be used to detect PGLYRP2.

The proteins or antibodies forming the array can be directly linked to a solid support. Alternatively, the proteins or antibodies can be attached to the support by spacers or linkers to the solid support. For example, the antibodies specific for the T1DM-related proteins described herein can be part of a lateral flow device.

Changes in expression of T1DM-related proteins can be detected using, for instance, a T1DM protein-specific binding agent, which in some instances is labeled with an agent that can be detected. In certain examples, detecting a change in protein expression includes contacting a protein sample obtained from the serum or plasma of a subject with a T1DM protein-specific binding agent (which can be for example present on an array); and detecting whether the binding agent is bound by the sample and thereby measuring the levels of the T1DM-related protein present in the sample. A difference in the level of an T1DM-related protein in the sample, relative to the level of a T1DM-related protein found an analogous sample from a subject who does not have T1DM or is pre-diabetic, in particular examples indicates whether the test subject has or is predisposed to developing T1DM.

Array Substrate

The solid support can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide or antibody thereto; amenability to "in situ" synthesis of biomolecules; being chemically inert such that at the areas on the support not occupied by the oligonucleotides or proteins are not amenable to non-specific binding, or when non-specific binding occurs, such materials can be readily removed from the surface without removing the oligonucleotides or proteins.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Particularly disclosed for preparation of arrays are biaxially oriented polypropylene (BOPP) films; in addition to their durability, BOPP films exhibit a low background fluorescence.

Substrates suitable for lateral flow devises can also be used.

In one example the solid support is a particle, such as a bead. Such particles can be composed of metal (e.g., gold, silver, platinum), metal compound particles (e.g., zinc oxide, zinc sulfide, copper sulfide, cadmium sulfide), non-metal compound (e.g., silica or a polymer), as well as magnetic particles (e.g., iron oxide, manganese oxide). In some examples the bead is a latex or glass bead. The size of the bead is not critical; exemplary sizes include 5 nm to 5000 nm in diameter. In one example such particles are about 1 μm in diameter.

In another example, the solid support is a bulk material, such as a paper, membrane, porous material, water immiscible gel, water immiscible ionic liquid, water immiscible polymer (such as an organic polymer), and the like. For example, the solid support can comprises a membrane, such as a semi-porous membrane that allows some materials to pass while others are trapped. In one example the membrane comprises nitrocellulose. In a specific example the solid support is part of a lateral flow device that includes one or more regions containing the sensors disclosed herein.

The solid support can be any format to which the molecule specific for the test agent (e.g., T1DM-associated molecule provided herein) can be affixed, such as microtiter plates, ELISA plates, test tubes, inorganic sheets, dipsticks, lateral flow devices, and the like. In one example the solid support is a microtiter plate. For example sensors can be affixed to the wells of a microtiter plate (for example wherein some wells can contain a sensor to detect target X, while other wells can contain a sensor to detect target Y; or several wells might include the same sensor, wherein multiple samples can be analyzed simultaneously). The test sample potentially containing a target of interest can be placed in the wells of a microtiter plate containing a sensor disclosed herein, and the presence of the target detected using the methods provided herein in. The microtiter plate format permits testing multiple samples simultaneously (together with controls) each in one or more different wells of the same plate; thus, permitting high-throughput analysis of numerous samples.

Each of the supports and devices discussed herein (e.g., ELISA, lateral flow device) can be, in some embodiments, formatted to detect multiple targets (e.g., two or more of the T1DM-associated molecules provided herein) by the addition of reagents specific for the other targets of interest. For example, certain wells of a microtiter plate can include molecules specific for the other targets of interest. Some lateral flow device embodiments can include secondary, tertiary or more capture areas containing molecules specific for the other targets of interest.

Array Formats

A wide variety of array formats can be employed in accordance with the present disclosure. One example includes a linear array of oligonucleotide or antibody bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185).

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein (e.g., antibody) sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create probe populations in parallel rows (corresponding in number to the number of channels in the delivery system) across the substrate. Following completion of synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

Oligonucleotides can be bound to a support (such as one made of polypropylene) by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the probes on the array include one or more labels, that permit detection of probe:target sequence (e.g., a T1DM-related molecule in Table 1) complexes.

Lateral Flow Device

In one example the array is a lateral flow device, which is an analytical device in the form of a test strip used in lateral flow chromatography, in which a sample fluid, such as one to be tested for the presence of a target agent (such as one or more T1DM-related molecules in Table 1), flows (for example by capillary action) through the strip (which is frequently made of bibulous materials such as paper, nitrocellulose, and cellulose). The test sample and any suspended target agent(s) can flow along the strip to a detection zone where the presence or absence of the one or more T1DM-related molecules in Tables 1-3 is detected, for example to indicate a presence, absence and/or quantity of the one or more T1DM-related molecules in Tables 1-3.

Numerous lateral flow analytical devices are known, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,368,876; 7,799,554; EP 0810436; and WO 92/12428; WO 94/01775; WO 95/16207; and WO 97/06439. The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810.

Lateral flow devices can in one example be a one-step lateral flow assay in which a sample fluid is placed in a sample or wicking area on a bibulous strip (though, non bibulous materials can be used, and rendered bibulous by applying a surfactant to the material), and allowed to migrate along the strip until the sample comes into contact with one or more reagents, that lead to the interaction between a T1DM-related molecule in Table 1 and a detector, such as a labeled antibody specific for the T1DM-related molecule.

In some examples, the strip includes multiple regions for detecting a plurality of T1DM-related molecules in the sample (for example in parallel lines or as other separate portions of the device). The test strips can also incorporate control indicators, which provide a signal that the test has adequately been performed, even if a positive signal indicating the presence (or absence) of a target is not achieved.

A lateral flow device can include a sample application area or wicking pad, which is where the fluid or liquid sample is introduced. In one example, the sample may be introduced to the sample application area by external application, as with a dropper or other applicator. In another example, the sample application area may be directly immersed in the sample, such as when a test strip is dipped into a container holding a sample. In yet another example, the sample may be applied, blotted, poured or expressed onto the sample application area.

A lateral flow device can include a reagent or conjugation pad, the region of a lateral flow device where reagents are immobilized, such as one or more antibodies specific for one or more of the T1DM-related molecules in Tables 1-3. A lateral flow device may have more than one conjugation area, for example, a "primary conjugation area," a "secondary conjugation area," and so on. Often different reagents are immobilized in the primary, secondary, or other conjugation areas. Multiple conjugation areas may have any orientation with respect to each other on the lateral flow substrate; for example, a primary conjugation area may be distal or proximal to a secondary (or other) conjugation area and vice versa. Alternatively, a primary conjugation area and a conjugation (or other) area may be oriented perpendicularly to each other such that the two (or more) conjugation areas form a cross or a plus sign or other symbol. For example, Apilux et al. (*Anal. Chem.* 82:1727-32, 2010), Dungchai et al. (*Anal. Chem.* 81:5821-6, 2009), and Dungchai et al. (*Analytica Chemica Acta* 674:227-33, 2010), provide exemplary lateral flow devices with a central sample area and one or more conjugation areas distal to the sample area, which provide independent test zones where independent reactions can occur (e.g., each test zone has a different reagents for detecting a particular test agent, and can further include one or more reaction pads where reactions can take place (for example interspersed between the reagent pads) and an absorption pad that receives the generated antibody-protein or antibody-peptide complex, wherein each absorption pad can be independently read by a PGM), for example that form a "Y", cloverleaf, or spoke-wheel pattern. The antibody-protein or antibody-peptide complex can be detected by detecting a label on the antibody, such as radioactive isotopes, co-factors, ligands, chemiluminescent or fluorescent agents, silver particles, gold particles, iron particles, copper particles, selenium particles, sulphur particles, tellurium particles, carbon particles, and protein-coupled dye sacs.

In one example, the lateral flow device contains at least two separate reagent areas (such as 2, 3, 4, 5, 6, 7, 8, 9, 10, 11, 12, 13, 14, 15 or more) can be used to detect a plurality of different T1DM-related molecules in Tables 1-3 in a single sample. Any liquid (such as a fluid biological sample) applied in the sample application area flows along a path of flow from the sample application area, through the reagent areas, to the absorption area. In one example where a lateral flow device can detect multiple targets, the device includes a single wicking pad or sample application area, and multiple conjugation or reagent pads, membranes or reaction pads, and absorption pads (such that one or more conjugation pads are associated with one or more particular membranes and an absorption pad). For example, each conjugation pad(s) can include a different reagents needed to detect a particular T1DM-related molecule in Tables 1-3.

Detection of Nucleic Acid and Protein Molecules

The samples obtained from the subject (for example a serum or plasma sample) can contain altered levels of one or more nucleic acids or proteins or peptides associated with T1DM, such as those listed in Tables 6a and 6b. Changes in expression or detected amounts can be detected to determine if a subject is predisposed to developing T1DM, or has T1DM. The present disclosure is not limited to particular methods of detecting proteins, peptides or nucleic acid molecules. Any method of detecting a nucleic acid molecule or protein can be used, such as physical or functional assays. For example, the level of gene expression can be measured and quantified utilizing methods well known in the art and those disclosed herein, such as Northern-Blots, RNase protection assays, nucleic acid or antibody probe arrays, quantitative PCR (such as TaqMan assays), dot blot assays, in-situ hybridization, or combinations thereof. In addition, proteins can be detected or measured using antibody probe arrays (such as a lateral flow device, such as a point-of-care device), quantitative spectroscopic methods (for example mass spectrometry, such as surface-enhanced laser desorption/ionization (SELDI)-based mass spectrometry or multiple reaction monitoring (MRM) based tandem mass spectrometry), or combinations thereof.

Methods for labeling nucleic acid molecules and proteins, as well as antibodies, so that they can be detected are well known. Examples of such labels include non-radiolabels and radiolabels. Non-radiolabels include, but are not limited to enzymes, chemiluminescent compounds, fluorophores, metal complexes, haptens, colorimetric agents, dyes, or combinations thereof. Radiolabels include, but are not limited to, $^{125}$I and $^{35}$S. Radioactive and fluorescent labeling methods, as well as other methods known in the art, are suitable for use with the present disclosure. In one example, the primers used to amplify the subject's nucleic acids are labeled (such as with biotin, a radiolabel, or a fluorophore). In another example, the amplified nucleic acid samples are end-labeled to form labeled amplified material. For example, amplified nucleic acid molecules can be labeled by including labeled nucleotides in the amplification reactions. In another example, nucleic acid molecules obtained from a subject are labeled, and applied to an array containing oligonucleotides. In a particular example, proteins obtained from a subject are labeled and subsequently analyzed, for example by applying them to an array.

For such procedures, a biological sample of the subject is assayed for an increase or decrease in expression of T1DM-related molecules, such as those listed in Tables 6a or 6b. Suitable biological samples include blood samples that contain DNA or RNA (including mRNA) or proteins. In a particular example, the sample is a serum or plasma sample that has been immunodepleted. In another particular example, the sample is a serum or plasma sample without immunodepletion.

The detection in the biological sample of increased or decreased expression in a plurality of T1DM-related nucleic acid molecules, such as those listed in Table 6a or 6b, can be achieved by methods known in the art. For example, increased or decreased expression of a T1DM-related molecule can be detected by measuring the cellular level of T1DM-related nucleic acid molecule-specific mRNA. mRNA can be measured using techniques well known in the art, including for instance Northern analysis, RT-PCR and mRNA in situ hybridization. Details of mRNA analysis procedures can be found, for instance, in provided examples and in Sambrook et al. (ed.), *Molecular Cloning: A Laboratory Manual,* 2nd ed., vol. 1-3, Cold Spring Harbor Laboratory Press, Cold Spring Harbor, N.Y., 1989.

Oligonucleotides specific to T1DM-related sequences can be chemically synthesized using commercially available machines. These oligonucleotides can then be labeled, for example with radioactive isotopes (such as $^{32}P$) or with non-radioactive labels such as biotin (Ward and Langer et al., *Proc. Natl. Acad. Sci. USA* 78:6633-57, 1981) or a fluorophore, and hybridized to individual DNA samples immobilized on membranes or other solid supports by dot-blot or transfer from gels after electrophoresis. These specific sequences are visualized, for example by methods such as autoradiography or fluorometric (Landegren et al., *Science* 242:229-37, 1989) or colorimetric reactions (Gebeyehu et al., *Nucleic Acids Res.* 15:4513-34, 1987).

Nucleic acid molecules isolated from blood samples can be amplified using routine methods to form nucleic acid amplification products. These nucleic acid amplification products can then be contacted with an oligonucleotide probe that will hybridize under stringent conditions with a T1DM-related nucleic acid. The nucleic acid amplification products which hybridize with the probe are then detected and quantified. The oligonucleotide probe can bind specifically to a nucleic acid molecule that encodes a protein listed in any of Tables 6a or 6b.

The nucleic acid molecules obtained from the subject that are associated with T1DM can be applied to a T1DM detection array under suitable hybridization conditions to form a hybridization complex. In particular examples, the nucleic acid molecules include a label. In one example, a pre-treatment solution of organic compounds, solutions that include organic compounds, or hot water, can be applied before hybridization (see U.S. Pat. No. 5,985,567, herein incorporated by reference).

Hybridization conditions for a given combination of array and target material can be optimized routinely in an empirical manner close to the $T_m$ of the expected duplexes, thereby maximizing the discriminating power of the method. Identification of the location in the array, such as a cell, in which binding occurs, permits a rapid and accurate identification of sequences associated with T1DM present in the amplified material (see below).

The hybridization conditions are selected to permit discrimination between matched and mismatched oligonucleotides. Hybridization conditions can be chosen to correspond to those known to be suitable in standard procedures for hybridization to filters and then optimized for use with the arrays of the disclosure. For example, conditions suitable for hybridization of one type of target would be adjusted for the use of other targets for the array. In particular, temperature is controlled to substantially eliminate formation of duplexes between sequences other than exactly complementary T1DM-associated sequences. A variety of known hybridization solvents can be employed, the choice being dependent on considerations known to one of skill in the art (see U.S. Pat. No. 5,981,185).

Once the nucleic acid molecules associated with T1DM from the subject have been hybridized with the oligonucleotides present in the T1DM detection array, the presence of the hybridization complex can be analyzed, for example by detecting the complexes.

Detecting a hybridized complex in an array of oligonucleotide probes has been previously described (see U.S. Pat. No. 5,985,567, herein incorporated by reference). In one example, detection includes detecting one or more labels present on the oligonucleotides, the sequences obtained from the subject, or both. In particular examples, developing includes applying a buffer. In one example, the buffer is sodium saline citrate, sodium saline phosphate, tetramethylammonium chloride, sodium saline citrate in ethylenediaminetetra-acetic, sodium saline citrate in sodium dodecyl sulfate, sodium saline phosphate in ethylenediaminetetra-acetic, sodium saline phosphate in sodium dodecyl sulfate, tetramethylammonium chloride in ethylenediaminetetra-acetic, tetramethylammonium chloride in sodium dodecyl sulfate, or combinations thereof. However, other suitable buffer solutions can also be used.

Detection can further include treating the hybridized complex with a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera (manufactured by Photometrics, Inc. of Tucson, Ariz.). In particular examples, these steps are not performed when fluorophores or radiolabels are used.

In particular examples, the method further includes quantification, for instance by determining the amount of hybridization.

Protein expression can be detected using any method known in the art, such as by detecting full-length proteins or portions thereof using antibodies, or using other methods such as mass spectrometry. The determination of increased or decreased T1DM-related protein levels, in comparison to such expression in a control (such as a subject who does not have T1DM or is prediabetic), is an alternative or supplemental approach to the direct determination of the expression level of T1DM-related nucleic acid sequences by the methods outlined above. The availability of antibodies specific to T1DM-related protein(s) facilitates the detection and quantification of such protein(s) by one of a number of immunoassay methods that are well known in the art, such as those presented in Harlow and Lane (*Antibodies, A Laboratory Manual*, CSHL, New York, 1988). In addition, if such antibodies are not available, methods of constructing antibodies are routine in the art.

Any standard immunoassay format (such as ELISA, Western blot, or RIA assay) can be used to measure T1DM-related protein levels. A comparison to control (e.g., subject who does not have T1DM) and an increase or decrease in T1DM-related peptide levels (such as an increase or decrease in any combination of at least 2, at least 3, at least 4, at least 5, or at least 10 proteins or peptides listed in Tables 1-3) is indicative of T1DM. Immunohistochemical techniques can also be utilized for protein detection and quantification. For example, a tissue sample can be obtained from a subject, and a section stained for the presence of a T1DM-related protein using the appropriate protein specific binding agents and any standard detection system (such as one that includes a secondary antibody conjugated to horseradish peroxidase). General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying T1DM-related proteins, a biological sample of the subject that includes cellular proteins can be used. Quantification of a T1DM-related protein or peptide can be achieved by immunoassay and the amount compared to levels of the protein found in cells from a subject who does not have T1DM or is prediabetic. A significant increase or decrease in the amount of one or more T1DM-related proteins in the serum or plasma (or other sample) of a subject compared to the amount of the same T1DM-related protein found in a normal sample is usually at least at a 1.1-fold, at least 1.2 fold, at least 1.5 fold, at least 2-fold, at least 3-fold, at least 4-fold, at least 8-fold, or greater increase or decrease. Substantial overexpression or underexpression of one or more T1DM-related protein(s) or peptides, such as two or more, can be indicative of the presence of T1DM or pre-diabetes.

In one example, a spectrometric method is utilized to detect or quantify an expression level of a target protein (such as those in Tables 1-3). Exemplary spectrometric methods include mass spectrometry, nuclear magnetic resonance spectrometry, and combinations thereof. In one example, mass spectrometry is used to detect the presence of a target protein (such as those in Tables 1-3) in a biological sample (see for example, Stemmann et al., *Cell* 107(6):715-26, 2001; Zhukov et al., "From Isolation to Identification: Using Surface Plasmon Resonance-Mass Spectrometry in Proteomics, Pharma-Genomics, March/April 2002).

A target protein (such as a T1DM-related protein or peptide) also can be detected by mass spectrometry assays coupled to immunaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of proteins separated by two-dimensional polyacrylamide gel electrophoresis (2D-PAGE) (Kiernan et al., *Anal. Biochem.*, 301: 49-56, 2002; Poutanen et al., *Mass Spectrom.*, 15: 1685-1692, 2001).

Quantitative mass spectroscopic methods, such as SELDI, can be used to analyze protein expression in a sample. In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. No. 5,719, 060; U.S. Pat. No. 6,897,072; and U.S. Pat. No. 6,881,586). SELDI is a solid phase method for desorption in which the analyte is presented to the energy stream on a surface that enhances analyte capture or desorption.

In one example, one or more of the T1DM-related peptides listed in Tables 6a or 6b are detected using MRM mass spectrometry or tandem mass spectrometry (such as LC-MRM-MS), for example by spiking one or more stable isotope peptides to be detected (such as one or more of those in Tables 6a or 6b, such as those in Table 2 or 3) into a test serum or plasma sample and detecting setting parameters for the specific detection and accurate quantification of the desired T1DM-related peptides.

Briefly, one version of SELDI uses a chromatographic surface with a chemistry that selectively captures analytes of interest, such as one or more those in Tables 1-3. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as those in Tables 1-3) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind a target protein (such as on or more of those in Tables 1-3). In other examples, the chromatographic surface consists essentially of, or consists of, antibodies that specifically bind a target protein (such as those in any of Tables 1-3). In some examples, the chromatographic surface includes antibodies that bind other molecules, such as housekeeping proteins.

In another example, antibodies are immobilized onto the surface using a bacterial Fc binding support. The chromatographic surface is incubated with a sample. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

Alternatively, the amount of target protein (such as a T1DM-related protein) can be determined using fluorescent methods. For example, Quantum dots (Qdots®) are useful in a growing list of applications including immunohistochemistry, flow cytometry, and plate-based assays, and may therefore be used in conjunction with this disclosure. Qdot® nanocrystals have unique optical properties including an extremely bright signal for sensitivity and quantitation; and high photostability for imaging and analysis. A single excitation source is needed, and a growing range of conjugates makes them useful in a wide range of cell-based applications. Qdot® Bioconjugates are characterized by quantum yields comparable to the brightest traditional dyes available. Additionally, these quantum dot-based fluorophores absorb 10-1000 times more light than traditional dyes. The emission from the underlying Qdot® quantum dots is narrow and symmetric, which means overlap with other colors is minimized, resulting in minimal bleed through into adjacent detection channels and attenuated crosstalk, in spite of the fact that many more colors can be used simultaneously. Standard fluorescence microscopes are an inexpensive tool for detecting Qdot® Bioconjugates. Since Qdot® conjugates are virtually photo-stable, time can be taken with the microscope to find regions of interest and adequately focus on the samples. Qdot® conjugates are useful any time bright photo-stable emission is required and are particularly useful in multicolor applications where only one excitation source/filter is available and minimal crosstalk among the colors is required.

For example, Qdot® fluorescent IHC can be performed with secondary antibodies, where the detection substrates are streptavidin-conjugated Qdot® conjugates. Image analysis can be performed by initially capturing image cubes on a spectral imaging camera (Cambridge Research Instruments, Woburn, Mass.). Excitation can be conducted with a UV (mercury) light source. The image cubes can then analyze. Briefly, image cubes can be retrieved in the application and data can be extracted and reported based on the pixel intensities of Qdot® conjugates expected to emit at 605 nm and 655 nm.

As an example, fluorescence can be measured with the multispectral imaging system Nuance™ (Cambridge Research & Instrumentation, Woburn, Mass.). As another example, fluorescence can be measured with the spectral imaging system SpectrView™ (Applied Spectral Imaging, Vista, Calif.). Multispectral imaging is a technique in which spectroscopic information at each pixel of an image is gathered and the resulting data analyzed with spectral image-processing software. For example, the Nuance system can take a series of images at different wavelengths that are electronically and continuously selectable and then utilized with an analysis program designed for handling such data. The Nuance system is able to obtain quantitative information from multiple dyes simultaneously, even when the spectra of the dyes are highly overlapping or when they are co-localized, or occurring at the same point in the sample, provided that the spectral curves are different. Many biological materials autofluoresce, or emit lower-energy light when excited by higher-energy light. This signal can result in lower contrast images and data. High-sensitivity cameras without multispectral imaging capability only increase the autofluorescence signal along with the fluorescence signal. Multispectral imaging can unmix, or separate out, autofluorescence from the sample and, thereby, increase the achievable signal-to-noise ratio.

Kits

The present disclosure provides for kits that can be used to diagnose T1DM, for example to determine if a subject has T1DM or has an increased predisposition to developing T1DM. Such kits allow one to determine if a subject has a differential expression in T1DM-related genes, such those listed in Tables 6a or 6b.

In one example the disclosed kits include binding molecules, such as oligonucleotide probes that selectively hybridize to, or antibodies that specifically bind to, T1DM-related molecules that are the target of the kit. In particular examples, the oligonucleotide probes or antibodies are attached to an array, such as a biochip, lateral flow device, or dipstick. Such an array can include other oligonucleotides or antibodies, for example to serve as negative or positive controls. In one example, the kit includes oligonucleotide probes or primers (or antibodies) that recognize any combination of at least two of the proteins or peptides in Tables 6a or 6b, such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, or all 52 of the T1DM-related molecules listed in any of Tables 6a or 6b. In one example, the kit includes oligonucleotide probes or primers (or antibodies) that recognize the proteins or peptides in Table 2 or 3.

In another example, the kit includes one or more of 1) stable isotope labeled peptides (in solid or solution form) for those peptides in Tables 6a or 6b, such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, or all 52 stable isotope labeled T1DM-related peptides listed in any of Tables 6a or 6b, such as the stable isotope labeled peptides for those peptides in Table 2 or 3; 2) a suitable HPLC column; and 3) materials for quantifying these peptides using LC-MRM-MS (e.g., see Table 5), such as TRAQ kits for amino acid analysis for hydrolysates, and iTRAQ reagents for protein quantification. Such a kit can be used to detect one or more of the T1DM-related peptides listed in Tables 6a or 6b, for example by spiking these stable isotope peptides into a test serum or plasma sample and detecting setting parameters for their specific detection and accurate quantification, for example using MRM mass spectrometry or tandem mass spectrometry.

The kit can further include one or more of a buffer solution, a conjugating solution for developing the signal of interest, or a detection reagent for detecting the signal of interest, each in separate packaging, such as a container. Kits can include instructions, for instance instructions that provide calibration curves or charts to compare with the determined (such as experimentally measured) values. For example, instructions can permit the tester to determine whether T1DM-related protein/peptide expression levels are elevated, reduced, or unchanged in comparison to a control sample. In some examples kits include materials for obtaining a sample, such as vials, cotton swabs, and needles.

Screening

The disclosure of 52 new T1DM-related peptides and 24 new T1DM-related proteins permits for screening for new T1DM therapeutics. For example, as shown in Tables 1-3, some T1DM-related proteins or peptides are upregulated (such as SERPING1, such as SEQ ID NOS: 47-50), while other T1DM-related proteins or peptides are downregulated (such as PGLYRP2, such as SEQ ID NOS: 37-39) in patients with T1DM. Thus, agents that correct the imbalance of one or more of these proteins/peptides can be identified. Such assays can be performed in vitro, ex vivo (for example using appropriate cell lines, such as a cell line (e.g., pancreatic β cells) in which cyclic AMP (cAMP) early repressor (ICER) Iγ overexpression is induced), or in vivo (for example in an animal model for T1DM, such as a pancreatectomized dog, a rodent treated with streptozotocin or alloxan, the non-obese diabetic mouse model, or a transgenic or knock-out animal, for review see Rees and Alcolado, *Diabet Med.* 22(4):359-70, 2005 herein incorporated by reference).

For example, a cell or animal model for T1DM is contacted (e.g., administered) with one or more test agents (such as proteins, antibodies, nucleic acids, or other small molecules) under conditions that permit the test agent to interact with the cell. Subsequently, the level of expression of one or more of the 52 T1DM-related peptides or 24 T1DM-related proteins disclosed herein is measured. In some examples, a baseline measurement of the one or more of the 52 T1DM-related peptides or 24 T1DM-related proteins disclosed herein is measured prior to adding the test agent, to obtain an expression value to which to compare the expression value after adding the one or more test agents. Test agents the correct the imbalance of the one or more proteins or peptides, that is decrease the level of expression of a protein or peptide that is upregulated in T1DM or increase the level of expression of a protein or peptide that is downregulated in T1DM, can be selected for further study. For example, test agents can first be screened in vitro or ex vivo, and then selected and tested again in vivo. In some examples, a test agent that decreases the level of expression of a protein or peptide that is upregulated in T1DM by at least 10%, at least 20%, at least 30%, at least 50%, at least 75%, at least 80%, or at least 90% is selected. In some examples, a test agent that increases the level of expression of a protein or peptide that is downregulated in T1DM by at least 10%, at least 20%, at least 30%, at least 50%, at least 75%, at least 80%, or at least 90% is selected.

In addition, the disclosure of 52 T1DM-related peptides and 24 T1DM-related proteins permits for methods of therapy management, by monitoring expression of one or more of the disclosed T1DM-related peptides/proteins. For example, as shown in Tables 1-3, some T1DM-related proteins or peptides are upregulated (such as SERPING1, such as SEQ ID NOS: 47-50), while other T1DM-related proteins or peptides are downregulated (such as PGLYRP2, such as SEQ ID NOS: 37-39) in patients with T1DM. Thus, screening expression levels of one or more of these proteins can serve as an indicator of the effectiveness of a T1DM therapy, and can assist a patient or physician in managing a patient's T1DM therapy (such as insulin therapy). For example, such a method can be used in combination with, or as an alternative, to glucose level monitoring. In one example, expression of one or more of the disclosed T1DM-related peptides/proteins is measured or determined in a patient's sample, for example in the course of insulin therapy. For example, the level or amount of expression of one or more of the 52 T1DM-related peptides or 24 T1DM-related proteins disclosed herein is measured. The ability of the therapy to correct the imbalance of one or more of these proteins/peptides can be identified is then determined. In some examples, a baseline measurement of the one or more of the 52 T1DM-related peptides or 24 T1DM-related proteins disclosed herein is measured or determined in the patient, to obtain an expression value to which to compare the expression value after treatment with the therapy. Therapy management is considered successful if the therapy corrects the imbalance of the one or more proteins or peptides, that is decrease the level of expression of a protein or peptide that is upregulated in T1DM or increase the level of expression of a protein or peptide that is down-regulated in T1DM, can be selected for further study. In some examples, a test agent that decreases the level of expression of a protein or peptide that is upregulated in T1DM by at least 10%, at least 20%, at least 30%, at least 50%, at least 75%, at least 80%, or at least 90% is selected. In some examples, a test agent that increases the level of expression of a protein or peptide that is downregulated in T1DM by at least 10%, at least 20%, at least 30%, at least 50%, at least 75%, at least 80%, or at least 90% is selected.

In addition, the disclosure of 52 T1DM-related peptides and 24 T1DM-related proteins permits for methods of identifying new pathways involved in T1DM. For example, expression of one or more the 52 T1DM-related peptides or 24 T1DM-related proteins can be significantly reduced or eliminated in a cell or veterinary subject using routine molecular biology methods, and the effect on particular signaling pathways determined. These newly identified signaling pathways then can be investigated for their involvement with T1DM, for example by monitoring expression levels of the disclosed T1DM markers.

In one example, the disclosed screening methods include measuring or determining expression levels of any combination of at least two of the proteins or peptides in Tables 6a or 6b, such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, or all 52 of the T1DM-related molecules listed in any of Tables 6a or 6b.

EXAMPLE 1

Materials and Methods

This example describes the materials and methods used for the experiments described in Examples 2-4 below.

Chemicals and Materials

All chemicals and peptide desalting SPE cartridges (Supelco Discovery DSC-18) were purchased from Sigma-Aldrich (St. Louis, Mo.), and the Micro-BCA protein assay kit was obtained from Pierce (Rockford, Ill.). Sequencing-grade trypsin was from Promega (Madison, Wis.). All solvents used were LC-grade or higher. Stable isotope-labeled standard (SIS) peptides with uniformly ($^{13}$C and $^{15}$N)-labeled arginine or lysine residues on C-termini and carboxymethyl modification of cysteine residues were custom synthesized by Thermo Fisher Scientific (Ulm, Germany) at the purity level of AQUA Basic (Purity >95%). The SIS peptides were received lyophilized and used as is without further purification. The amount of each SIS peptide was determined by the manufacture before lyophilization.

Human Serum and Plasma Samples

Human serum and plasma samples for discovery, verification and validation analyses were provided by the DASP program, which is conducted in accordance with the Human Subjects policies and regulations of the United States Centers for Disease Control & Prevention. Similarly, this work was approved by the Institutional Review Board (IRB) of the Pacific Northwest National Laboratory. All samples were received frozen on dry ice. The samples for verification were from 100 healthy control individuals (ages 18-28) and 50 patients diagnosed with T1DM (ages 10-29), with mixed ethnicities and genders in each group (Table 4). The patient samples were collected from donors within 14 days of starting insulin treatment. Because patient samples were collected at multiple sites worldwide, investigators contributing material to the DASP were not limited to a single blood collection and subsequent plasma or serum preparation protocol. An additional 20 blind samples were provided by the DASP to validate the findings (Table 7). Patient samples are from newly diagnosed type 1 diabetes patients, and control samples are from individuals who have self-reported no diabetes in themselves or their families. The blind samples were not decoded to the investigators until data analysis was complete and results were reported to the DASP.

Peptide Identification and Construction of the AMT Tag Database

In order to quantify as many peptides and proteins as possible in subsequent measurements, a comprehensive human plasma/serum accurate mass and time (AMT) tag database was created by combining data from previous studies,[40,41] including a previous proteomics study of a DASP sample subset.[17] The AMT tag approach has been previously reviewed in detail.[25,31] To augment the contents of this database, further immunoaffinity subtraction of plasma/serum samples of type 1 diabetic patients from a full DASP sample set was performed. Briefly, aliquots of each patient serum or plasma sample (n=50) were pooled, and the pooled sample was then subjected to immunoaffinity subtraction using a SuperMix LC2 immunodepletion system (Sigma, St Louis, Mo.) coupled with an Agilent 1100 series HPLC system as described previously.[47,48] The flow-through (low abundance proteins) fractions were collected, pooled, and then concentrated in Amicon Ultra-15 concentrators (Millipore, Billerica, Mass.) with MWCO of 3 kDa, followed by a buffer exchange to 50 mM $NH_4HCO_3$ in the same unit according to the manufacturer's instructions. As reported previously, sample proteins were next sequentially denatured, reduced, alkylated, and digested with trypsin; the peptide mixtures were then cleaned up with $C_{18}$ SPE cartridges and fractionated using strong cation exchange chromatography.[25] A total of 30 peptide fractions were collected and analyzed in duplicate using a custom-built 4-column nanocapillary LC system coupled online to a linear ion-trap mass spectrometer (LTQ; Thermo Fisher). Peptides were separated on capillary columns (75 µm×65 cm) packed in-house with 3 µm Jupiter $C_{18}$ particles (Phenomenex, Torrence, Calif.).[49] The LTQ was operated in data-dependent MS/MS mode, during which a full MS scan was followed by 10 MS/MS scan events.

The SEQUEST search algorithm was used to match the MS/MS fragmentation spectra with sequences from the IPI human protein database (Version 3.39); static carbamidomethylation of cysteine and dynamic oxidation of methionine were used for the database search. Database-matched results were filtered using criteria based on the cross correlation score (Xcorr), delta correlation (ΔCn) values, trypsin cleavage rules and charge states to limit false positive identifications to ~1% at the peptide level using the decoy database approach.[25] Peptides passing these filter criteria were added to the AMT tag database. The final plasma AMT tag database contained 18,157 human plasma peptides available for matching to subsequent LC-FTICR MS datasets (see below). The peptide elution times from each LC-MS/MS analysis were normalized to a range of 0 to 1 using a predictive peptide LC normalized elution time (NET) model and linear regression, as previously reported.[50] A NET average and standard deviation were assigned to each identified peptide if the same peptide was observed in multiple analyses, and both calculated monoisotopic masses and observed NETs of identified peptides were included in the AMT tag database.

Quantitative Global Proteomics Analyses

Aliquots of each individual control and patient serum/plasma sample were pooled to form 10 pooled control and 10 pooled patient samples, with 5 individuals comprising each pool. Each pooled sample was subjected to immunoaffinity subtraction using the SuperMix immunodepletion system, as described above, with the exception that both the flow-through (low abundance proteins) and bound (high abundance proteins) fractions were collected separately and subjected to tryptic digestion and clean-up, as described above. Peptides from each pooled sample were then analyzed in duplicate using the same nanocapillary LC system described above, which was coupled to a 9.4 Tesla FTICR MS (Bruker Daltonics, Billerica, Mass.) via an electrodynamic ion funnel. The temperature of the heated capillary and the ESI voltage were 200° C. and 2.2 kV, respectively. The FTICR MS was operated to only collect high resolution MS data.

LC-FTICR MS datasets were processed using the PRISM Data Analysis system,[51] a series of software tools (e.g., Decon2LS, VIPER; freely available at ncrr.pnl.gov/software/) developed in-house. Decon2LS functions to deisotope the raw MS data, providing the monoisotopic mass, charge state and intensity of the major peaks in each MS spectrum.[52] The data were then examined in a 2D fashion to identify "features" using VIPER;[53] each feature has a median monoisotopic mass, central NET, and abundance estimate computed by summing the intensities of the MS peaks that comprise the entire LC-FTICR MS feature. To facilitate identification and quantification across multiple datasets, the detected features in each dataset (referring to data from a single LC-FTICR MS analysis) were aligned against the peptides within the AMT tag database using the LCMSWARP algorithm.[54] This is accomplished by comparing the measured monoisotopic masses and NETs of the detected features to the calculated monoisotopic masses and observed NETs of each of the peptides in the AMT tag database within search tolerances of ±3 ppm and ±0.02 NET for monoisotopic mass and elution time, respectively. This peak-matching process gave an initial list of peptide identifications for each individual dataset; in addition, all peptides were required to be observed in at least 50% of LC-FTICR MS datasets in each disease state.

DAnTE[55] was then used for quantitative and statistical analysis. Briefly, the matrix of peptide abundances from all LC-FTICR MS analyses was log 2 transformed, and then normalized globally using a central tendency algorithm[56] to variations in the data due to amount of sample loaded onto the LC column and ionization efficiency. For each peptide, a t test was performed between the samples in the control and patient groups, and only peptides with p values less than 0.05 were considered as significantly changed. To facilitate visualization of quantitative changes in peptide abundances across all 20 samples, the data were Z-score transformed prior to loading in the open-source tool TIGR Multiexperiment Viewer (MEV).[57]

Selection of Peptide Targets for MRM Verification

The above processing and analysis of the global quantitative proteomics data resulted in the identification of 24 candidate protein biomarkers of T1DM, the peptides of which were screened to remove those with the following characteristics: 1) non-tryptic; 2) greater than 20 amino acids long; 3) shorter than 7 amino acids; and 4) containing methionine.[27] In addition, an attempt was made to remove peptides that contained cysteine or other known post-translational modification sites. The best-scoring tandem mass spectra for each peptide identified in the global proteomics data were manually reviewed using Mass Analyzer[58] and the peptide sequence fragmentation modeling tool in Molecular Weight Calculator (omics.pnl.gov/software/MWCalculator.php) to select the precursor and associated top 6 most intense fragment ions (i.e., MRM transitions). A tryptic digest (0.4 µg/µL) of a pooled serum sample from healthy subjects was used to screen for the detectabilities and specificities (i.e., whether there are other peptides co-eluting with the target peptides that share the same transition events) of these transitions in a complex matrix using our LC-MRM/MS platform. The collision energies (CE) used to fragment each precursor were calculated from the following equations: for 2+ precursors, CE=0.034 m/z+3.314 and for 3+ precursors, CE=0.044 m/z+3.314, where m/z is the mass/charge value of the precursor.[28] Only those peptides having relatively high s/n and few matrix interferences were retained for the next round of screening. After two additional rounds of screening with lower performing ions pairs dropped from further consideration, all remaining peptides showed good detectability and specificity. The stable isotope-labeled versions of these peptides were then synthesized and used for setting up the LC-MRM/MS assays and for spiking into each sample for verification of candidate biomarkers.

LC-MRM/MS Assay Set-Up

Because the SIS and endogenous peptides co-elute on the LC column and have the same ionization efficiency and fragmentation behavior under collision-induced dissociation, the SIS peptides were used to optimize the detection parameters of the endogenous peptides. Briefly, the synthetic SIS peptides were individually dissolved in 0.1% formic acid/$CH_3CN$ (50:50, v/v) and then infused to a triple quadrupole mass spectrometer (TSQ; ThermoFisher) to optimize their collision energies and to verify their MRM transitions selected during the screening process. The SIS peptides were then individually spiked into serum tryptic digests, and through isotope dilution experiments using LC-MRM/MS, their retention times and best single MRM transitions were determined for use in the final assay. The retention time information from all peptides was used to set up a segmented MRM/MS method, such that all peptide targets could be monitored in the final multiplexed LC-MRM/MS assay. The linear dynamic ranges of the SIS peptides were also determined in these measurements.

Preparation of Concentration-Balanced SIS Peptide Mixture

Because of the large variations in endogenous levels of each peptide, their different ionization efficiencies and different linear dynamic ranges in quantification, the concentrations of spiked SIS peptides were individually adjusted to match the levels of the endogenous peptides in order to provide more accurate quantification.[27] Therefore, serum samples from 10 healthy subjects were pooled and tryptically digested to achieve a final peptide concentration of 0.5 µg/µL, which was used to titrate each SIS peptide to determine a concentration that would result in a SIS peptide peak area within a factor of 10 of that of the endogenous peptide. SIS peptides with optimized concentrations were then mixed in equal volumes to create a concentration-balanced mixture. Prior to spiking SIS peptides into each individually digested DASP sample to accurately quantify the endogenous peptides, the volume of SIS peptide mixture for spiking and the volume of serum/plasma sample to use for tryptic digestion were further optimized before the final processing of the full cohort.

Preparation of Serum Tryptic Digests

Samples were randomized prior to digestion to minimize the bias from sample handling. Then 5 µL of each whole serum sample (~400 µg of proteins measured by BCA assay) was diluted with 45 µL of 8 M urea. Denatured samples were reduced with 10 mM of dithiothreitol at 37° C. for 1 h, and then the reduced samples were alkylated with 40 mM iodoacetamide at room temperature for 1 h in the dark. Samples were then diluted with 50 mM $NH_4HCO_3$ (pH 8.1) to reduce the urea concentration to 0.8 M, followed by addition of 1 M $CaCl_2$ solution to a final concentration of 1 mM and trypsin in the ratio of 1:50 enzyme:substrate (w/w). Digestion was carried out overnight at 37° C.

Samples were acidified by adding 20% formic acid to a final concentration of 1% formic acid to stop the digestion. Then 15 µL of a concentration-balanced mixture of SIS peptides (in 0.1% formic acid) was added to each serum digest. Samples were then desalted on $C_{18}$ SPE cartridges (50 mg) and eluted peptides were dried down and reconstituted with 0.1% formic acid. The final concentration of the peptide mixture was adjusted to 0.5 µg/µL before it was subjected to LC-MRM/MS analysis. Sample digestion in the target peptide screening process was the same except that no acidification of sample and no addition of SIS peptide mixture were performed after the tryptic digestion step.

LC-MRM/MS Analysis of Serum/Plasma Digests

A nanoACQUITY LC system (Waters, Milford, Mass.) equipped with a BEH130 $C_{18}$ capillary UPLC column (100 µm×100 mm, 1.7 µm particle size) was used for separation of tryptic digests. A Symmetry $C_{18}$ trap column (180 µm×20 mm, 5.0 µm particle size) was attached before the analytical column for faster loading and on-line desalting of samples. One µL of each sample was loaded onto the trap column at 15 µL/min with 99.5% mobile phase A (see following) for 1 min before the start of gradient LC separation. The LC flow rate was set at 0.40 µL/min with the following mobile phases: A, 0.1% FA in water; B, 0.1% FA in acetonitrile. The following gradient was used: 0 min, 0.5% B; 0.5 min, 10% B; 4 min, 15% B; 25 min, 25% B; 36 min, 38.5% B; 37 to 41 min, 95% B; 42 min, 10% B; 43 to 60 min, 0.5% B. The effluent from the LC column was ionized using a spray voltage of 2400 V and detected by a triple quadrupole mass spectrometer (TSQ Vantage; Thermo Fisher Scientific). Other acquisition parameters were: collision gas pressure of 1.5 mTorr; scan width of 0.002 m/z; scan time of 0.015 s and peak width of 0.7 for both Q1 and Q3.

MRM Data Processing and Statistical Analysis

The acquired datasets were imported into Skyline.[59] Peak area integration was manually reviewed, then the peak area ratios between endogenous and SIS peptides and other peptide identification information were exported in tabular comma separated value (csv) format, using a customized Skyline format. Further statistical analysis was performed on the csv formatted data matrix. DAnTE was used to perform Pearson correlation, principle component (PCA) and partial least squares (PLS) analysis to check outlier samples. The peak area ratio distribution was also tested for normality using a Shapiro-Wilks test as implemented in DAnTE.[55] Because peptide ratios for the majority of peptides were not normally distributed, the non-parametric Mann-Whitney U-test was used to determine significance. This and the fold change calculations between control and patient groups were all functions of DAnTE. Sigmaplot (version 11.0) was used for receiver operator characteristic (ROC) curve analysis and for drawing box-whisker plots and bar charts. ROC curve analysis was used to evaluate the performance of each peptide assay in discriminating disease from control. The area under the curve (AUC) with 95% Confidence Interval was calculated assuming a non-parametric distribution. An AUC of 1.00 would indicate the peptide achieved 100% accuracy in identifying disease, and an AUC of 0.50 would indicate that the assignment of disease/control is entirely random.

To facilitate the identification of samples in the blind group, the cut-off value of peak area ratio corresponding to sensitivity at 90% specificity ($AS_{90}$) was obtained from the sensitivity and specificity report of ROC curve analysis for each peptide, and it was used as a threshold to classify the blind samples into control and disease. Then the sensitivity for each peptide assay was calculated as the percentage of sera from patients in the blind samples reported as positive using the cut-off value at $AS_{90}$, and the specificity of this peptide assay was calculated as the percentage of control sera reported as negative using the same threshold. Calculation of endogenous concentration of each peptide/protein was based on the amount of SIS peptide spike and the average peak area ratio as measured in endogenous/SIS peptide.

EXAMPLE 2

Discovery of Protein Markers and Development of Surrogate Peptide Assays

The DASP cohort samples contain blood serum and plasma samples from 100 control and 50 diabetic individuals (Table 4 contains detailed clinical parameters).

TABLE 4

Clinical data for DASP verification cohort (100 control and 50 type 1 diabetic patients). Sample race, gender, age, and the results of the three autoantibody assays are shown as provided by the DASP. Protein concentration was measured by BCA assay and classification of samples as serum or plasma was performed using the method of Gonzalez et al.[34]

| Sample ID | Race | Gender | Age | % of Assays > med AUC Designating Positive For GAD in DASP 2005 | % of Assays > med AUC Designating Positive For IA2 in DASP 2005 | % of Assays > med AUC Designating Positive For IAA in DASP 2005 | Specimen Type Predicted by Median of c49D2 | Total [Protein] Measured by BCA assay (ug/ul) |
|---|---|---|---|---|---|---|---|---|
| Control 1 | Caucasian | Male | 21 | 46.15 | 8.00 | 0.00 | Serum | 133.0 |
| Control 2 | Caucasian | Male | 20 | 0.00 | 0.00 | 0.00 | Serum | 147.7 |
| Control 3 | Caucasian | Male | 19 | 0.00 | 0.00 | 0.00 | Serum | 106.6 |
| Control 4 | Caucasian | Male | 19 | 0.00 | 0.00 | 0.00 | Serum | 132.7 |
| Control 5 | Caucasian | Male | 20 | 0.00 | 0.00 | 0.00 | Serum | 130.0 |
| Control 6 | Caucasian | Male | 20 | 11.54 | 0.00 | 0.00 | Serum | 122.3 |
| Control 7 | Caucasian | Male | 18 | 92.31 | 12.00 | 6.67 | Serum | 136.4 |
| Control 8 | Caucasian | Male | 20 | 0.00 | 4.00 | 0.00 | Serum | 129.4 |
| Control 9 | Caucasian | Male | 20 | 0.00 | 0.00 | 0.00 | Plasma | 137.2 |
| Control 10 | Caucasian | Male | 18 | 0.00 | 0.00 | 0.00 | Serum | 109.0 |
| Control 11 | Caucasian | Male | 18 | 0.00 | 8.00 | 6.67 | Serum | 102.0 |
| Control 12 | Caucasian | Male | 19 | 0.00 | 0.00 | 0.00 | Serum | 63.9 |
| Control 13 | Africa American | Male | 20 | 19.23 | 4.00 | 0.00 | Serum | 51.1 |
| Control 14 | Africa American | Male | 19 | 0.00 | 0.00 | 0.00 | Serum | 101.3 |
| Control 15 | Africa American | Male | 21 | 0.00 | 0.00 | 0.00 | Serum | 69.7 |
| Control 16 | Caucasian | Male | 24 | 0.00 | 0.00 | 0.00 | Serum | 58.3 |
| Control 17 | Caucasian | Male | 23 | 0.00 | 0.00 | 6.67 | Serum | 75.7 |
| Control 18 | Caucasian | Male | 24 | 0.00 | 0.00 | 0.00 | Serum | 78.3 |
| Control 19 | Hispanic | Female | 26 | 0.00 | 4.00 | 0.00 | Serum | 76.9 |
| Control 20 | Caucasian | Male | 26 | 0.00 | 0.00 | 0.00 | Serum | 79.6 |
| Control 21 | Caucasian | Male | 23 | 0.00 | 0.00 | 0.00 | Serum | 98.8 |
| Control 22 | Caucasian | Male | 25 | 0.00 | 4.00 | 0.00 | Serum | 114.8 |
| Control 23 | Africa American | Male | 22 | 3.85 | 0.00 | 0.00 | Serum | 131.8 |
| Control 24 | Caucasian | Male | 28 | 0.00 | 0.00 | 0.00 | Serum | 116.2 |
| Control 25 | Caucasian | Female | 26 | 0.00 | 0.00 | 0.00 | Serum | 102.4 |
| Control 26 | Caucasian | Male | 18 | 0.00 | 4.00 | 0.00 | Serum | 135.8 |
| Control 27 | Caucasian | Female | 18 | 0.00 | 0.00 | 0.00 | Serum | 136.1 |
| Control 28 | Caucasian | Female | 18 | 11.54 | 0.00 | 6.67 | Serum | 101.0 |
| Control 29 | Caucasian | Female | 19 | 0.00 | 0.00 | 0.00 | Serum | 97.3 |
| Control 30 | Caucasian | Female | 18 | 15.38 | 4.00 | 0.00 | Serum | 134.6 |
| Control 31 | Caucasian | Female | 20 | 0.00 | 4.00 | 0.00 | Serum | 116.8 |
| Control 32 | Caucasian | Female | 19 | 0.00 | 0.00 | 0.00 | Serum | 103.5 |
| Control 33 | Caucasian | Female | 18 | 0.00 | 0.00 | 0.00 | Serum | 114.5 |
| Control 34 | Caucasian | Female | 18 | 0.00 | 4.00 | 0.00 | Serum | 121.4 |
| Control 35 | Caucasian | Female | 19 | 0.00 | 8.00 | 6.67 | Serum | 122.9 |
| Control 36 | Caucasian | Female | 19 | 0.00 | 4.00 | 0.00 | Serum | 122.3 |
| Control 37 | Caucasian | Female | 20 | 0.00 | 0.00 | 0.00 | Serum | 92.2 |
| Control 38 | Hispanic | Female | 20 | 7.69 | 0.00 | 0.00 | Serum | 101.7 |
| Control 39 | Hispanic | Female | 19 | 19.23 | 0.00 | 6.67 | Serum | 112.9 |
| Control 40 | Hispanic | Female | 19 | 3.85 | 0.00 | 0.00 | Plasma | 121.0 |
| Control 41 | Caucasian | Female | 23 | 0.00 | 0.00 | 0.00 | Serum | 122.7 |

TABLE 4-continued

Clinical data for DASP verification cohort (100 control and 50 type 1 diabetic patients).
Sample race, gender, age, and the results of the three autoantibody assays are shown as
provided by the DASP. Protein concentration was measured by BCA assay and classification of
samples as serum or plasma was performed using the method of Gonzalez et al.[34]

| Sample ID | Race | Gender | Age | % of Assays > med AUC Designating Positive For GAD in DASP 2005 | % of Assays > med AUC Designating Positive For IA2 in DASP 2005 | % of Assays > med AUC Designating Positive For IAA in DASP 2005 | Specimen Type Predicted by Median of c49D2 | Total [Protein] Measured by BCA assay (ug/ul) |
|---|---|---|---|---|---|---|---|---|
| Control 42 | Caucasian | Female | 24 | 3.85 | 0.00 | 0.00 | Serum | 76.9 |
| Control 43 | Caucasian | Female | 22 | 0.00 | 4.00 | 13.33 | Serum | 120.6 |
| Control 44 | Caucasian | Female | 22 | 0.00 | 0.00 | 0.00 | Serum | 87.7 |
| Control 45 | Caucasian | Female | 25 | 0.00 | 0.00 | 0.00 | Serum | 108.7 |
| Control 46 | Caucasian | Female | 22 | 0.00 | 4.00 | 0.00 | Serum | 110.0 |
| Control 47 | Hispanic | Female | 22 | 0.00 | 0.00 | 0.00 | Serum | 106.6 |
| Control 48 | Caucasian | Female | 21 | 0.00 | 4.17 | 0.00 | Serum | 53.5 |
| Control 49 | Caucasian | Male | 18 | 0.00 | 0.00 | 0.00 | Serum | 98.6 |
| Control 50 | Africa American | Female | 19 | 0.00 | 0.00 | 0.00 | Serum | 111.5 |
| Control 51 | Black | Female | 20 | 0.00 | 0.00 | 0.00 | Serum | 102.1 |
| Control 52 | Black | Male | 19 | 0.00 | 0.00 | 0.00 | Serum | 128.8 |
| Control 53 | Black | Male | 19 | 26.92 | 0.00 | 0.00 | Serum | 175.8 |
| Control 54 | White | Female | 19 | 0.00 | 0.00 | 0.00 | Serum | 143.7 |
| Control 55 | White | Male | 18 | 0.00 | 0.00 | 0.00 | Serum | 126.0 |
| Control 56 | White | Male | 18 | 0.00 | 0.00 | 0.00 | Serum | 142.4 |
| Control 57 | White | Male | 19 | 0.00 | 0.00 | 26.67 | Serum | 132.8 |
| Control 58 | White | Male | 19 | 0.00 | 0.00 | 6.67 | Serum | 126.8 |
| Control 59 | White | Female | 19 | 0.00 | 0.00 | 0.00 | Serum | 91.0 |
| Control 60 | White | Female | 21 | 0.00 | 0.00 | 6.67 | Serum | 98.8 |
| Control 61 | | | | | | | Serum | 97.4 |
| Control 62 | White | Male | 20 | 0.00 | 0.00 | 0.00 | Serum | 142.3 |
| Control 63 | White | Male | 20 | 0.00 | 0.00 | 0.00 | Serum | 100.7 |
| Control 64 | White | Male | 19 | 0.00 | 4.00 | 0.00 | Serum | 120.1 |
| Control 65 | White | Male | 18 | 0.00 | 0.00 | 0.00 | Serum | 94.3 |
| Control 66 | White | Male | 19 | 0.00 | 4.00 | 6.67 | Serum | 110.5 |
| Control 67 | White | Male | 21 | 0.00 | 0.00 | 0.00 | Serum | 130.0 |
| Control 68 | White | Male | 21 | 0.00 | 0.00 | 0.00 | Serum | 82.0 |
| Control 69 | White | Male | 21 | 0.00 | 0.00 | 0.00 | Serum | 98.5 |
| Control 70 | White | Male | 19 | 0.00 | 0.00 | 0.00 | Serum | 140.0 |
| Control 71 | Black | Male | 20 | 0.00 | 0.00 | 0.00 | Serum | 112.9 |
| Control 72 | Black | Male | 27 | 0.00 | 0.00 | 0.00 | Serum | 92.0 |
| Control 73 | Black | Male | 18 | 0.00 | 0.00 | 0.00 | Serum | 123.9 |
| Control 74 | White | Male | 24 | 3.85 | 0.00 | 0.00 | Serum | 134.2 |
| Control 75 | White | Male | 23 | 3.85 | 0.00 | 20.00 | Serum | 111.6 |
| Control 76 | White | Male | 22 | 0.00 | 0.00 | 0.00 | Serum | 130.3 |
| Control 77 | White | Male | 23 | 0.00 | 0.00 | 6.67 | Serum | 89.3 |
| Control 78 | Black | Female | 22 | 0.00 | 0.00 | 0.00 | Serum | 143.7 |
| Control 79 | White | Female | 19 | 0.00 | 0.00 | 6.67 | Serum | 143.3 |
| Control 80 | White | Female | 18 | 0.00 | 0.00 | 0.00 | Serum | 111.5 |
| Control 81 | White | Female | 20 | 0.00 | 0.00 | 0.00 | Serum | 114.5 |
| Control 82 | White | Female | 20 | 0.00 | 0.00 | 0.00 | Serum | 82.7 |
| Control 83 | White | Female | 21 | 30.77 | 8.00 | 6.67 | Serum | 128.1 |
| Control 84 | White | Female | 19 | 0.00 | 0.00 | 40.00 | Serum | 125.7 |
| Control 85 | White | Female | 20 | 0.00 | 4.00 | 0.00 | Serum | 94.4 |
| Control 86 | White | Female | 18 | 30.77 | 0.00 | 0.00 | Serum | 77.9 |
| Control 87 | White | Female | 20 | 0.00 | 0.00 | 0.00 | Serum | 120.6 |
| Control 88 | White | Female | 20 | 0.00 | 0.00 | 0.00 | Serum | 90.1 |
| Control 89 | White | Female | 27 | 0.00 | 0.00 | 0.00 | Serum | 106.2 |
| Control 90 | Black | Female | 20 | 3.85 | 0.00 | 0.00 | Serum | 81.0 |
| Control 91 | Black | Female | 21 | 0.00 | 0.00 | 0.00 | Serum | 155.2 |
| Control 92 | White | Female | 24 | 0.00 | 4.00 | 0.00 | Serum | 98.8 |
| Control 93 | White | Female | 23 | 0.00 | 0.00 | 0.00 | Serum | 106.4 |
| Control 94 | White | Female | 22 | 3.85 | 0.00 | 0.00 | Serum | 115.0 |
| Control 95 | White | Female | 22 | 0.00 | 0.00 | 0.00 | Serum | 139.8 |
| Control 96 | White | Female | 22 | 0.00 | 0.00 | 0.00 | Serum | 142.7 |
| Control 97 | Hispanic | Female | 26 | 3.85 | 0.00 | 0.00 | Serum | 155.7 |
| Control 98 | White | Female | 20 | 0.00 | 0.00 | 0.00 | Serum | 145.4 |
| Control 99 | White | Female | 18 | 3.85 | 0.00 | 0.00 | Serum | 161.4 |
| Control 100 | White | Male | 23 | 0.00 | 0.00 | 0.00 | Serum | 83.4 |
| Patient 1 | W | M | 16 | 100.00 | 100.00 | 73.33 | Plasma | 57.6 |
| Patient 2 | W | F | 13 | 100.00 | 8.00 | 6.67 | Plasma | 55.5 |

TABLE 4-continued

Clinical data for DASP verification cohort (100 control and 50 type 1 diabetic patients).
Sample race, gender, age, and the results of the three autoantibody assays are shown as
provided by the DASP. Protein concentration was measured by BCA assay and classification of
samples as serum or plasma was performed using the method of Gonzalez et al.[34]

| Sample ID | Race | Gender | Age | % of Assays > med AUC Designating Positive For GAD in DASP 2005 | % of Assays > med AUC Designating Positive For IA2 in DASP 2005 | % of Assays > med AUC Designating Positive For IAA in DASP 2005 | Specimen Type Predicted by Median of c49D2 | Total [Protein] Measured by BCA assay (ug/ul) |
|---|---|---|---|---|---|---|---|---|
| Patient 3 | W | M | 12 | 80.77 | 96.00 | 46.67 | Plasma | 50.0 |
| Patient 4 | W | F | 12 | 96.15 | 100.00 | 13.33 | Plasma | 44.7 |
| Patient 5 | W | M | 15 | 100.00 | 96.00 | 73.33 | Plasma | 96.9 |
| Patient 6 | W | M | 13 | 7.69 | 96.00 | 60.00 | Plasma | 35.2 |
| Patient 7 | W | M | 14 | 100.00 | 100.00 | 46.67 | Plasma | 56.1 |
| Patient 8 | W | F | 10 | 100.00 | 100.00 | 100.00 | Plasma | 48.1 |
| Patient 9 | W | M | 26 | 88.46 | 100.00 | 60.00 | Serum | 80.3 |
| Patient 10 | W | M | 20 | 19.23 | 96.00 | 6.67 | Serum | 91.9 |
| Patient 11 | W | f | 21 | 100.00 | 24.00 | 66.67 | Serum | 78.5 |
| Patient 12 | W | f | 17 | 96.15 | 60.00 | 6.67 | Serum | 81.5 |
| Patient 13 | W | m | 19 | 100.00 | 60.00 | 60.00 | Serum | 125.9 |
| Patient 14 | W | m | 24 | 38.46 | 48.00 | 6.67 | Serum | 76.1 |
| Patient 15 | German | f | 23 | 100.00 | 100.00 | 13.33 | Serum | 77.6 |
| Patient 16 | Iraqi | m | 27 | 61.54 | 0.00 | 86.67 | Serum | 68.9 |
| Patient 17 | W | m | 16 | 73.08 | 96.00 | 0.00 | Serum | 82.2 |
| Patient 18 | Australian | m | 28 | 100.00 | 100.00 | 93.33 | Serum | 67.9 |
| Patient 19 | C | m | 23 | 92.31 | 100.00 | 0.00 | Serum | 65.4 |
| Patient 20 | C | male | 24 | 100.00 | 92.00 | 86.67 | Serum | 69.5 |
| Patient 21 | C | male | 18 | 15.38 | 96.00 | 66.67 | Serum | 127.4 |
| Patient 22 | C | male | 17 | 92.31 | 100.00 | 73.33 | Serum | 48.2 |
| Patient 23 | C | male | 22 | 7.69 | 96.00 | 20.00 | Serum | 74.6 |
| Patient 24 | C | Female | 12 | 100.00 | 4.00 | 93.33 | Serum | 81.8 |
| Patient 25 | C | m | 15 | 100.00 | 8.00 | 26.67 | Serum | 74.4 |
| Patient 26 | C | f | 29 | 100.00 | 12.00 | 40.00 | Serum | 98.1 |
| Patient 27 | C | m | 21 | 46.15 | 24.00 | 0.00 | Serum | 89.7 |
| Patient 28 | C | f | 18 | 100.00 | 96.00 | 53.33 | Serum | 116.0 |
| Patient 29 | C | m | 14 | 100.00 | 8.00 | 100.00 | Serum | 90.3 |
| Patient 30 | C | f | 18 | 96.15 | 100.00 | 0.00 | Serum | 96.1 |
| Patient 31 | C | m | 21 | 100.00 | 100.00 | 100.00 | Serum | 74.1 |
| Patient 32 | C | f | 19 | 100.00 | 8.00 | 20.00 | Serum | 99.1 |
| Patient 33 | C | m | 17 | 96.15 | 100.00 | 86.67 | Serum | 82.0 |
| Patient 34 | C | f | 24 | 100.00 | 4.00 | 0.00 | Serum | 61.5 |
| Patient 35 | C | f | 22 | 96.15 | 96.00 | 20.00 | Serum | 105.0 |
| Patient 36 | C | f | 28 | 0.00 | 0.00 | 0.00 | Serum | 85.9 |
| Patient 37 | Mograbin Caucasian | Male | 24 | 96.15 | 4.00 | 40.00 | Serum | 152.4 |
| Patient 38 | European Caucasian | Male | 17 | 100.00 | 100.00 | 73.33 | Serum | 81.2 |
| Patient 39 | Australian | male | 26 | 100.00 | 100.00 | 73.33 | Serum | 63.0 |
| Patient 40 | caucas | male | 20 | 80.77 | 100.00 | 66.67 | Serum | 90.1 |
| Patient 41 | caucas | male | 26 | 100.00 | 100.00 | 60.00 | Serum | 59.4 |
| Patient 42 | caucas | male | 10 | 100.00 | 100.00 | 80.00 | Serum | 72.6 |
| Patient 43 | caucas | male | 15 | 100.00 | 100.00 | 100.00 | Serum | 88.2 |
| Patient 44 | caucas | male | 25 | 96.15 | 100.00 | 86.67 | Serum | 88.3 |
| Patient 45 | caucas | male | 26 | 100.00 | 100.00 | 80.00 | Serum | 112.5 |
| Patient 46 | caucas | female | 23 | 100.00 | 100.00 | 40.00 | Plasma | 93.0 |
| Patient 47 | caucas | male | 17 | 100.00 | 8.00 | 100.00 | Plasma | 95.0 |
| Patient 48 | caucas | male | 22 | 100.00 | 100.00 | 80.00 | Plasma | 66.0 |
| Patient 49 | S asian | male | 16 | 3.85 | 0.00 | 0.00 | Serum | 77.5 |
| Patient 50 | Cauc | male | 17 | 96.15 | 100.00 | 86.67 | Serum | 81.2 |

For global proteomics discovery analyses, 10 pooled control and 10 pooled diabetic blood serum/plasma samples were prepared, with 5 subjects comprising each pool. To broaden the proteomic coverage, intensive sample fractionation on protein and peptide levels were performed, and in combination with high throughput LC-MS/MS bottom-up proteomics platforms and the label-free accurate mass and time (AMT) tag quantification approach,[25,31] 24 proteins (FIG. 1) were identified that demonstrated significant changes (p<0.05, t test) between type 1 diabetic and control samples, including 4 proteins (AZGP1, CLU, SERPINA6, LUM) showing statistically significant differences between T1DM and healthy controls identified previously.[25]

To significantly improve the sensitivity and specificity of measurements and to evaluate the utility of these proteins as diabetes markers in large cohorts, proteolytic peptides were identified that can be used as surrogates of these proteins. To this end, an iterative screening approach was used to select proteolytic peptides that are both detectable in tryptic digests of blood serum/plasma and less interfered with by sample matrices,[27] which resulted in 52 peptides as surrogates for these 24 proteins in a multiplexed LC-MRM/MS assay (the assay details are in Table 5).

TABLE 5

Detailed parameters of the 52 peptide LC-MRM assays. precursor m/z, product m/z, product ion type, and the associated charge state for both the endogenous peptide and the standard isotope labeled analog are listed. Also listed are collision energy used in fragmentation of precursor ions and the average retention time of the peptide on the LC column. All peptides with the exception of ALNHLPLEYNSALYSR (SEQ ID NO: 12) were represented by one precursor/product ion pairs.

| Peptide Sequence | Modification | Gene Name | Protein Name | UniProt AccessID | Precursor Charge | Precursor Mz |
|---|---|---|---|---|---|---|
| EIPAWVPFDPAAQITK | | AZGP1 | Zinc-alpha-2-glycoprotein | P25311 | 2 | 891.97 |
| LSSGLVTAALYGR | | BTD | Biotinidase | P43251 | 2 | 654.37 |
| SHLIIAQVAK | | BTD | Biotinidase | P43251 | 2 | 540.33 |
| LFGEVTSPLFPK | | C1R | Complement C1r subcomponent | P00736 | 2 | 667.87 |
| VSVHPDYR | | C1R | Complement C1r subcomponent | P00736 | 2 | 486.75 |
| GESGGAVFLER | | C2 | Complement C2 | P06681 | 2 | 561.28 |
| HAIILLTDGK | | C2 | Complement C2 | P06681 | 2 | 540.82 |
| SSGQWQTPGATR | | C2 | Complement C2 | P06681 | 2 | 638.31 |
| DFDFVPPVVR | | C3 | Complement C3 | P01024 | 2 | 595.81 |
| TGLQEVEVK | | C3 | Complement C3 | P01024 | 2 | 501.78 |
| ITQVLHFTK | | C4A | Complement C4-A | P0C0L4 | 2 | 543.82 |
| ALNHLPLEYNSALYSR | | C6 | Complement component C6 | P13671 | 3 | 620.99 |
| ALNHLPLEYNSALYSR | | C6 | Complement component C6 | P13671 | 3 | 620.99 |
| SISCQEIPGQQSR | CAM | CFP | Properdin | P27918 | 2 | 745.36 |
| ELDESLQVAER | | CLU | Clusterin | P10909 | 2 | 644.82 |
| LFDSDPITVTVPVEVSR | | CLU | Clusterin | P10909 | 2 | 937.50 |
| TLLSNLEEAK | | CLU | Clusterin | P10909 | 2 | 559.31 |
| ALEQDLPVNIK | | CNDP1 | Beta-Ala-His dipeptidase | Q96KN2 | 2 | 620.35 |
| EWVAIESDSVQPVPR | | CNDP1 | Beta-Ala-His dipeptidase | Q96KN2 | 2 | 856.44 |
| ELLESYIDGR | | F2 | Prothrombin | P00734 | 2 | 597.80 |
| ETAASLLQAGYK | | F2 | Prothrombin | P00734 | 2 | 626.33 |
| QEPGENSEILPTLK | | GPX3 | Glutathione peroxidase 3 | P22352 | 2 | 777.90 |
| YVRPGGGFVPNFQLFEK | | GPX3 | Glutathione peroxidase 3 | P22352 | 3 | 652.34 |
| AGALNSNDAFVLK | | GSN | Gelsolin | P06396 | 2 | 660.35 |
| QTQVSVLPEGGETPLFK | | GSN | Gelsolin | P06396 | 2 | 915.49 |
| TGAQELLR | | GSN | Gelsolin | P06396 | 2 | 444.25 |
| EALVPLVADHK | | HGFAC | Hepatocyte growth factor activator | Q04756 | 2 | 596.34 |
| VANYVDWINDR | | HGFAC | Hepatocyte growth factor activator | Q04756 | 2 | 682.83 |

TABLE 5-continued

Detailed parameters of the 52 peptide LC-MRM assays. precursor m/z, product m/z, product ion type, and the associated charge state for both the endogenous peptide and the standard isotope labeled analog are listed. Also listed are collision energy used in fragmentation of precursor ions and the average retention time of the peptide on the LC column. All peptides with the exception of ALNHLPLEYNSALYSR (SEQ ID NO: 12) were represented by one precursor/product ion pairs.

| Peptide Sequence | Modification | Gene Name | Protein Name | UniProt AccessID | Precursor Charge | Precursor Mz |
|---|---|---|---|---|---|---|
| DSVTGTLPK | | KLKB1 | Plasma kallikrein | P03952 | 2 | 459.25 |
| EIIIHQNYK | | KLKB1 | Plasma kallikrein | P03952 | 2 | 579.32 |
| IAYGTQGSSGYSLR | | KLKB1 | Plasma kallikrein | P03952 | 2 | 730.36 |
| IYSGILNLSDITK | | KLKB1 | Plasma kallikrein | P03952 | 2 | 718.90 |
| DIPTNSPELEETLTHTITK | | KNG1 | Kininogen-1 | P01042 | 3 | 713.70 |
| TVGSDTFYSFK | | KNG1 | Kininogen-1 | P01042 | 2 | 626.30 |
| FNALQYLR | | LUM | Lumican | P51884 | 2 | 512.78 |
| ISNIPDEYFK | | LUM | Lumican | P51884 | 2 | 613.31 |
| NNQIDHIDEK | | LUM | Lumican | P51884 | 2 | 613.29 |
| AGLLRPDYALLGHR | | PGLYRP2 | N-acetyl muramoyl-L-alanine amidase | Q96PD5 | 3 | 517.96 |
| PSLSHLLSQYYGAGVAR | | PGLYRP2 | N-acetylmuramoyl-L-alanine amidase | Q96PD5 | 3 | 606.99 |
| TFTLLDPK | | PGLYRP2 | N-acetylmuramoyl-L-alanine amidase | Q96PD5 | 2 | 467.77 |
| EESLDSDLYAELR | | PPBP | Platelet basic protein | P02775 | 2 | 770.36 |
| NIQSLEVIGK | | PPBP | Platelet basic protein | P02775 | 2 | 550.82 |
| AQLLQGLGFNLTER | | SERPINA6 | Corticosteroid-binding globulin | P08185 | 2 | 780.43 |
| EENFYVDETTVVK | | SERPINA6 | Corticosteroid-binding globulin | P08185 | 2 | 786.88 |
| SVNDLYIQK | | SERPIND1 | Heparin cofactor 2 | P05546 | 2 | 540.29 |
| TLEAQLTPR | | SERPIND1 | Heparin cofactor 2 | P05546 | 2 | 514.79 |
| LGNQEPGGQTALK | | SERPINF2 | Alpha-2-antiplasmin | P08697 | 2 | 656.85 |
| FQPTLLTLPR | | SERPING1 | Plasma protease C1 inhibitor | P05155 | 2 | 593.35 |
| LLDSLPSDTR | | SERPING1 | Plasma protease C1 inhibitor | P05155 | 2 | 558.80 |
| LVLLNAIYISAK | | SERPINGI | Plasma protease C1 inhibitor | P05155 | 2 | 659.41 |
| TNLESILSYPK | | SERPING1 | Plasma protease C1 inhibitor | P05155 | 2 | 632.84 |

TABLE 5-continued

Detailed parameters of the 52 peptide LC-MRM assays. precursor m/z, product m/z, product ion type, and the associated charge state for both the endogenous peptide and the standard isotope labeled analog are listed. Also listed are collision energy used in fragmentation of precursor ions and the average retention time of the peptide on the LC column. All peptides with the exception of ALNHLPLEYNSALYSR (SEQ ID NO: 12) were represented by one precursor/product ion pairs.

| Peptide Sequence | Modification | Gene Name | Protein Name | UniProt AccessID | Precursor Charge | Precursor Mz |
|---|---|---|---|---|---|---|
| AADDTWEPFASGK | | TTR | Transthyretin | P02766 | 2 | 697.81 |
| GSPAINVAVHVFR | | TTR | Transthyretin | P02766 | 3 | 456.26 |

| Peptide Sequence | SIS Peptide Precursor MZ | Product Charge | Product Mz | SIS Peptide Product MZ | Product Ion Type | Collision Energy | Avg Measured Retention Time |
|---|---|---|---|---|---|---|---|
| EIPAWVPFDPAAQITK | 895.98 | 2 | 770.91 | 774.92 | y14 | 22.0 | 32.37 |
| LSSGLVTAALYGR | 659.37 | 1 | 850.48 | 860.49 | y8 | 23.0 | 20.22 |
| SHLIIAQVAK | 544.34 | 1 | 855.57 | 863.58 | y8 | 17.0 | 10.84 |
| LFGEVTSPLFPK | 671.88 | 1 | 1074.58 | 1082.60 | y10 | 21.0 | 26.67 |
| VSVHPDYR | 491.75 | 1 | 338.18 | 348.19 | y2 | 21.0 | 8.71 |
| GESGGAVFLER | 566.29 | 1 | 848.46 | 858.47 | y8 | 19.0 | 12.34 |
| HAIILLTDGK | 544.83 | 1 | 872.55 | 880.56 | y8 | 18.0 | 12.65 |
| SSGQWQTPGATR | 643.31 | 1 | 916.46 | 926.47 | y8 | 22.0 | 9.47 |
| DFDFVPPVVR | 600.82 | 1 | 567.36 | 577.37 | y5 | 17.0 | 26.67 |
| TGLQEVEVK | 505.78 | 1 | 731.39 | 739.41 | y6 | 16.0 | 10.43 |
| ITQVLHFTK | 547.83 | 2 | 487.28 | 491.28 | y8 | 19.0 | 11.6 |
| ALNHLPLEYNSALYSR | 624.33 | 1 | 810.41 | 820.42 | y7 | 31.0 | 17.86 |
| ALNHLPLEYNSALYSR | 624.33 | 1 | 425.21 | 435.22 | y3 | 31.0 | 17.86 |
| SISCQEIPGQQSR | 750.36 | 1 | 672.34 | 682.35 | y6 | 25.0 | 9.59 |
| ELDESLQVAER | 649.83 | 1 | 602.33 | 612.33 | y5 | 21.0 | 11.71 |
| LFDSDPITVTVPVEVSR | 942.50 | 1 | 686.38 | 696.39 | y6 | 25.0 | 26.74 |
| TLLSNLEEAK | 563.32 | 1 | 903.48 | 911.49 | y8 | 17.0 | 17.15 |
| ALEQDLPVNIK | 624.36 | 1 | 570.36 | 578.38 | y5 | 19.0 | 16.66 |
| EWVAIESDSVQPVPR | 861.44 | 1 | 468.29 | 478.30 | y4 | 25.0 | 18.09 |
| ELLESYIDGR | 602.81 | 1 | 710.35 | 720.36 | y6 | 20.0 | 18.07 |
| ETAASLLQAGYK | 630.34 | 1 | 879.49 | 887.51 | y8 | 19.0 | 14.39 |
| QEPGENSEILPTLK | 781.91 | 2 | 649.35 | 653.36 | y12 | 24.0 | 16.24 |
| YVRPGGGFVPNFQLFEK | 655.02 | 2 | 511.77 | 515.78 | y8 | 17.0 | 26.68 |
| AGALNSNDAFVLK | 664.36 | 1 | 1007.52 | 1015.53 | y9 | 21.0 | 16.26 |
| QTQVSVLPEGGETPLFK | 919.49 | 1 | 1187.63 | 1195.64 | y11 | 26.0 | 22.96 |
| TGAQELLR | 449.26 | 1 | 729.43 | 739.43 | y6 | 15.0 | 10.49 |
| EALVPLVADHK | 600.35 | 1 | 779.44 | 787.46 | y7 | 20.0 | 13.04 |
| VANYVDWINDR | 687.84 | 1 | 818.38 | 828.39 | y6 | 22.0 | 19.7 |
| DSVTGTLPK | 463.26 | 1 | 616.37 | 624.38 | y6 | 19.0 | 9.94 |

-continued

| Peptide Sequence | SIS Peptide Precursor MZ | Product Charge | Product Mz | SIS Peptide Product MZ | Product Ion Type | Collision Energy | Avg Measured Retention Time |
|---|---|---|---|---|---|---|---|
| EIIIHQNYK | 583.33 | 1 | 689.34 | 697.35 | y5 | 21.0 | 9.51 |
| IAYGTQGSSGYSLR | 735.37 | 1 | 826.41 | 836.41 | y8 | 27.0 | 11.07 |
| IYSGILNLSDITK | 722.91 | 1 | 563.30 | 571.32 | Y5 | 28.0 | 26.84 |
| DIPTNSPELEETLTHTITK | 716.37 | 2 | 955.99 | 960.00 | y17 | 14.0 | 22.26 |
| TVGSDTFYSFK | 630.31 | 1 | 1051.47 | 1059.49 | y9 | 18.0 | 15.94 |
| FNALQYLR | 517.79 | 1 | 763.45 | 773.45 | y6 | 16.0 | 20.88 |
| ISNIPDEYFK | 617.32 | 1 | 798.37 | 806.38 | y6 | 18.0 | 15.85 |
| NNQIDHIDEK | 617.30 | 1 | 869.44 | 877.45 | y7 | 21.0 | 8.69 |
| AGLLRPDYALLGHR | 521.30 | 1 | 369.20 | 379.21 | y3 | 18.0 | 16.26 |
| PSLSHLLSQYYGAGVAR | 610.32 | 1 | 530.30 | 540.31 | y6 | 20.0 | 22.69 |
| TFTLLDPK | 471.77 | 1 | 686.41 | 694.42 | y6 | 14.0 | 18.02 |
| EESLDSDLYAELR | 775.37 | 1 | 966.49 | 976.50 | y8 | 22.0 | 21.63 |
| NIQSLEVIGK | 554.83 | 1 | 873.50 | 881.52 | y8 | 15.0 | 14.56 |
| AQLLQGLGFNLTER | 785.43 | 1 | 836.43 | 846.43 | y7 | 25.0 | 29.17 |
| EENFYVDETTVVK | 790.88 | 1 | 791.41 | 799.43 | Y7 | 23.0 | 15.21 |
| SVNDLYIQK | 544.30 | 1 | 779.43 | 787.44 | y6 | 16.0 | 11.15 |
| TLEAQLTPR | 519.79 | 1 | 814.44 | 824.45 | y7 | 17.0 | 11.26 |
| LGNQEPGGQTALK | 660.85 | 1 | 771.44 | 779.45 | y8 | 22.0 | 9.01 |
| FQPTLLTLPR | 598.36 | 2 | 455.79 | 460.79 | y8 | 18.0 | 24.18 |
| LLDSLPSDTR | 563.80 | 1 | 575.28 | 585.29 | y5 | 17.0 | 12.15 |
| LVLLNAIYLSAK | 663.42 | 1 | 1105.66 | 1113.68 | y10 | 20.0 | 31.34 |
| TNLESILSYPK | 636.85 | 1 | 807.46 | 815.48 | y7 | 20.0 | 22.91 |
| AADDTWEPFASGK | 701.82 | 1 | 606.32 | 614.34 | y6 | 23.0 | 16.94 |
| GSPAINVAVHVFR | 459.59 | 3 | 408.24 | 411.58 | y11 | 11.0 | 17.59 |

Quantification of these 52 peptides was assisted by spiking of their individually custom-synthesized stable-isotope labeled standard (SIS) peptides into tryptic digests of each individual serum/plasma sample of the DASP cohort. Because these SIS peptides co-elute, ionize and fragment identically with their endogenous counterparts,[26,27] and the spiked amounts were individually adjusted to be close to their endogenous levels,[27] the peak area ratios between endogenous and SIS peptides accurately reflects their natural abundances and provides reliable estimates of the associated protein abundances. Therefore, these ratios were used as measures of the abundances of the endogenous peptides and their corresponding proteins. To minimize the systematic errors during quantification of these selected peptides, the orders of both the sample proteolytic digestion and LC-MRM/MS analysis were randomized.

EXAMPLE 3

Verification of Peptide Markers in the DASP Cohort

Figure 2A:
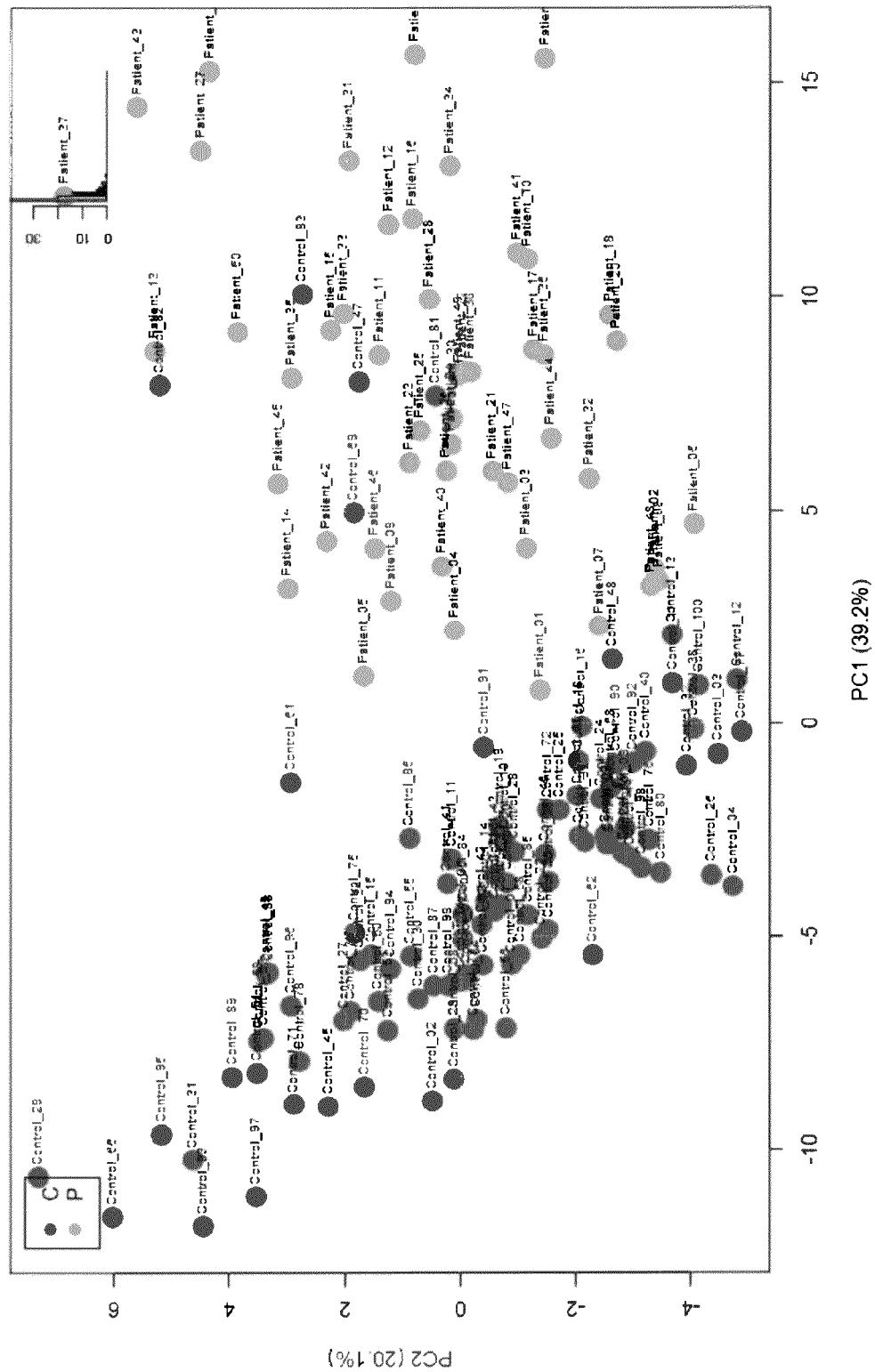
FIGS. 2a-b. Analysis of outlier samples in the verification DASP cohort (100 control and 50 type 1 diabetic subjects). Relative peptide abundances were used in the data analysis, which were calculated as the ratios between endogenous peptides and their spiked-in SIS analogs. Partial least squares (PLS) regression and correlation analyses were performed using DAnTE. (a) PLS scores plot showing the segregation of the two groups of samples, with red dots and blue dots representing each control and patient samples, respectively. (b) Plot showing the Pearson correlation between each sample and all other samples in the cohort. The lighter the color, the better the correlation. The red and blue bars indicate control and patient samples, respectively.

To minimize the systematic errors during quantification of these selected peptides, the orders of both the sample proteolytic digestion and LC-MRM/MS analysis were randomized. Statistical analyses were performed on the measured peptide abundances (the peak area ratios between endogenous peptides and their SIS analogs) to evaluate the differences of these 52 peptides between individual control and type 1 diabetic subjects in a large cohort. The analysis is based on all 150 individuals without removing any outliers, since no further diagnostic or follow-up information beyond the original sample designation, collection and demographic information was available from the DASP, despite the fact that there were samples clearly showing poor correlation within each sample group based on the PLS and the correlation analyses (FIGS. 2a and b).

Figure 3A:
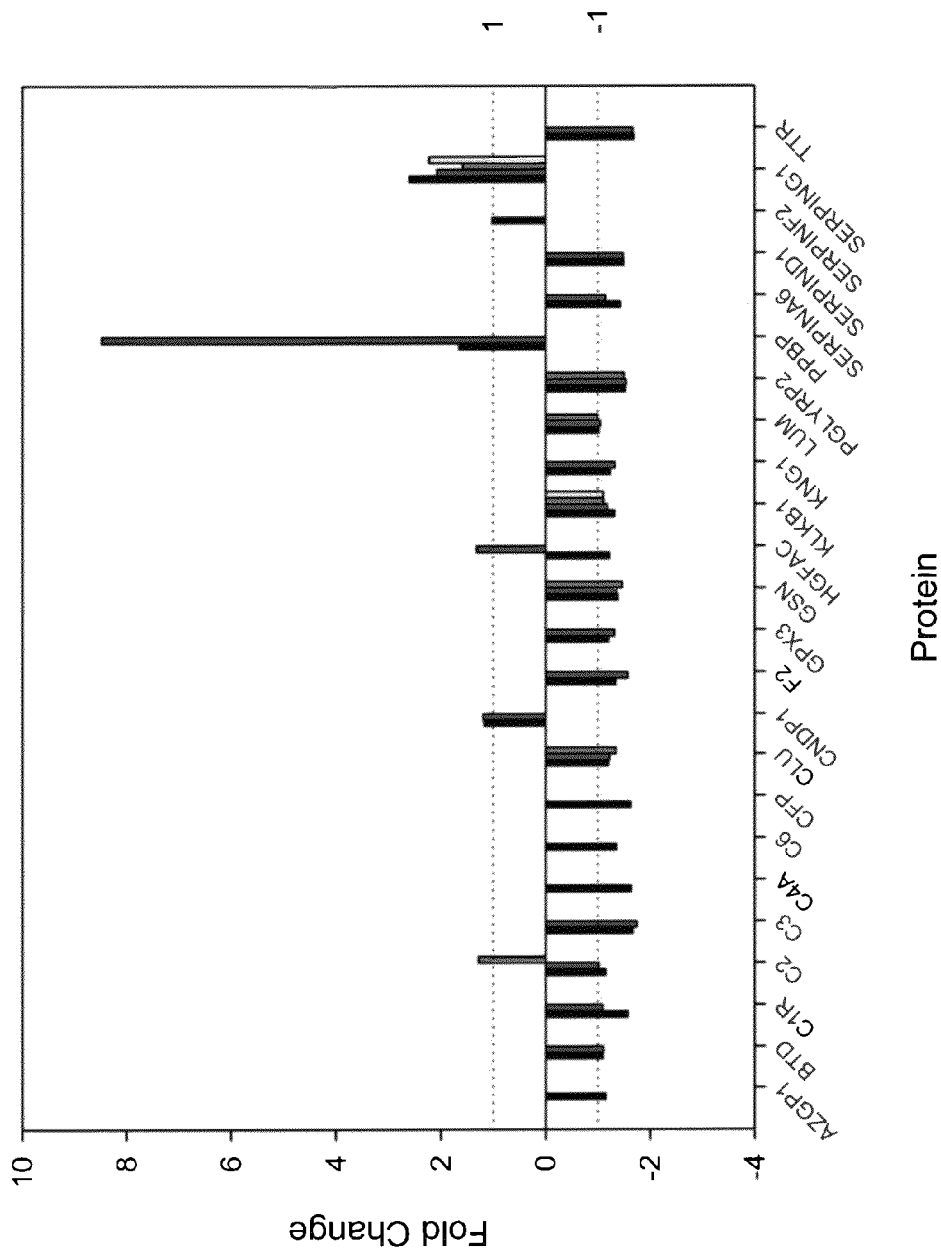
FIGS. 3a-b. Results of all 52 peptide assays performed in the verification DASP cohort (100 control and 50 type 1 diabetic subjects). Relative peptide abundances were used in the data analysis, which were calculated as the ratios between endogenous peptides and their spiked-in SIS analogs. Significance test was performed with non-parametric Mann Whitney U test, and the p values and other statistical analysis results are in Table 3. (a) Fold change in abundance of each peptide, calculated by comparing the mean of peptide abundance in the type 1 diabetic state to that in control. Each column represents a unique peptide, and the peptides are grouped by gene name of each protein. The two dashed lines indicate fold changes of 1.0 and −1.0, which represent no change. (b) Box-Whisker plots of each peptide shows the entire range of relative peptide abundances in control and type 1 diabetic groups, with the lower and upper lines of each box representing the $25^{th}$ and $75^{th}$ percentiles, respectively. The black and red horizontal lines within each box represent the median and mean values, respectively. The crossbars extend to the $10^{th}$ and $90^{th}$ percentile values, with outliers beyond this range shown as individual points. For each peptide, the left box plot represents the control group and the right box the patients. The sequences on the x-axis are shown in SEQ ID NOS: 1-52, respectively.
Figure 3B:
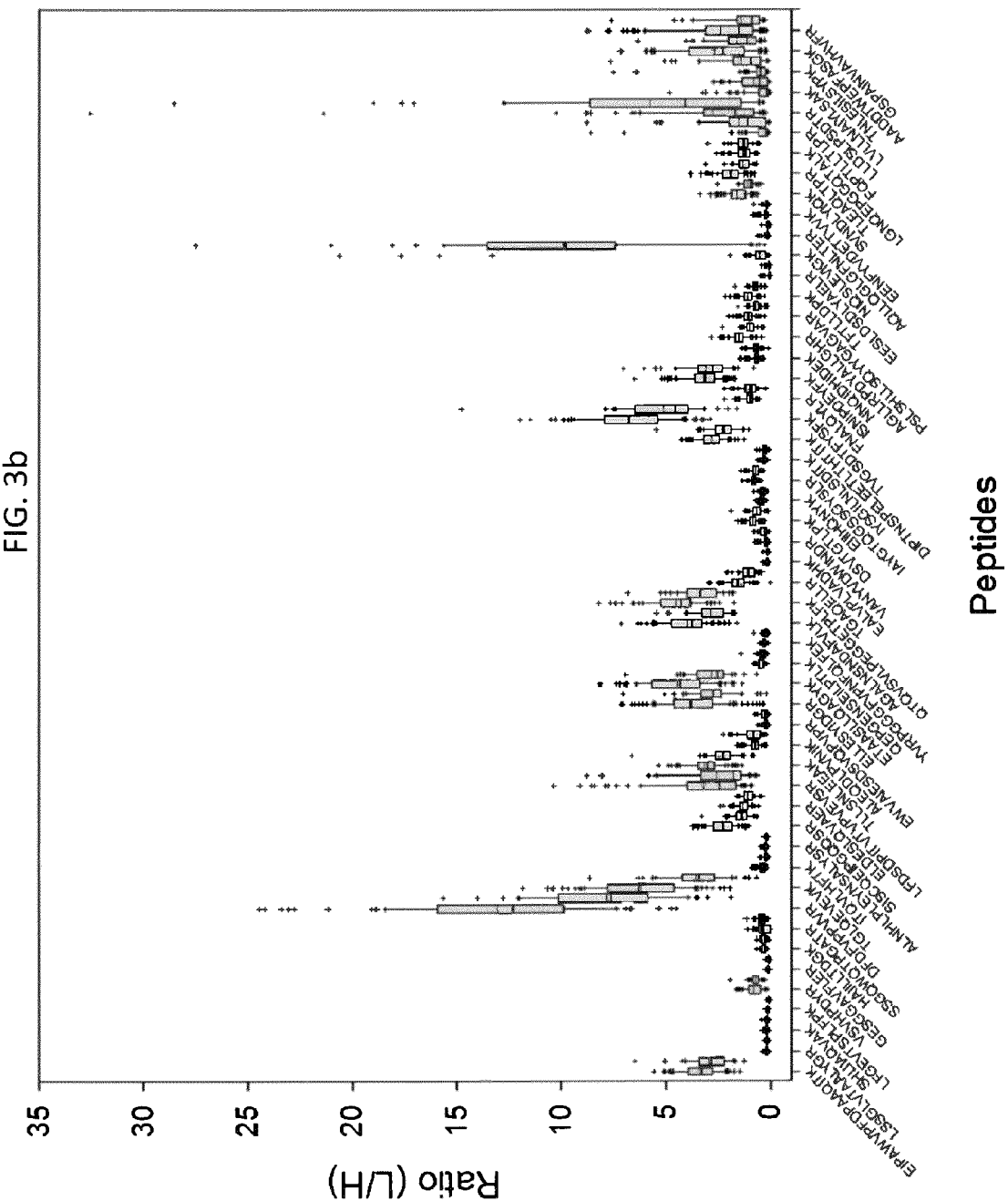
Figure 4A:
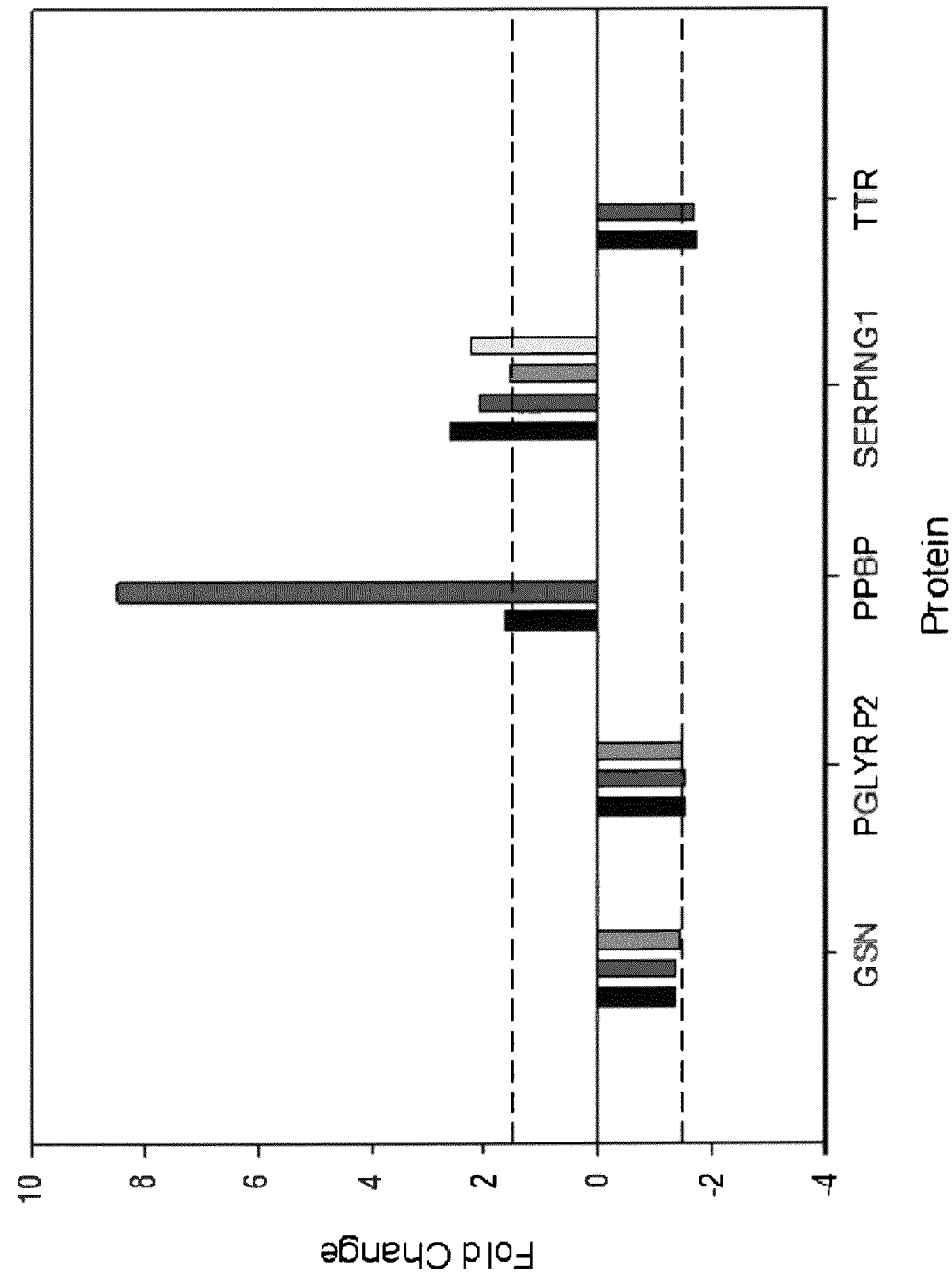
FIGS. 4a-d. Results of the targeted peptide assay performance in the verification DASP cohort (100 control and 50 type 1 diabetic subjects). Relative peptide abundance was used in the data analysis, which is calculated as the ratio between an endogenous peptide and its spiked-in SIS analog. Fourteen peptides representing 5 proteins are shown, and each peptide was determined to be significant ($p<0.01$, actual p values in Table 3) by non-parametric Mann Whitney U test. The full results of all 52 peptide assays are in FIGS. 3a and b and Table 3. (a) Fold change in abundance of each peptide, calculated by comparing the mean of peptide abundance in the type 1 diabetic state to that in control. Each column represents a unique peptide, and the peptides are grouped by gene name of each protein. The two dashed lines indicate fold changes of 1.5 and −1.5. (b) Box-Whisker plots of each peptide show the entire range of relative peptide abundances in control and type 1 diabetic groups, with the lower and upper lines of each box representing the $25^{th}$ and $75^{th}$ percentiles, respectively. The black and red horizontal lines within each box represents the median and mean values, respectively. The crossbars extend to the $10^{th}$ and $90^{th}$ percentile values, with outliers beyond this range shown as individual points. For each peptide, the left box plot represents the control group and the right box the patients. The sequences on the x-axis are shown in SEQ ID NOS: 23, 24, 25, 37, 38, 39, 40, 41, 47, 48, 49, 50, 51, and 52, respectively. (c) ROC curve analysis of the 6 peptides constitutive of proteins PPBP and SERPING1 (SEQ ID NOS: 40, 41, 47, 48, 49, and 50, from top to bottom, respectively) and showing up-regulation in T1DM compared to the control group. The area under the curve for each peptide is represented by the A value. The higher the A value, the better the sensitivity and specificity of this peptide assay. Peptides are presented in the same order as in (b). (d) ROC curve analysis of the 8 peptides constitutive of proteins GSN, PGLYRP2 and TTR (SEQ ID NOS: 23, 24, 25, 37, 38, 39, 51 and 52, from top to bottom, respectively) and showing down-regulation in T1DM compared to the control group. Peptides are presented in the same order as in (b).
Figure 4B:
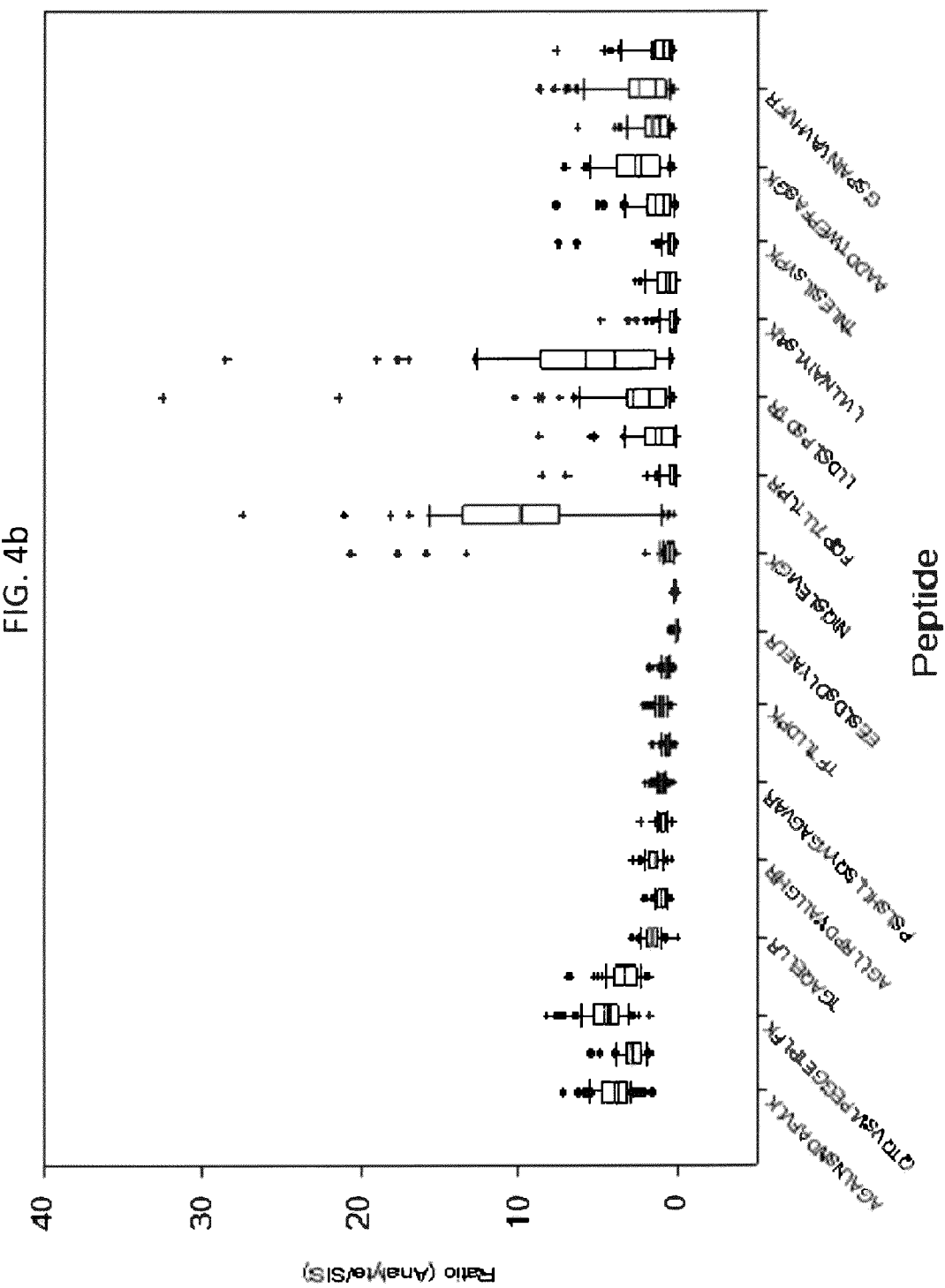
Figure 4C:
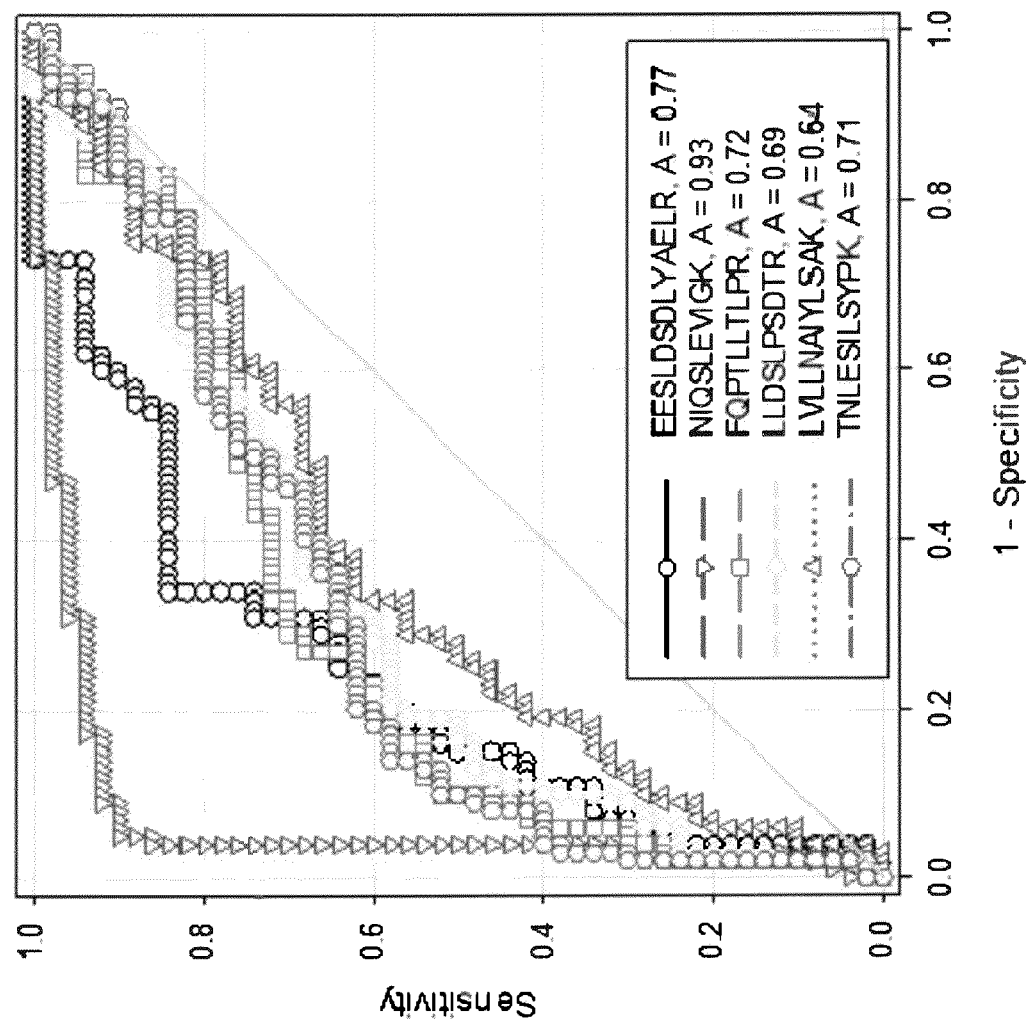
Figure 4D:
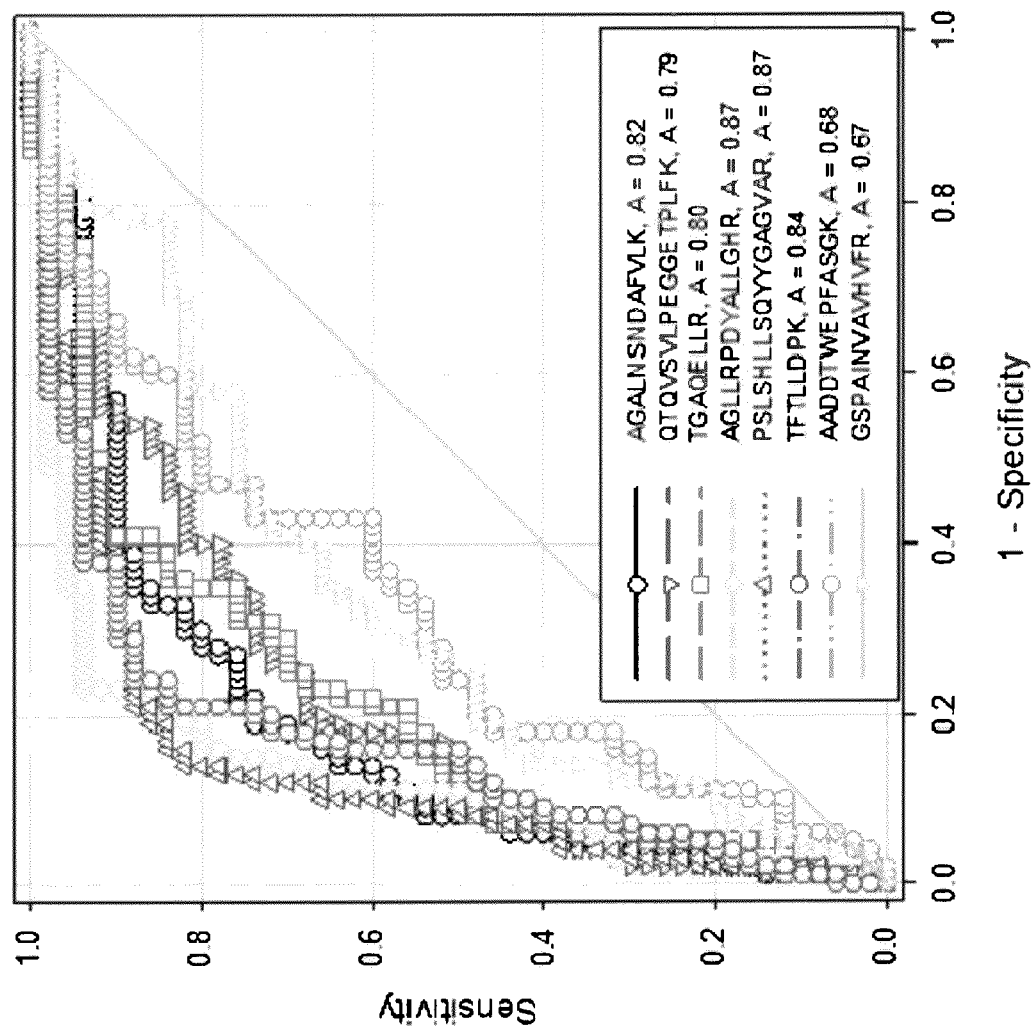

Thirty-three peptides were statistically significant on the basis of the p values reported in the Mann-Whitney U test (p<0.001), with 10 of these peptides being down-regulated greater than 1.5 fold and 6 peptides up-regulated more than 1.5 fold in type 1 diabetic subjects relative to controls. Receiver operator characteristic (ROC) curve analysis was used to evaluate the performance of each peptide assay in discriminating type 1 diabetic from control individuals. The areas under the curve (AUC) with 95% confidence intervals showed that 14 of these 33 peptides had AUCs >0.8 (the full statistical results for all 52 peptides are in Table 6a and FIGS. 3a and b; and the summary for the 14 peptides is shown in Table 6b).

TABLE 6a

Statistical analysis of peptide abundances in the DASP verification cohort samples (100 control and 50 type 1 diabetic subjects). Relative peptide abundances were used and were represented by peak area ratios of the endogenous peptides to their SIS analogs. Calculations of mean, fold change, and Mann-Whitney U test were carried out in DAnTE, while areas under the curve (AUC), adjusted sensitivities at 90% specificity (AS90) and associated cut-off values were calculated with the ROC toolbox in SigmaPlot. The peptide abundance cut-off values at AS90 were used to identify the blind samples. The assay specificity and sensitivity was calculated after unblinding the clinical status of the DASP validation samples (10 control and 10 type 1 diabetic subjects).

| Protein | Peptide | Mean Abundance Patient | Mean Abundance Control | Fold Change | MWUT p-value (Non Para.) | AUC | Cutoff AS90 | AS90 | Specificity | Sensitivity |
|---|---|---|---|---|---|---|---|---|---|---|
| AZGP1 | EIPAWVPFDPAAQITK | 2.96 | 3.41 | -1.2 | 2.43E-03 | 0.65 | 2.16 | 0.22 | 1 | 0 |
| BTD | LSSGLVTAALYGR | 0.19 | 0.21 | -1.1 | 5.59E-02 | 0.6 | 0.1452 | 0.18 | 0.2 | 0.6 |
| BTD | SHLIIAQVAK | 0.19 | 0.21 | -1.1 | 7.19E-02 | 0.59 | 0.1424 | 0.22 | 0.3 | 0.6 |
| C1R | LFGEVTSPLFPK | 0.08 | 0.13 | -1.6 | 4.58E-11 | 0.83 | 0.0766 | 0.52 | 0.5 | 0.7 |
| C1R | VSVHPDYR | 0.73 | 0.80 | -1.1 | 2.45E-01 | 0.56 | 0.3395 | 0.02 | 1 | 0 |
| C2 | GESGGAVFLER | 0.11 | 0.12 | -1.2 | 3.09E-02 | 0.61 | 0.0677 | 0.14 | 0.2 | 0.9 |
| C2 | HAIILLTDGK | 0.33 | 0.33 | -1.0 | 7.60E-01 | 0.52 | 0.224 | 0.1 | 0 | 0.3 |
| C2 | SSGQWQTPGATR | 0.45 | 0.36 | 1.3 | 1.00E-01 | 0.58 | 0.666 | 0.12 | 1 | 0 |
| C3 | DFDFVPPVVR | 7.83 | 13.04 | -1.7 | 3.06E-11 | 0.83 | 7.626 | 0.52 | 0.1 | 1 |
| C3 | TGLQEVEVK | 3.57 | 6.23 | -1.7 | 1.81E-12 | 0.85 | 3.671 | 0.58 | 0.1 | 1 |
| C4A | ITQVLHFTK | 0.25 | 0.41 | -1.6 | 3.63E-10 | 0.81 | 0.2384 | 0.6 | 0.3 | 1 |
| C6 | ALNHLPLEYNSALYSR | 0.21 | 0.28 | -1.4 | 2.43E-09 | 0.8 | 0.1904 | 0.4 | 0.2 | 0.7 |
| CFP | SISCQEIPGQQSR | 1.40 | 2.29 | -1.6 | 2.44E-14 | 0.88 | 1.562 | 0.7 | 0.2 | 1 |
| CLU | ELDESLQVAER | 1.09 | 1.31 | -1.2 | 7.85E-05 | 0.7 | 0.9392 | 0.36 | 0.3 | 0.8 |
| CLU | LFDSDPITVTVPVEVSR | 2.60 | 3.18 | -1.2 | 1.98E-02 | 0.62 | 1.434 | 0.3 | 1 | 0 |
| CLU | TLLSNLEEAK | 2.32 | 3.12 | -1.3 | 8.17E-10 | 0.81 | 2.16 | 0.4 | 0.3 | 0.9 |
| CNDP1 | ALEQDLPVNIK | 0.88 | 0.75 | 1.2 | 3.67E-01 | 0.54 | 1.228 | 0.22 | 1 | 0.1 |
| CNDP1 | EWVAIESDSVQPVPR | 0.29 | 0.24 | 1.2 | 2.86E-01 | 0.55 | 0.3727 | 0.26 | 0.9 | 0.2 |
| F2 | ELLESYIDGR | 2.82 | 3.79 | -1.3 | 5.44E-06 | 0.73 | 2.083 | 0.18 | 0.7 | 0.2 |
| F2 | ETAASLLQAGYK | 2.85 | 4.48 | -1.6 | 2.88E-10 | 0.82 | 2.523 | 0.5 | 0 | 1 |
| GPX3 | QEPGENSEILPTLK | 0.41 | 0.49 | -1.2 | 1.17E-04 | 0.69 | 0.3347 | 0.34 | 1 | 0.2 |
| GPX3 | YVRPGGGFVPNFQLFEK | 0.24 | 0.32 | -1.3 | 5.33E-08 | 0.77 | 0.222 | 0.46 | 0.2 | 0.8 |
| GSN | AGALNSNDAFVLK | 2.90 | 4.01 | -1.4 | 9.64E-11 | 0.82 | 3.04 | 0.56 | 0.6 | 1 |
| GSN | QTQVSVLPEGGETPLFK | 3.35 | 4.53 | -1.4 | 9.76E-09 | 0.79 | 3.094 | 0.46 | 1 | 0.6 |
| GSN | TGAQELLR | 1.08 | 1.59 | -1.5 | 3.41E-09 | 0.8 | 1.036 | 0.5 | 0.3 | 1 |
| HGFAC | EALVPLVADHK | 0.13 | 0.16 | -1.2 | 5.35E-04 | 0.67 | 0.1014 | 0.26 | 0.5 | 0 |
| HGFAC | VANYVDWINDR | 0.34 | 0.26 | 1.3 | 3.85E-03 | 0.64 | 0.4477 | 0.26 | 0.9 | 0 |
| KLKB1 | DSVTGTLPK | 0.66 | 0.88 | -1.3 | 7.29E-06 | 0.73 | 0.5584 | 0.4 | 0 | 1 |
| KLKB1 | EIIHQNYK | 0.36 | 0.43 | -1.2 | 9.84E-04 | 0.67 | 0.298 | 0.3 | 0.3 | 0.4 |
| KLKB1 | IAYGTQGSSGYSLR | 0.74 | 0.82 | -1.1 | 4.76E-03 | 0.64 | 0.6161 | 0.32 | 0.7 | 0.3 |
| KLKB1 | IYSGILNLSDITK | 0.29 | 0.32 | -1.1 | 4.89E-02 | 0.6 | 0.2165 | 0.3 | 0.7 | 0.3 |
| KNG1 | DIPTNSPELEETLTHTITK | 2.30 | 2.85 | -1.2 | 2.68E-07 | 0.76 | 2.077 | 0.32 | 0.8 | 0.1 |

TABLE 6a-continued

Statistical analysis of peptide abundances in the DASP verification cohort samples (100 control and 50 type 1 diabetic subjects). Relative peptide abundances were used and were represented by peak area ratios of the endogenous peptides to their SIS analogs. Calculations of mean, fold change, and Mann-Whitney U test were carried out in DAnTE, while areas under the curve (AUC), adjusted sensitivities at 90% specificity (AS90) and associated cut-off values were calculated with the ROC toolbox in SigmaPlot. The peptide abundance cut-off values at AS90 were used to identify the blind samples. The assay specificity and sensitivity was calculated after unblinding the clinical status of the DASP validation samples (10 control and 10 type 1 diabetic subjects).

| Protein | Peptide | Mean Abundance Patient | Mean Abundance Control | Fold Change | MWUT p-value (Non Para.) | AUC | Cutoff AS90 | AS90 | Specificity | Sensitivity |
|---|---|---|---|---|---|---|---|---|---|---|
| KNG1 | TVGSDTFYSFK | 5.12 | 6.80 | -1.3 | 2.98E-07 | 0.76 | 4.31 | 0.42 | 0.2 | 1 |
| LUM | FNALQYLR | 1.00 | 1.02 | -1.0 | 2.67E-01 | 0.56 | 0.7288 | 0.26 | 0.2 | 0.1 |
| LUM | ISNIPDEYFK | 3.07 | 3.21 | -1.0 | 1.03E-01 | 0.58 | 2.31 | 0.28 | 0.4 | 0.2 |
| LUM | NNQIDHIDEK | 0.69 | 0.69 | -1.0 | 6.65E-01 | 0.52 | 0.4743 | 0.12 | 0.5 | 0.1 |
| PGLYRP2 | AGLLRPDYALLGHR | 0.99 | 1.51 | -1.5 | 8.33E-14 | 0.87 | 0.9985 | 0.5 | 0.7 | 0.8 |
| PGLYRP2 | PSLSHLLSQYYGAGVAR | 0.70 | 1.08 | -1.5 | 1.77E-13 | 0.87 | 0.7502 | 0.66 | 0.8 | 1 |
| PGLYRP2 | TFTLLDPK | 0.73 | 1.09 | -1.5 | 1.31E-11 | 0.84 | 0.7132 | 0.46 | 0.8 | 0.9 |
| PPBP | EESLDSDLYAELR | 0.11 | 0.07 | 1.6 | 8.41E-08 | 0.77 | 0.1078 | 0.34 | 0.3 | 1 |
| PPBP | NIQSLEVIGK | 9.89 | 1.17 | 8.5 | 6.62E-18 | 0.93 | 0.9543 | 0.92 | 1 | 1 |
| SERPINA6 | AQLLQGLGFNLTER | 0.13 | 0.19 | -1.4 | 1.05E-06 | 0.75 | 0.1071 | 0.36 | 1 | 0 |
| SERPINA6 | EENFYVDETTVVK | 0.24 | 0.28 | -1.1 | 1.00E-01 | 0.58 | 0.162 | 0.14 | 0.9 | 0.3 |
| SERPIND1 | SVNDLYIQK | 1.08 | 1.61 | -1.5 | 9.15E-11 | 0.83 | 0.9762 | 0.5 | 0.3 | 0.8 |
| SERPIND1 | TLEAQLTPR | 1.31 | 1.95 | -1.5 | 1.17E-11 | 0.84 | 1.283 | 0.5 | 0.4 | 0.9 |
| SERPINF2 | LGNQEPGGQTALK | 1.32 | 1.30 | 1.0 | 6.96E-01 | 0.52 | 1.908 | 0.08 | 1 | 0 |
| SERPING1 | FQPTLLTLPR | 1.48 | 0.57 | 2.6 | 1.71E-05 | 0.72 | 1.079 | 0.52 | 0.7 | 1 |
| SERPING1 | LLDSLPSDTR | 5.76 | 2.79 | 2.1 | 1.39E-04 | 0.69 | 5.533 | 0.4 | 1 | 1 |
| SERPING1 | LVLLNAIYLSAK | 0.79 | 0.50 | 1.6 | 6.16E-03 | 0.64 | 1.188 | 0.28 | 0.7 | 1 |
| SERPING1 | TNLESILSYPK | 1.43 | 0.64 | 2.2 | 2.49E-05 | 0.71 | 0.9322 | 0.52 | 0.8 | 1 |
| TTR | AADDTWEPFASGK | 1.59 | 2.69 | -1.7 | 3.11E-04 | 0.68 | 0.5788 | 0.16 | 1 | 0.8 |
| TTR | GSPAINVAVHVFR | 1.43 | 2.38 | -1.7 | 5.35E-04 | 0.67 | 0.4878 | 0.2 | 1 | 0.8 |

TABLE 6b

Statistical analysis of peptide abundances in the DASP verification cohort samples (100 control/50 T1DM subjects). Relative peptide abundances were used and were represented by peak area ratios of the endogenous peptides to their SIS analogs. Calculations of mean, fold change, and Mann-Whitney U test were carried out in DAnTE, while areas under the curve (AUC), adjusted sensitivities at 90% specificity (AS90) and associated cut-off values were calculated with the ROC toolbox in SigmaPlot. The peptide abundance cut-off values at AS90 were used to identify the blind samples. The assay specificity and sensitivity was calculated after unblinding the clinical status of the DASP validation samples (10 control and 10 T1DM subjects).

| Protein | Peptide | Mean Abundance Patient | Mean Abundance Control | Fold Change | MWUT p-value (Non Para.) | AUC | Cutoff AS90 | AS90 | Specificity | Sensitivity |
|---|---|---|---|---|---|---|---|---|---|---|
| GSN | AGALNSNDAFVLK | 2.900786 | 4.005019 | 1.380666826 | 9.64E-11 | 0.82 | 3.04 | 0.56 | 0.6 | 1 |
| GSN | QTQVSVLPEGGETPLFK | 3.349584 | 4.5310325 | 1.352714994 | 9.76E-09 | 0.79 | 3.094 | 0.46 | 1 | 0.6 |

TABLE 6b-continued

Statistical analysis of peptide abundances in the DASP verification cohort samples (100 control/50 T1DM subjects). Relative peptide abundances were used and were represented by peak area ratios of the endogenous peptides to their SIS analogs. Calculations of mean, fold change, and Mann-Whitney U test were carried out in DAnTE, while areas under the curve (AUC), adjusted sensitivities at 90% specificity (AS90) and associated cut-off values were calculated with the ROC toolbox in SigmaPlot. The peptide abundance cut-off values at AS90 were used to identify the blind samples. The assay specificity and sensitivity was calculated after unblinding the clinical status of the DASP validation samples (10 control and 10 T1DM subjects).

| Protein | Peptide | Mean Abundance Patient | Mean Abundance Control | Fold Change | MWUT p-value (Non Para.) | AUC | Cutoff AS90 | AS90 | Specificity | Sensitivity |
|---|---|---|---|---|---|---|---|---|---|---|
| GSN | TGAQELLR | 1.079215 | 1.5866765 | -1.470213535 | 3.41E-09 | 0.8 | 1.036 | 0.5 | 0.3 | 1 |
| PGLYRP2 | AGLLRPDYALLGHR | 0.99 | 1.51 | -1.52 | 8.33E-14 | 0.87 | 0.9985 | 0.5 | 0.7 | 0.8 |
| PGLYRP2 | PSLSHLLSQYYGAGVAR | 0.70 | 1.08 | -1.54 | 1.77E-13 | 0.87 | 0.7502 | 0.66 | 0.8 | 1 |
| PGLYRP2 | TFTLLDPK | 0.728788 | 1.0931765 | -1.499992453 | 1.31E-11 | 0.84 | 0.7132 | 0.46 | 0.8 | 0.9 |
| PPBP | EESLDSDLYAELR | 0.11 | 0.07 | 1.64 | 8.41E-08 | 0.77 | 0.1078 | 0.34 | 0.3 | 1 |
| PPBP | NIQSLEVIGK | 9.89 | 1.17 | 8.48 | 6.62E-18 | 0.93 | 0.9543 | 0.92 | 1 | 1 |
| SERPING1 | FQPTLLTLPR | 1.48 | 0.57 | 2.59 | 1.71E-05 | 0.72 | 1.079 | 0.52 | 0.7 | 1 |
| SERPING1 | LLDSLPSDTR | 5.76 | 2.79 | 2.07 | 1.39E-04 | 0.69 | 5.533 | 0.4 | 1 | 1 |
| SERPING1 | LVLLNAIYLSAK | 0.79 | 0.50 | 1.58 | 6.16E-03 | 0.64 | 1.188 | 0.28 | 0.7 | 1 |
| SERPING1 | TNLESILSYPK | 1.43 | 0.64 | 2.22 | 2.49E-05 | 0.71 | 0.9322 | 0.52 | 0.8 | 1 |
| TTR | AADDTWEPFASGK | 1.59 | 2.69 | -1.69 | 3.11E-04 | 0.68 | 0.5788 | 0.16 | 1 | 0.8 |
| TTR | GSPAINVAVHVFR | 1.43 | 2.38 | -1.67 | 5.35E-04 | 0.67 | 0.4878 | 0.2 | 1 | 0.8 |

Of note are 3 proteins, gelsolin (GSN), N-acetylmuramoyl-L-alanine amidase (PGLYRP2) and transthyretin (TTR), which showed significant down-regulation among all of their 8 constitutive peptides. The relative levels of down-regulation among peptides from the same proteins agree well with each other. Two proteins, platelet basic protein (PPBP) and plasma protease C1 inhibitor (SERPING1), showed significant up-regulation among the 6 surrogate peptides monitored, although the relative levels of up-regulation between the two peptides from PPBP do not agree well (FIGS. 4a-d; discussed below), with peptide NIQSLEVIGK (SEQ ID NO: 41) having the dramatic up-regulation of 8.5 fold (p=6.62E-18, U test) in the type 1 diabetic group. This peptide also had the highest AUC of 0.93 in differentiating disease from control.

EXAMPLE 4

Utility of Peptide Markers for Diagnosing T1DM

To evaluate the utility of these assays in diagnosing T1DM, the cut-off values of peak area ratios corresponding to sensitivity at 90% specificity ($AS_{90}$) were obtained from the sensitivity and specificity reports of ROC curve analyses for each peptide,[18] and this value was used as a threshold to classify the 20 blind samples into control and type 1 diabetic individuals. After sample unblinding (the clinical parameters of the blind set are reported in Table 7), the sensitivity for each peptide assay was calculated as the percentage of sera/plasma from individuals reported as positive using the cut-off value at $AS_{90}$, and the specificity was calculated as the percentage of control sera/plasma reported as negative using the same threshold.

TABLE 7

Clinical data for the blind DASP cohort (10 control and 10 type 1 diabetic subjects). Sample race, gender, age, and the results of three autoantibody assays are shown as provided by the DASP. Protein concentration was measured by BCA assay.

| PNNL ID | CDC Unique ID | Race | Sex | Age | % of all Assays Designating + For GAD in DASP 2007 | % of all Assays Designating + For IA2 in DASP 2007 | % of all Assays Designating + For IAA in DASP 2007 | Total [Protein] by BCA assay (ug/ul) |
|---|---|---|---|---|---|---|---|---|
| Blind_01 | 001C0Z3I | White | MALE | 21 | 88.46 | 95.12 | 100.00 | 85.1 |
| Blind_02 | 001C08Y3 | C | male | 13 | 98.08 | 87.80 | 22.73 | 83.6 |
| Blind_03 | 001BY5V4 | White | MALE | 18 | 0.00 | 0.00 | 0.00 | 76.0 |
| Blind_04 | 001BZ28P | cauc | male | 9 | 98.04 | 34.15 | 36.36 | 42.2 |
| Blind_05 | 001BZR9C | White | MALE | 19 | 1.92 | 2.44 | 0.00 | 79.0 |
| Blind_06 | 001BXMWX | cauc | male | 12 | 44.23 | 100.00 | 72.73 | 97.6 |

TABLE 7-continued

Clinical data for the blind DASP cohort (10 control and 10 type 1 diabetic subjects). Sample race, gender, age, and the results of three autoantibody assays are shown as provided by the DASP. Protein concentration was measured by BCA assay.

| PNNL ID | CDC Unique ID | Race | Sex | Age | % of all Assays Designating + For GAD in DASP 2007 | % of all Assays Designating + For IA2 in DASP 2007 | % of all Assays Designating + For IAA in DASP 2007 | Total [Protein] by BCA assay (ug/ul) |
|---|---|---|---|---|---|---|---|---|
| Blind_07 | 001BZJZO | cauc | female | 10 | 98.08 | 100.00 | 95.45 | 66.7 |
| Blind_08 | 001C0JGH | C | female | 15 | 63.46 | 0.00 | 4.55 | 67.5 |
| Blind_09 | 001BZ41N | White | MALE | 20 | 1.92 | 0.00 | 0.00 | 74.2 |
| Blind_10 | 001C0OZA | White | MALE | 23 | 0.00 | 0.00 | 0.00 | 78.3 |
| Blind_11 | 001BY6PC | White | FEMALE | 18 | 0.00 | 0.00 | 4.55 | 84.9 |
| Blind_12 | 001C0ILU | cauc | female | 8 | 90.38 | 4.88 | 40.91 | 79.8 |
| Blind_13 | 001C09PX | White | MALE | 19 | 0.00 | 0.00 | 0.00 | 98.5 |
| Blind_14 | 001BXS9D | Black | MATE | 19 | 1.92 | 0.00 | 13.64 | 77.1 |
| Blind_15 | 001BZSEN | C | male | 14 | 98.04 | 97.56 | 63.64 | 81.6 |
| Blind_16 | 001BXRGC | C | female | 5 | 98.08 | 0.00 | 22.73 | 80.5 |
| Blind_17 | 001C0IZE | Black | FEMALE | 21 | 1.92 | 0.00 | 4.55 | 77.2 |
| Blind_18 | 001BZTGJ | C | male | 14 | 94.23 | 21.95 | 9.52 | 78.8 |
| Blind_19 | 001BYAPT | C | female | 8 | 5.77 | 97.56 | 86.36 | 68.4 |
| Blind_20 | 001BZKYP | White | MALE | 18 | 1.92 | 0.00 | 0.00 | 78.9 |

Figure 5A:
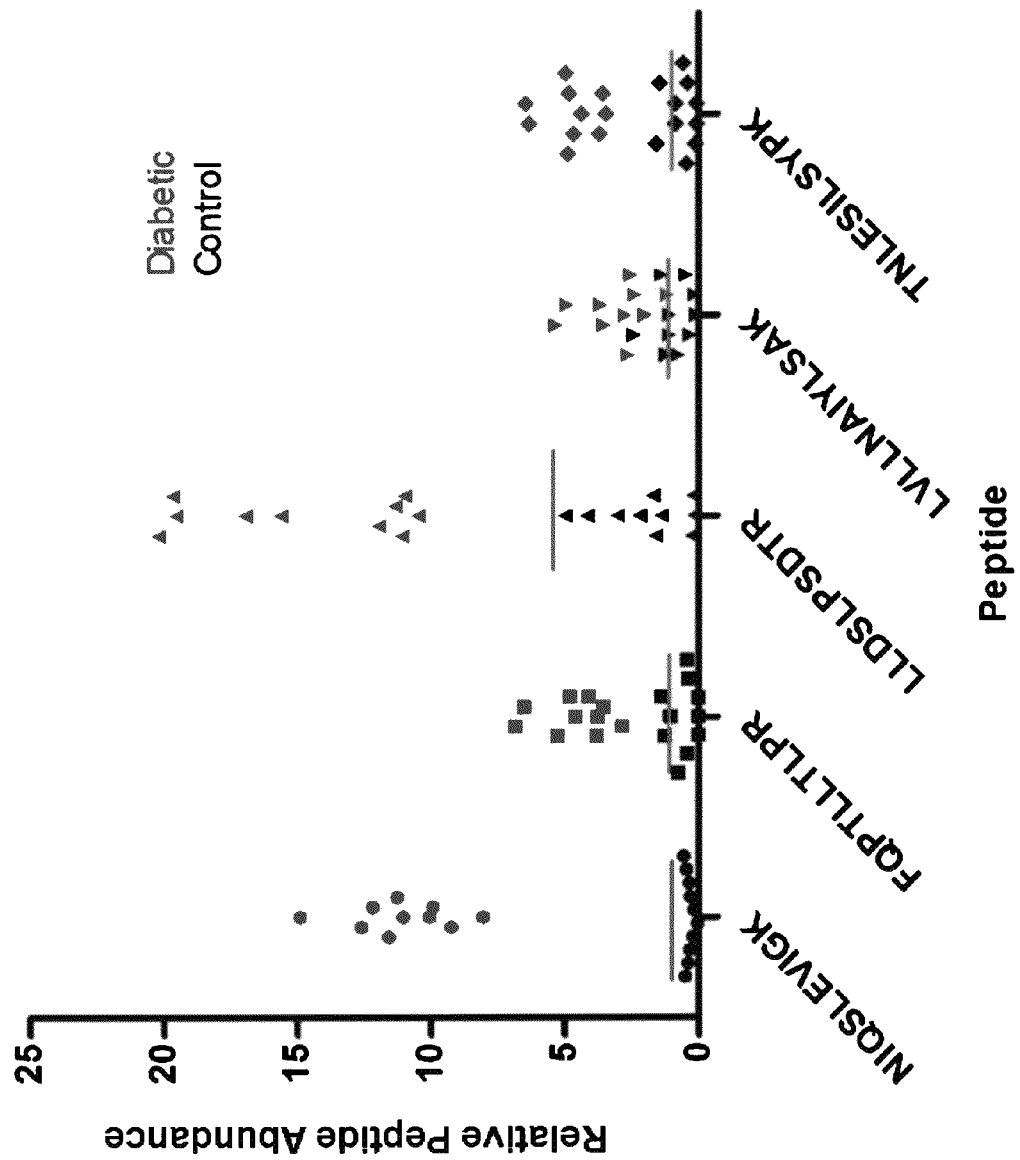
FIGS. 5a-c. Results of peptide assay performance in the blind DASP set (10 control and 10 T1DM subjects) after revealing of clinical status. Relative peptide abundance was used in the analyses. (a) Dot plot showing peptide abundance distributions and gaps between control and patient groups. Red lines represent the individual AS90 values that were calculated from the verification DASP cohort, which were used as thresholds to identify the blind samples. Only 5 peptides are shown, with peptide NIQSLEVIGK (SEQ ID NO: 41) from PPBP and the remaining four peptides from SERPING1 (SEQ ID NOS: 47-50, from left to right, respectively). (b) Fold change in abundance of each peptide, calculated by comparing the mean of peptide abundance in the type 1 diabetic state to that in control. Each column represents a unique peptide, and the peptides are grouped by gene name of each protein. The two dashed lines indicate fold changes of 1.5 and −1.5. As in FIGS. 4a-d, only 14 peptides representing 5 proteins are shown. The full results of all 52 peptides assays are in FIGS. 6a-c and Table 5. (c) Box-Whisker plots of each peptide shows the entire range of relative peptide abundances in control and type 1 diabetic groups, with the lower and upper lines of each box representing the $25^{th}$ and $75^{th}$ percentiles, respectively. The black and red horizontal lines within each box represent the median and mean values, respectively. The crossbars extend to the $10^{th}$ and $90^{th}$ percentile values, with outliers beyond this range shown as individual points. For each peptide, the left box plot represents the control group and the right box the patients. The sequences on the x-axis are shown in SEQ ID NOS: 23, 24, 25, 37, 38, 39, 40, 41, 47, 48, 49, 50, 51, and 52, respectively.
Figure 5B:
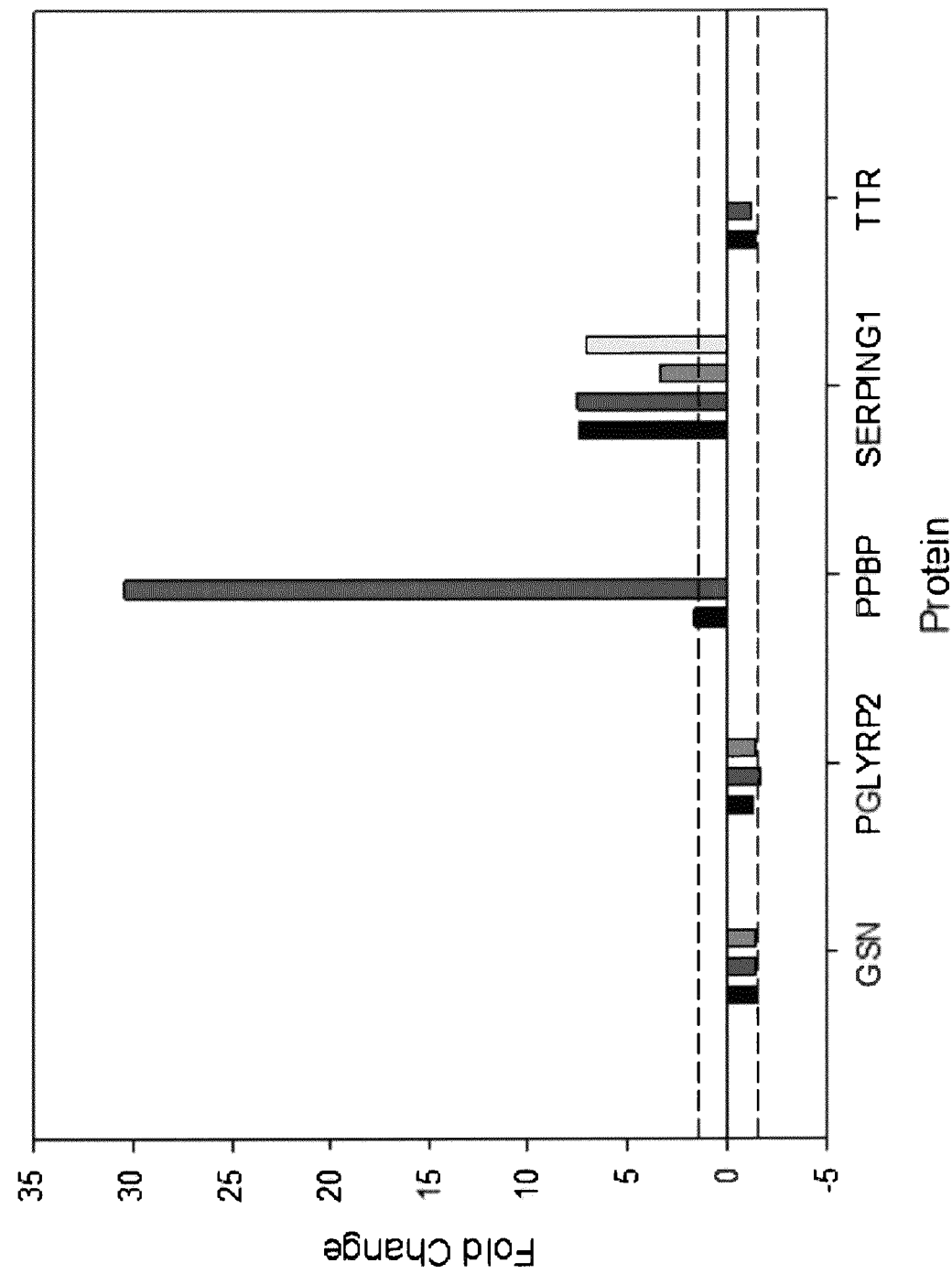
Figure 5C:
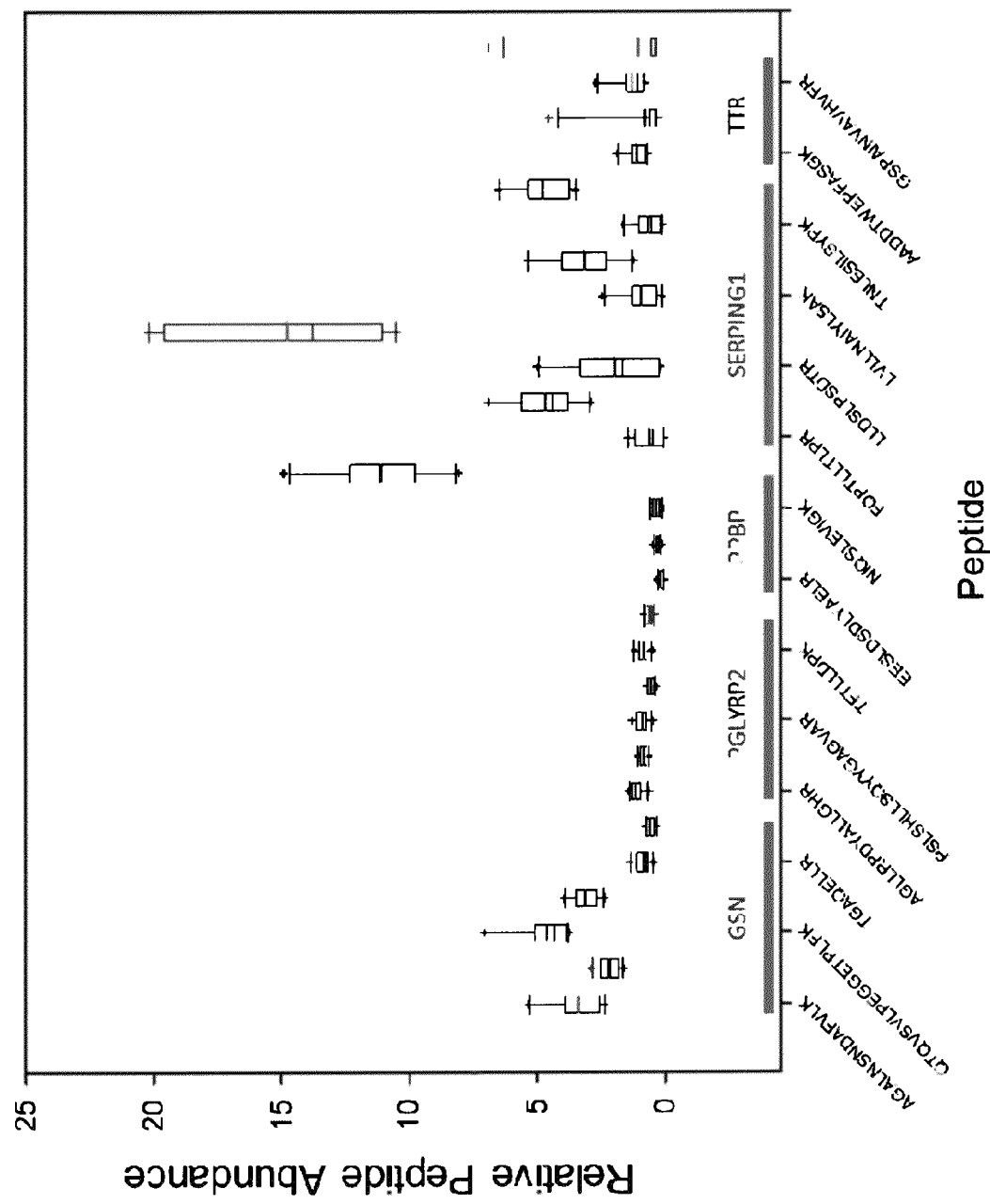
Figure 6B:
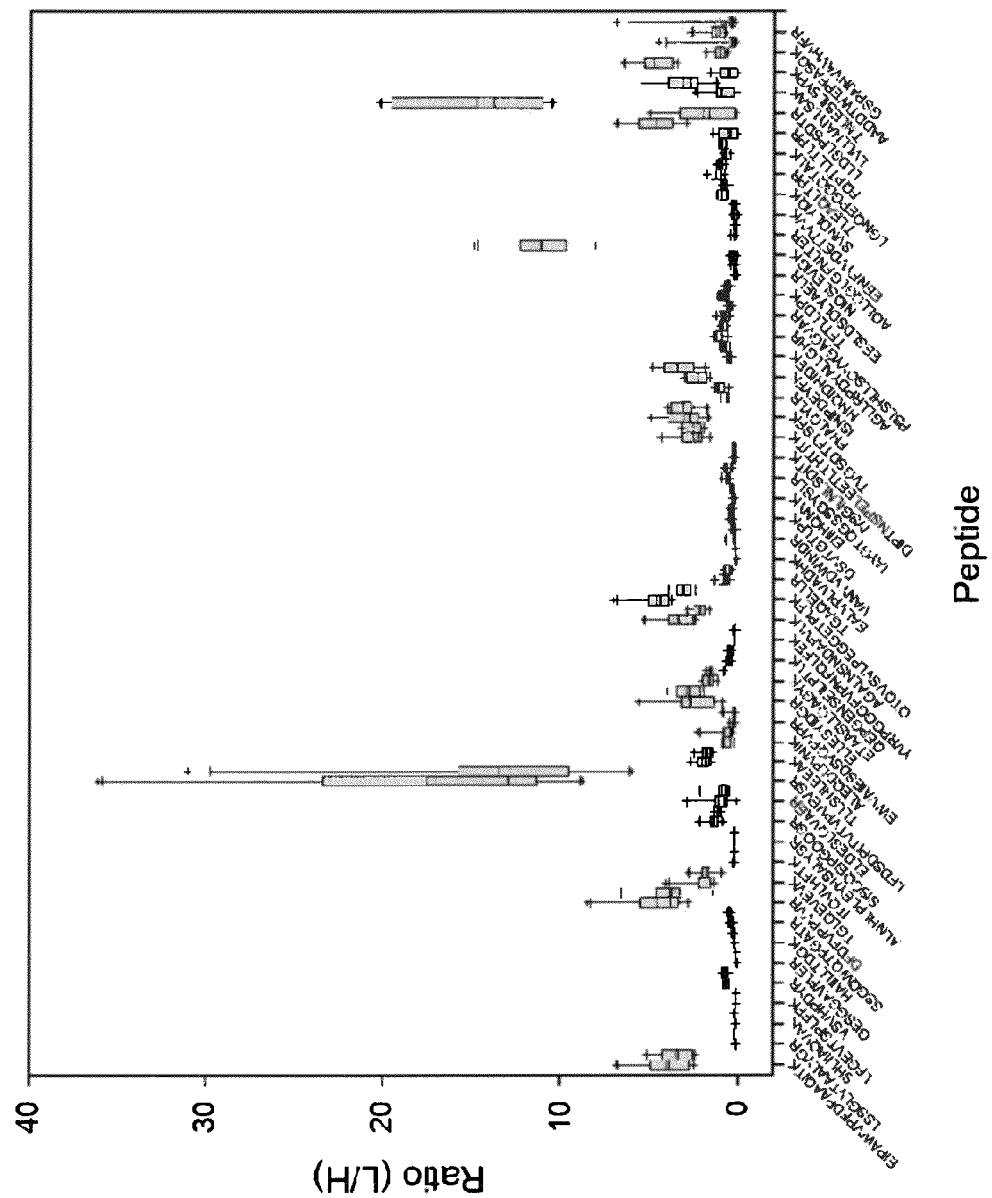

Using this approach, the 14 peptides from the 5 aforementioned proteins showed both sensitivity and specificity greater than 60%, with 7 peptides having both parameters greater than 80%. Two peptides, NIQSLEVIGK (SEQ ID NO: 41) and LLDSLPSDTR (SEQ ID NO: 48), achieved both 100% sensitivity and specificity (FIGS. 5a-5c). As shown in FIG. 5a, if the cut-off values were slightly adjusted, then two more peptides (FQPTLLTLPR and TNLESILSYPK SEQ ID NOS: 47 and 50, respectfully) would also have achieved 100% sensitivity and specificity. Statistical analysis after unblinding showed that 12 peptides had AUC values >0.90, with 4 of these having AUCs of 1.0. For the peptides that are up-regulated in type 1 diabetic subjects, NIQSLEVIGK showed a dramatic increase of 30.4-fold (p=1.08E-5, U test), while 3 peptides in C1 inhibitor protein (SERPING1) all had a fold change of more than 7-fold (p=1.08E-5, U test). Full statistical analyses of these 20 blind samples are reported in Table 8 and FIGS. 6a-b.

TABLE 8

Statistical analysis of peptide abundances in the blind DASP cohort (10 control and 10 type 1 diabetic subjects) after revealing clinical status. Relative peptide abundances were used in the analysis and were represented by peak area ratios of the endogenous peptides to their SIS analogs. Calculations of mean, fold change, and Mann-Whitney U test were carried out in DAnTE, while areas under the curve (AUC) were calculated with the ROC toolbox in SigmaPlot.

| Protein | Peptide | Mean Abundance Patient | Mean Abundance Control | Fold Change | p-value (MWUT) | AUC |
|---|---|---|---|---|---|---|
| AZGP1 | EIPAWVPFDPAAQITK | 3.48 | 4.02 | -1.2 | 4.81E-01 | 0.60 |
| BTD | LSSGLVTAALYGR | 0.15 | 0.13 | 1.1 | 6.23E-01 | 0.57 |
| BTD | SHLIIAQVAK | 0.14 | 0.13 | 1.1 | 3.93E-01 | 0.62 |
| C1R | LFGEVTSPLFPK | 0.07 | 0.08 | -1.1 | 2.80E-01 | 0.65 |
| C1R | VSVHPDYR | 0.68 | 0.68 | 1.0 | 7.39E-01 | 0.55 |
| C2 | GESGGAVFLER | 0.05 | 0.05 | 1.1 | 2.47E-01 | 0.66 |
| C2 | HAIILLTDGK | 0.25 | 0.18 | 1.4 | 1.50E-03 | 0.90 |
| C2 | SSGQWQTPGATR | 0.49 | 0.35 | 1.4 | 5.20E-03 | 0.86 |
| C3 | DFDFVPPVVR | 3.85 | 4.56 | -1.2 | 5.79E-01 | 0.58 |
| C3 | TGLQEVEVK | 1.76 | 2.07 | -1.2 | 4.81E-01 | 0.60 |
| C4A | ITQVLHFTK | 0.18 | 0.19 | -1.1 | 9.71E-01 | 0.51 |
| C6 | ALNHLPLEYNSALYSR | 0.18 | 0.18 | 1.0 | 9.12E-01 | 0.52 |
| CFP | SISCQEIPGQQSR | 1.08 | 1.38 | -1.3 | 1.47E-02 | 0.82 |
| CLU | ELDESLQVAER | 0.90 | 1.02 | -1.1 | 4.81E-01 | 0.60 |
| CLU | LFDSDPITVTVPVEVSR | 13.50 | 17.52 | -1.3 | 2.80E-01 | 0.65 |
| CLU | TLLSNLEEAK | 1.81 | 1.95 | -1.1 | 4.36E-01 | 0.61 |

TABLE 8-continued

Statistical analysis of peptide abundances in the blind DASP cohort (10 control and 10 type 1 diabetic subjects) after revealing clinical status. Relative peptide abundances were used in the analysis and were represented by peak area ratios of the endogenous peptides to their SIS analogs. Calculations of mean, fold change, and Mann-Whitney U test were carried out in DAnTE, while areas under the curve (AUC) were calculated with the ROC toolbox in SigmaPlot.

| Protein | Peptide | Mean Abundance Patient | Mean Abundance Control | Fold Change | p-value (MWUT) | AUC |
|---|---|---|---|---|---|---|
| CNDP1 | ALEQDLPVNIK | 0.75 | 0.57 | 1.3 | 7.39E-01 | 0.55 |
| CNDP1 | EWVAIESDSVQPVPR | 0.30 | 0.25 | 1.2 | 1.00E+00 | 0.50 |
| F2 | ELLESYIDGR | 2.86 | 2.61 | 1.1 | 4.81E-01 | 0.60 |
| F2 | ETAASLLQAGYK | 1.40 | 1.68 | -1.2 | 8.92E-02 | 0.73 |
| GPX3 | QEPGENSEILPTLK | 0.47 | 0.52 | -1.1 | 2.47E-01 | 0.66 |
| GPX3 | YVRPGGGFVPNFQLFEK | 0.17 | 0.19 | -1.1 | 5.45E-01 | 0.58 |
| GSN | AGALNSNDAFVLK | 2.19 | 3.39 | -1.5 | 2.88E-03 | 0.88 |
| GSN | QTQVSVLPEGGETPLFK | 3.13 | 4.62 | -1.5 | 7.58E-05 | 0.97 |
| GSN | TGAQELLR | 0.60 | 0.84 | -1.4 | 2.88E-02 | 0.79 |
| HGFAC | EALVPLVADHK | 0.14 | 0.11 | 1.3 | 3.11E-02 | 0.79 |
| HGFAC | VANYVDWINDR | 0.21 | 0.24 | -1.1 | 6.84E-01 | 0.56 |
| KLKB1 | DSVTGTLPK | 0.41 | 0.38 | 1.1 | 4.36E-01 | 0.61 |
| KLKB1 | EIIIHQNYK | 0.33 | 0.28 | 1.2 | 7.53E-02 | 0.74 |
| KLKB1 | IAYGTQGSSGYSLR | 0.65 | 0.67 | -1.0 | 8.53E-01 | 0.53 |
| KLKB1 | IYSGILNLSDITK | 0.25 | 0.25 | 1.0 | 7.96E-01 | 0.54 |
| KNG1 | DIPTNSPELEETLTHTITK | 2.55 | 2.56 | -1.0 | 5.29E-01 | 0.59 |
| KNG1 | TVGSDTFYSFK | 3.12 | 3.10 | 1.0 | 6.84E-01 | 0.56 |
| LUM | FNALQYLR | 1.04 | 0.66 | 1.6 | 2.09E-03 | 0.89 |
| LUM | ISNIPDEYFK | 3.37 | 2.25 | 1.5 | 6.84E-03 | 0.85 |
| LUM | NNQIDHIDEK | 0.81 | 0.51 | 1.6 | 7.25E-04 | 0.92 |
| PGLYRP2 | AGLLRPDYALLGHR | 0.86 | 1.12 | -1.3 | 6.84E-03 | 0.85 |
| PGLYRP2 | PSLSHLLSQYYGAGVAR | 0.55 | 0.91 | -1.6 | 4.87E-04 | 0.93 |
| PGLYRP2 | TFTLLDPK | 0.61 | 0.85 | -1.4 | 6.84E-03 | 0.85 |
| PPBP | EESLDSDLYAELR | 0.25 | 0.15 | 1.6 | 4.93E-02 | 0.76 |
| PPBP | NIQSLEVIGK | 11.10 | 0.37 | 30.4 | 1.08E-05 | 1.00 |
| SERPINA6 | AQLLQGLGFNLTER | 0.21 | 0.27 | -1.3 | 2.88E-02 | 0.79 |
| SERPINA6 | EENFYVDETTVVK | 0.25 | 0.26 | -1.0 | 6.84E-01 | 0.56 |
| SERPIND1 | SVNDLYIQK | 0.79 | 0.92 | -1.2 | 1.65E-01 | 0.69 |
| SERPIND1 | TLEAQLTPR | 1.06 | 1.27 | -1.2 | 1.23E-01 | 0.71 |
| SERPINF2 | LGNQEPGGQTALK | 1.00 | 0.72 | 1.4 | 7.25E-04 | 0.92 |
| SERPING1 | FQPTLLTLPR | 4.66 | 0.63 | 7.4 | 1.08E-05 | 1.00 |
| SERPING1 | LLDSLPSDTR | 14.78 | 1.98 | 7.5 | 1.08E-05 | 1.00 |
| SERPING1 | LVLLNAIYLSAK | 3.13 | 0.94 | 3.3 | 2.06E-04 | 0.95 |
| SERPING1 | TNLESILSYPK | 4.75 | 0.67 | 7.1 | 1.08E-05 | 1.00 |

TABLE 8-continued

Statistical analysis of peptide abundances in the blind DASP cohort (10 control and 10 type 1 diabetic subjects) after revealing clinical status. Relative peptide abundances were used in the analysis and were represented by peak area ratios of the endogenous peptides to their SIS analogs. Calculations of mean, fold change, and Mann-Whitney U test were carried out in DAnTE, while areas under the curve (AUC) were calculated with the ROC toolbox in SigmaPlot.

| Protein | Peptide | Mean Abundance Patient | Mean Abundance Control | Fold Change | p-value (MWUT) | AUC |
|---|---|---|---|---|---|---|
| TTR | AADDTWEPFASGK | 0.81 | 1.11 | -1.4 | 1.50E-03 | 0.90 |
| TTR | GSPAINVAVHVFR | 1.04 | 1.27 | -1.2 | 1.50E-03 | 0.90 |

The peptide to protein inference is a general problem in bottom-up proteomics,[32] particularly with respect to human blood samples, where very complex alternate splicing, in vivo proteolytic processing and post-translational modifications occur on protein precursors. BLAST was used to ensure that each of the 52 peptides chosen is unique to only one gene name. The calculations of protein concentrations based on SIS peptides in general agree with the literature survey[33] or with similar MRM types of protein concentration measurement (Table 9)[27]. The results herein show that peptides belonging to the same protein had similar abundances, except for the three peptides of clusterin, where peptide TLLSNLEEAK belongs to the α chain, and peptides ELDESLQVAER and LFDSDPITVTVPVEVSR belong to the β chain.

TABLE 9

Absolute protein concentrations calculated herein, as compared to the protein concentrations reported in Kuzyk et al. (27) and Hortin et al. (33). Absolute protein concentrations were represented by the peptide concentration values of each of their constituative peptides and averaged across all the samples in the same group.

| Acc_UniProt | Protein | Peptide | [Control] (µM) | [Patient] (µM) | Concentration (µM) by Kuzyk | Concentration (µM) by Hortin |
|---|---|---|---|---|---|---|
| P25311 | AZGP1 | EIPAWVPFDPAAQITK | 1.83 | 1.58 | 3.16 | 1.2 |
| P43251 | BTD | LSSGLVTAALYGR | 0.11 | 0.10 | | N/A |
| P43251 | BTD | SHLIIAQVAK | 0.11 | 0.10 | | N/A |
| P00736 | C1R | LFGEVTSPLFPK | 0.07 | 0.04 | | 1 |
| P00736 | C1R | VSVHPDYR | 0.43 | 0.39 | | 1 |
| P06681 | C2 | GESGGAVFLER | 0.07 | 0.06 | | 0.2 |
| P06681 | C2 | HAIILLTDGK | 0.18 | 0.17 | | 0.2 |
| P06681 | C2 | SSGQWQTPGATR | 0.19 | 0.24 | | 0.2 |
| P01024 | C3 | DFDFVPPVVR | 6.99 | 4.20 | 22.64 | 7.5 |
| P01024 | C3 | TGLQEVEVK | 6.68 | 3.82 | 22.64 | 7.5 |
| P0C0L4 | C4A | ITQVLHFTK | 2.19 | 1.34 | | 0.65 |
| P13671 | C6 | ALNHLPLEYNSALYSR | 0.48 | 0.36 | | 0.7 |
| P27918 | CFP | SISCQEIPGQQSR | 0.41 | 0.25 | | 0.4 |
| P10909 | CLU | ELDESLQVAER | 7.03 | 5.83 | 2.62 | 1.55 |
| P10909 | CLU | LFDSDPITVTVPVEVSR | 16.68 | 13.60 | 2.62 | 1.55 |
| P10909 | CLU | TLLSNLEEAK | 0.84 | 0.62 | 2.62 | 1.55 |
| Q96KN2 | CNDP1 | ALEQDLPVNIK | 0.08 | 0.09 | | N/A |
| Q96KN2 | CNDP1 | EWVAIESDSVQPVPR | 0.13 | 0.16 | | N/A |
| P00734 | F2 | ELLESYIDGR | 1.62 | 1.20 | 1.48 | 1.5 |
| P00734 | F2 | ETAASLLQAGYK | 1.20 | 0.76 | 1.48 | 1.5 |
| P22352 | GPX3 | QEPGENSEILPTLK | 0.26 | 0.22 | | 0.8 |
| P22352 | GPX3 | YVRPGGGFVPNFQLFEK | 0.17 | 0.13 | | 0.8 |

TABLE 9-continued

Absolute protein concentrations calculated herein, as compared to the protein concentrations reported in Kuzyk et al. (27) and Hortin et al. (33). Absolute protein concentrations were represented by the peptide concentration values of each of their constituative peptides and averaged across all the samples in the same group.

| Acc_UniProt | Protein | Peptide | [Control] (µM) | [Patient] (µM) | Concentration (µM) by Kuzyk | Concentration (µM) by Hortin |
|---|---|---|---|---|---|---|
| P06396 | GSN | AGALNSNDAFVLK | 1.07 | 0.78 | 1.63 | 3.75 |
| P06396 | GSN | QTQVSVLPEGGETPLFK | 2.43 | 1.79 | 1.63 | 3.75 |
| P06396 | GSN | TGAQELLR | 0.85 | 0.58 | 1.63 | 3.75 |
| Q04756 | HGFAC | EALVPLVADHK | 0.09 | 0.07 | | N/A |
| Q04756 | HGFAC | VANYVDWINDR | 0.10 | 0.13 | | N/A |
| P03952 | KLKB1 | DSVTGTLPK | 0.47 | 0.36 | | 0.6 |
| P03952 | KLKB1 | EIIIHQNYK | 0.23 | 0.19 | | 0.6 |
| P03952 | KLKB1 | IAYGTQGSSGYSLR | 0.44 | 0.39 | | 0.6 |
| P03952 | KLKB1 | IYSGILNLSDITK | 0.17 | 0.16 | | 0.6 |
| P01042 | KNG1 | DIPTNSPELEETLTHTITK | 5.10 | 4.12 | 3.94 | 3 |
| P01042 | KNG1 | TVGSDTFYSFK | 3.64 | 2.74 | 3.94 | 3 |
| P51884 | LUM | FNALQYLR | 0.55 | 0.53 | | N/A |
| P51884 | LUM | ISNIPDEYFK | 0.86 | 0.82 | | N/A |
| P51884 | LUM | NNQIDHIDEK | 0.37 | 0.37 | | N/A |
| Q96PD5 | PGLYRP2 | AGLLRPDYALLGHR | 0.67 | 0.44 | | N/A |
| Q96PD5 | PGLYRP2 | PSLSHLLSQYYGAGVAR | 0.58 | 0.38 | | N/A |
| Q96PD5 | PGLYRP2 | TFTLLDPK | 0.59 | 0.39 | | N/A |
| P02775 | PPBP | EESLDSDLYAELR | 0.25 | 0.40 | | N/A |
| P02775 | PPBP | NIQSLEVIGK | 0.13 | 1.06 | | N/A |
| P08185 | SERPINA6 | AQLLQGLGFNLTER | 0.51 | 0.35 | | 1.4 |
| P08185 | SERPINA6 | EENFYVDETTVVK | 2.06 | 1.79 | | 1.4 |
| P05546 | SERPIND1 | SVNDLYIQK | 0.86 | 0.58 | | 1.5 |
| P05546 | SERPIND1 | TLEAQLTPR | 1.04 | 0.70 | | 1.5 |
| P08697 | SERPINF2 | LGNQEPGGQTALK | 0.70 | 0.71 | 2.20 | 1 |
| P05155 | SERPING1 | FQPTLLTLPR | 0.31 | 0.79 | | 2.65 |
| P05155 | SERPING1 | LLDSLPSDTR | 0.30 | 0.62 | | 2.65 |
| P05155 | SERPING1 | LVLLNAIYLSAK | 0.90 | 1.42 | | 2.65 |
| P05155 | SERPING1 | TNLESILSYPK | 0.34 | 0.76 | | 2.65 |
| P02766 | TTR | AADDTWEPFASGK | 4.79 | 2.84 | 11.86 | 22.5 |
| P02766 | TTR | GSPAINVAVHVFR | 5.10 | 3.06 | 11.86 | 22.5 |

Figure 2B:
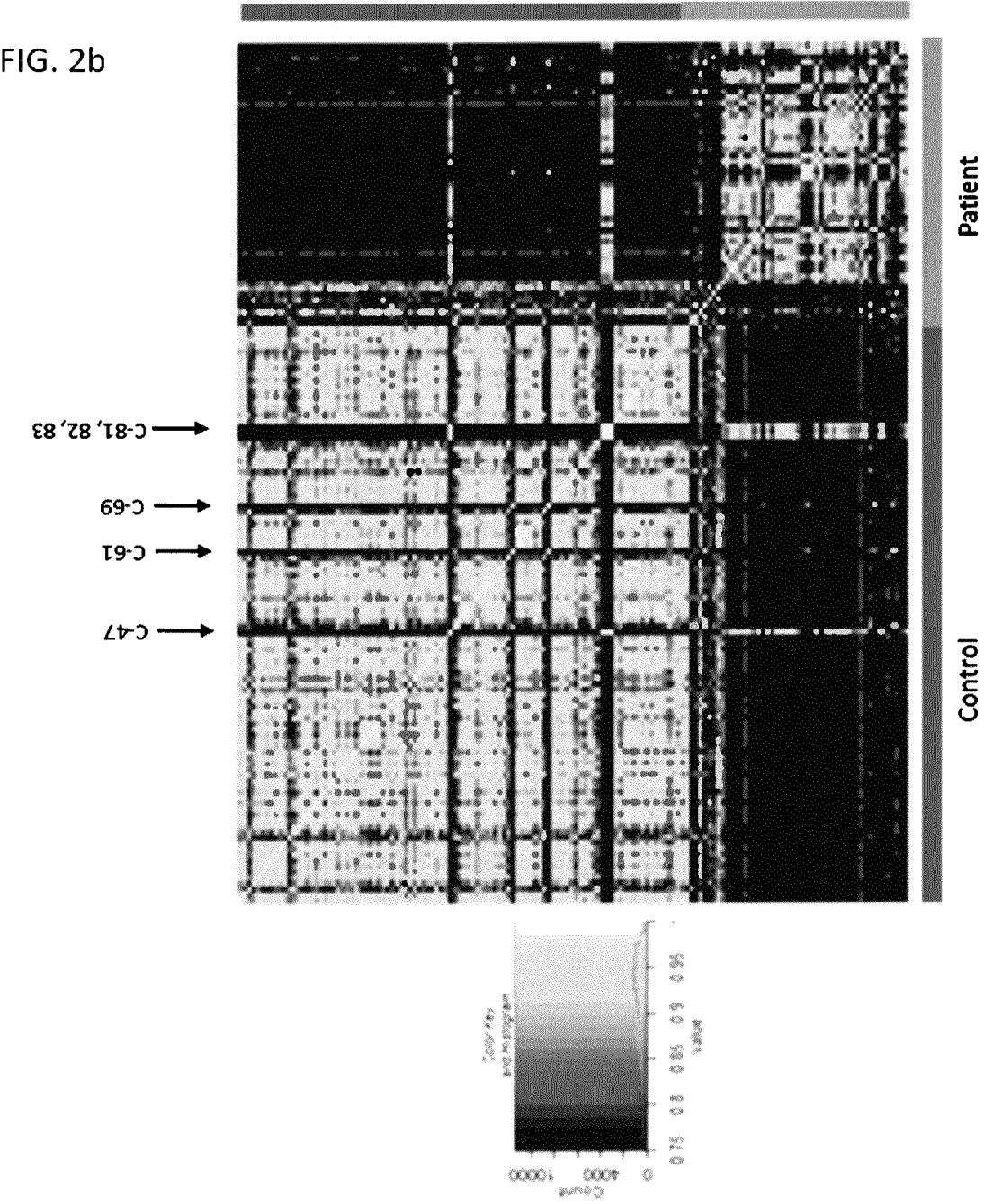

The majority of the samples in the DASP verification set are sera while a few are plasma, as we have determined using a sandwich micro ELISA assay[34] (Table 1). In addition, there are 8 patient samples collected using plasmapheresis procedures, and our ELISA assay showed them to be plasma. Except for these 8 samples, the sample type (serum or plasma) doesn't affect the performance of our peptide assays. The values of the target peptides in the 6 outliers that we have identified in the control subjects using PLS and correlation plot analyses (FIGS. 2a and 2b) do not correlate with race, age, gender or with protein concentrations as measured by BCA assay (Table 3). In contrast, all of the plasmapheresis samples correlate poorly with the rest of the diabetic subjects, possibly due to the low concentration of total protein ($55.5 \pm 18.2$ µg/µL) in these samples compared with that of the rest of the group ($85.5 \pm 20.0$ µg/µL). However, the remaining diabetic samples showing poor correlation to other samples within the diabetic group do not correlate with race, age, gender or with protein concentration.

Currently, levels of GAD, IA-2 and insulin autoantibodies are the best markers for prognosis and diagnosis of T1DM;[21-23] however, it has been reported that people with high levels of these autoantobodies do not always progress to the diabetic state.[17,20,24] In general, for the samples in our study, diagnosis of diabetes correlates to the number of autoantibodies called positive, but there are some control subjects with high positivities of at least one of the three autoantibodies, while the autoantibody levels of two type 1 diabetic subjects were called negative by most of the DASP laboratories (Table 3). Of note, our peptide assay results are not totally dependent on the positivities of the autoantibody assays. For the two diabetic subjects having very negative autoantibody levels, our results showed that their levels of peptide NIQSLEVIGK are either above or slightly below the mean of this peptide in the diabetic group. Conversely, some of the control subjects with high positivities of GAD autoantibody assay had very low levels of this peptide. This clearly indicates that the peptide biomarkers identified in our study are orthogonal to the widely accepted autoantibody assays.

In its mature form, PPBP precursor can be proteolytically cleaved into 10 polypeptide chains with different functions (FIG. 7). Of note, the two peptides that were chosen to represent PPBP have sharp differences in the level of up-regulation in type 1 diabetic subjects, with EESLDSDLYAELR (amino acids 50-62, SEQ ID NO: 40) only having a modest increase of 1.6-fold in both the DASP verification and blind set, while NIQSLEVIGK (amino acids 76-85, SEQ ID NO: 41)) showing a dramatic up-regulation of 8.5-fold in the DASP verification set (if outlier samples had been excluded in the statistical analysis, then the fold change would be 23.5-fold.) and 30.4-fold in the blind set. Also, peptide EESLDSDLYAELR (SEQ ID NO: 40) exists exclusively in two forms of CTAPIII, and in TC-2 and beta-TG, while peptide NIQSLEVIGK (SEQ ID NO: 41) exists in all forms of these proteins, in addition to TC-1 and the five forms of NAP-2 (FIG. 7) indicating that TC-1/NAP-2 are the major sources of this latter peptide. TC-1 is an antibacterial protein released from activated platelet alpha-granules as part of the innate immune response,[35] while the NAP-2s are activators for neutrophils and can be generated from proteolytic cleavage of both CTAPIII and PPBP by tissue proteases.[36] These results indicate that innate immunity is involved in the pathogenesis of T1DM.

Plasma protease C1 inhibitor (SERPING1) was identified as a sensitive marker for diagnosing T1DM, and three [FQPTLLTLPR (amino acids 391-400; SEQ ID NO: 47), LLDSLPSDTR (amino acids 287-298; SEQ ID NO: 48), and TNLESILSYPK (amino acids 191-201; SEQ ID NO: 50)] of the four peptides agree better with each other in both the DASP verification (2.3-fold difference on average) and blind sets (7.3-fold on average) than with the remaining peptide (LVLLNAIYLSAK (amino acids 277-286; SEQ ID NO: 49), which always had lower fold changes in both cases (1.6-fold and 3.3-fold in the DASP verification and blind sets, respectively). The reason for this difference is not known. Indeed, peptide sequences were selected that are not known to contain post-translational modifications, although this protein is known to be heavily glycosylated. The main function of C1 inhibitor is controlling the activation of C1 complex (C1r, C1s and MASP2) in suppression of inflammation.[38,39] In this respect, the two peptides (LFGEVTSPLFPK and VSVHPDYR; SEQ ID NOS: 4 and 5, respectively) representing C1r were only slightly (~1.1- to 1.5-fold) down-regulated in the type 1 diabetic individuals (Tables 3 and 5). However, these two peptides exist in both activated and inactivated forms of C1r; therefore, the measurement reflects the total concentration of C1r. Alternatively, C1 inhibitor can interact with infectious agents. E. coli can bind C1-inhibitor through its stcE protein, which allows it to localize onto cell membranes thus protecting the bacteria against complement-mediated lysis.[40]

In both the DASP verification and blind set, consistent down-regulation of proteins GSN, PGLYRP2 and TTR were observed. With its main function in actin scavenging, gelsolin (GSN) also binds inflammatory mediators such as platelet activating factors to localize inflammation and blunt its systemic effects.[41] Depleted plasma gelsolin levels have been observed in diverse states of acute injury and inflammation.[42] As an innate immunity protein, human peptidoglycan recognition protein 2 (PGLYRP2) is an N-acetylmuramoyl-1-alanine amidase that hydrolyzes bacterial peptidoglycan, is constitutively produced in the liver and secreted into the blood, and is also induced by bacteria in epithelial cells.[43] It was suggested that this amidase eliminates proinflammatory peptidoglycan and thus prevents over-activation of the immune system leading to excessive inflammation.[44] Transthyretin (TTR) is a serum and cerebrospinal fluid carrier of the thyroid hormone thyroxine, retinol and many other compounds, and decreases in its levels is a sensitive biomarker of malnutrition in acute and chronic pancreatitis.[45] TTR also protects against beta-cell apoptosis and promotes glucose-induced increases in insulin release. Conversion of TTR tetramer to monomer may be involved in the development of beta-cell failure/destruction in T1DM.[46]

Taken together, the results provided herein demonstrate the power of LC-MS-based proteomics technologies in the discovery and validation of peptide markers of T1DM from human blood serum and plasma. These surrogate peptide markers are independent of the commonly used autoantibody assays, and furthermore the proteins to which they correspond indicate that processes in the innate immune response are severely perturbed in this disease. This is the first report that systemic, proteome-level dysregulation of innate immunity is a characteristic of T1DM, which sheds new light on the pathogenesis of this disease and provides new strategies in prognosis, intervention and prevention of T1DM.

REFERENCES

1. Knip, M. & Siljander, H. Autoimmune mechanisms in type 1 diabetes. *Autoimmun Rev* 7, 550-557 (2008).
2. Mathis et al., C. beta-Cell death during progression to diabetes. *Nature* 414, 792-798 (2001).
3. Tisch & McDevitt, Insulin-dependent diabetes mellitus. *Cell* 85, 291-297 (1996).
4. Atkinson, M. A. & Eisenbarth, G. S. Type 1 diabetes: new perspectives on disease pathogenesis and treatment. *Lancet* 358, 221-229 (2001).
5. Vehik, K. & Dabelea, D. The changing epidemiology of type 1 diabetes: why is it going through the roof? *Diabetes-Metab Res* 27, 3-13 (2011).
6. Hagopian, W. A., et al. The Environmental Determinants of Diabetes in the Young (TEDDY): genetic criteria and international diabetes risk screening of 421 000 infants. *Pediatr Diabetes* (2011).
7. Horn et al., Allelic sequence variation of the HLA-DQ loci: relationship to serology and to insulin-dependent diabetes susceptibility. *Proc Natl Acad Sci U S A* 85, 6012-6016 (1988).

8. Sheehy et al., A diabetes-susceptible HLA haplotype is best defined by a combination of HLA-DR and -DQ alleles. *The Journal of clinical investigation* 83, 830-835 (1989).
9. Knip et al., Environmental triggers and determinants of type 1 diabetes. *Diabetes* 54 Suppl 2, S125-136 (2005).
10. Foxman & Iwasaki, Genome-virome interactions: examining the role of common viral infections in complex disease. *Nat Rev Microbiol* 9, 254-264 (2011).
11. Hober, D. & Sauter, P. Pathogenesis of type 1 diabetes mellitus: interplay between enterovirus and host. *Nat Rev Endocrinol* 6, 279-289 (2010).
12. Pietropaolo et al., Primer: immunity and autoimmunity. *Diabetes* 57, 2872-2882 (2008).
13. Jun, H. S. & Yoon, J. W. A new took at viruses in type 1 diabetes. *Diabetes-Metab Res* 19, 8-31 (2003).
14. Stene et al., Enterovirus infection and progression from islet autoimmunity to type 1 diabetes: the Diabetes and Autoimmunity Study in the Young (DAISY). *Diabetes* 59, 3174-3180 (2010).
15. Knip, M. Natural course of preclinical type 1 diabetes. *Horm Res* 57 Suppl 1, 6-11 (2002).
16. Wenzlau et al., The cation efflux transporter ZnT8 (Slc30A8) is a major autoantigen in human type 1 diabetes. *Proc Natl Acad Sci USA* 104, 17040-17045 (2007).
17. Barker, J. M., et al. Prediction of autoantibody positivity and progression to type 1 diabetes: Diabetes Autoimmunity Study in the Young (DAISY). *J Clin Endocrinol Metab* 89, 3896-3902 (2004).
18. Bingley et al., Diabetes Antibody Standardization Program: first assay proficiency evaluation. *Diabetes* 52, 1128-1136 (2003).
19. Mueller et al., Predicting Type 1 Diabetes Using Autoantibodies: The Latest Results from the Diabetes Autoantibody Standardization Program. *DIABETES TECHNOLOGY & THERAPEUTICS* 4, 397-400 (2002).
20. Siljander et al., Prediction of type 1 diabetes among siblings of affected children and in the general population. *Diabetologia* 50, 2272-2275 (2007).
21. Schlosser et al., Diabetes Antibody Standardization Program: evaluation of assays for insulin autoantibodies. *Diabetologia* 53, 2611-2620 (2010).
22. Torn et al., Diabetes Antibody Standardization Program: evaluation of assays for autoantibodies to glutamic acid decarboxylase and islet antigen-2. *Diabetologia* 51, 846-852 (2008).
23. Bingley, P. J., et al. Measurement of islet cell antibodies in the Type 1 Diabetes Genetics Consortium: efforts to harmonize procedures among the laboratories. *Clin Trials* 7, S56-64 (2010).
24. Bingley et al., Prediction of IDDM in the general population: strategies based on combinations of autoantibody markers. *Diabetes* 46, 1701-1710 (1997).
25. Metz et al., Application of proteomics in the discovery of candidate protein biomarkers in a diabetes autoantibody standardization program sample subset. *J Proteome Res* 7, 698-707 (2008).
26. Anderson & Hunter, Quantitative mass spectrometric multiple reaction monitoring assays for major plasma proteins. *Mol Cell Proteomics* 5, 573-588 (2006).
27. Kuzyk et al., Multiple reaction monitoring-based, multiplexed, absolute quantitation of 45 proteins in human plasma. *Mol Cell Proteomics* 8, 1860-1877 (2009).
28. Maclean et al., Effect of collision energy optimization on the measurement of peptides by selected reaction monitoring (SRM) mass spectrometry. *Anal Chem* 82, 10116-10124 (2010).
29. Picotti et al., High-throughput generation of selected reaction-monitoring assays for proteins and proteomes. *Nat Methods* 7, 43-46 (2010).
30. Schiess et al., Targeted proteomic strategy for clinical biomarker discovery. *Mol Oncol* 3, 33-44 (2009).
31. Zimmer et al., Advances in proteomics data analysis and display using an accurate mass and time tag approach. *Mass Spectrom Rev* 25, 450-482 (2006).
32. Nesvizhskii, A. I. & Aebersold, R. Interpretation of shotgun proteomic data: the protein inference problem. *Mol Cell Proteomics* 4, 1419-1440 (2005).
33. Hortin et al., High-abundance polypeptides of the human plasma proteome comprising the top 4 logs of polypeptide abundance. *Clin Chem* 54, 1608-1616 (2008).
34. Gonzalez et al., Development of a fibrinogen-specific sandwich enzyme-linked immunosorbent assay microarray assay for distinguishing between blood plasma and serum samples. *Anal Biochem* 414, 99-102 (2011).
35. Krijgsveld, J., et al. Thrombocidins, microbicidal proteins from human blood platelets, are C-terminal deletion products of CXC chemokines. *J Biol Chem* 275, 20374-20381 (2000).
36. Walz, A. & Baggiolini, M. Generation of the neutrophil-activating peptide NAP-2 from platelet basic protein or connective tissue-activating peptide III through monocyte proteases. *J Exp Med* 171, 449-454 (1990).
37. Roep, B. O. The role of T-cells in the pathogenesis of Type 1 diabetes: from cause to cure. *Diabetologia* 46, 305-321 (2003).
38. Davis, A. E., 3rd, Mejia, P. & Lu, F. Biological activities of C1 inhibitor. *Mol Immunol* 45, 4057-4063 (2008).
39. Stoermer, K. A. & Morrison, T. E. Complement and viral pathogenesis. *Virology* 411, 362-373 (2011).
40. Lathem, W. W., Bergsbaken, T. & Welch, R. A. Potentiation of C1 esterase inhibitor by StcE, a metalloprotease secreted by *Escherichia coli* O157:H7. *J Exp Med* 199, 1077-1087 (2004).
41. Bucki et al., Plasma gelsolin: function, prognostic value, and potential therapeutic use. *Curr Protein Pept Sci* 9, 541-551 (2008).
42. Smith et al., Decreased plasma gelsolin levels in patients with *Plasmodium falciparum* malaria: a consequence of hemolysis? *Blood* 72, 214-218 (1988).
43. Dziarski, R. & Gupta, D. The peptidoglycan recognition proteins (PGRPs). *Genome biology* 7, 232 (2006).
44. Hoijer et al., Inflammatory properties of peptidoglycan are decreased after degradation by human N-acetylmuramyl-L-alanine amidase. *Eur Cytokine Netw* 8, 375-381 (1997).
45. Lasztity, N., Biro, L., Nemeth, E., Pap, A. & Antal, M. Protein status in pancreatitis—transthyretin is a sensitive biomarker of malnutrition in acute and chronic pancreatitis. *Clin Chem Lab Med* 40, 1320-1324 (2002).
46. Refai et al., Transthyretin constitutes a functional component in pancreatic beta-cell stimulus-secretion coupling. *Proc Natl Acad Sci USA* 102, 17020-17025 (2005).
47. Schutzer et al., Distinct cerebrospinal fluid proteomes differentiate post-treatment lyme disease from chronic fatigue syndrome. *PLoS ONE* 6, e17287 (2011).
48. Qian et al., Enhanced Detection of Low Abundance Human Plasma Proteins Using a Tandem IgY12-SuperMix Immunoaffinity Separation Strategy. *Molecular & Cellular Proteomics* 7, 1963-1973 (2008).
49. Livesay et al., Fully automated four-column capillary LC-MS system for maximizing throughput in proteomic analyses. *Anal Chem* 80, 294-302 (2008).

50. Petritis, K., et al. Improved peptide elution time prediction for reversed-phase liquid chromatography-MS by incorporating peptide sequence information. *Anal Chem* 78, 5026-5039 (2006).
51. Kiebel et al., PRISM: a data management system for high-throughput proteomics. *Proteomics* 6, 1783-1790 (2006).
52. Jaitly, N., et al. Decon2LS: An open-source software package for automated processing and visualization of high resolution mass spectrometry data. *BMC Bioinformatics* 10, 87 (2009).
53. Monroe, M. E., et al. VIPER: an advanced software package to support high-throughput LC-MS peptide identification. *Bioinformatics* 23, 2021-2023 (2007).
54. Jaitly, N., et al. Robust algorithm for alignment of liquid chromatography-mass spectrometry analyses in an accurate mass and time tag data analysis pipeline. *Anal Chem* 78, 7397-7409 (2006).
55. Polpitiya et al., DAnTE: a statistical tool for quantitative analysis of -omics data. *Bioinformatics* 24, 1556-1558 (2008).
56. Callister et al., Normalization approaches for removing systematic biases associated with mass spectrometry and label-free proteomics. *J Proteome Res* 5, 277-286 (2006).
57. Saeed et al., TM4 microarray software suite. *Methods Enzymol* 411, 134-193 (2006).
58. Zhang, Z. Prediction of low-energy collision-induced dissociation spectra of peptides. *Anal Chem* 76, 3908-3922 (2004).
59. MacLean et al., Skyline: an open source document editor for creating and analyzing targeted proteomics experiments. *Bioinformatics* 26, 966-968 (2010).

In view of the many possible embodiments to which the principles of the disclosure may be applied, it should be recognized that the illustrated embodiments are only examples of the disclosure and should not be taken as limiting the scope of the disclosure. Rather, the scope of the disclosure is defined by the following claims. We therefore claim as our invention all that comes within the scope and spirit of these claims.

We claim:

1. A method of detecting peptides in a human blood sample, comprising:

determining a quantity of at least eight peptides selected from the group consisting of the amino acid sequence shown in SEQ ID NO: 23, 24, 25, 37, 38, 39, 40, 41, 47, 48, 49, 50, 51, and 52 in the blood sample obtained from the human, wherein at least one of the eight peptides consists of the amino acid sequence shown in SEQ ID NO: 25, 38, 39, 40, or 50; and comparing the quantity of the at least eight peptides to a control representing expression for each of the at least eight peptides expected in a subject who does not have type 1 diabetes mellitus (T1DM); and determining if there is differential expression of the at least eight peptides between the blood sample and the control.

2. The method of claim 1 wherein the method comprises determining a quantity of all 14 peptides consisting of the amino acid sequence shown in SEQ ID NO: 23, 24, 25, 37, 38, 39, 40, 41, 47, 48, 49, 50, 51, and 52.

3. The method of claim 1 wherein determining a quantity of the at least eight peptides consists of determining a quantity of the peptides consisting of the amino acid sequence shown in SEQ ID NO: 37, 38, 39, 41, 47, 48, 49, and 50.

4. The method of claim 1 wherein the method comprises determining a quantity of at least eight peptides consisting of the amino acid sequence shown in SEQ ID NO: 37, 38, 39, 41, 47, 48, 49, and 50.

5. The method of claim 1 wherein determining the quantity of the at least 8 peptides comprises determining a quantity of at least one peptide consisting of the amino acid sequence shown in SEQ ID NO: 25, 38, 39, 40, or 50, in addition to a peptide sequence consisting of;

NIQSLEVIGK (SEQ ID NO: 41);
LLDSLPSDTR (SEQ ID NO: 48);
NIQSLEVIGK (SEQ ID NO: 41) and LLDSLPSDTR (SEQ ID NO: 48);
FQPTLLTLPR (SEQ ID NO: 47);
LVLLNAIYLSAK (SEQ ID NO: 49);
TNLESILSYPK (SEQ ID NO: 50);
FQPTLLTLPR (SEQ ID NO: 47), LLDSLPSDTR (SEQ ID NO: 48), LVLLNAIYLSAK (SEQ ID NO: 49), and TNLESILSYPK (SEQ ID NO: 50);
NIQSLEVIGK (SEQ ID NO: 41), FQPTLLTLPR (SEQ ID NO: 47), LLDSLPSDTR (SEQ ID NO: 48), LVLLNAIYLSAK (SEQ ID NO: 49), and TNLESILSYPK (SEQ ID NO: 50), or
combinations thereof.

6. The method of claim 1, wherein determining the quantity of the at least eight peptides comprises determining the quantity of at least one of the eight peptides consisting of the amino acid sequence shown in SEQ ID NO: 25, 38, 39, 40, or 50, wherein at least one of eight peptides are SEQ ID NO: 38 and 39, and the quantity of the peptide consisting of the amino acid sequence shown in SEQ ID NO: 37 is also determined.

7. The method of claim 1, wherein the blood sample is a serum or plasma sample.

8. The method of claim 1, wherein determining a quantity comprises a qualitative or quantitative determination.

9. The method of claim 1, wherein determining the quantity of at least eight peptides comprises analyzing the blood sample using liquid chromatography multiple reaction monitoring mass spectrometry (LC-MRM-MS).

10. The method of claim 1, wherein the determining step and/or the comparing step are performed on a suitably programmed computer.

11. The method of claim 1, further comprising providing an output showing the quantity of the at least eight peptides compared to the control.

* * * * *

SEQUENCE LISTING

```
<160> NUMBER OF SEQ ID NOS: 54

<210> SEQ ID NO 1
<211> LENGTH: 16
<212> TYPE: PRT
<213> ORGANISM: Homo sapiens

<400> SEQUENCE: 1

Glu Ile Pro Ala Trp Val Pro Phe Asp Pro Ala Ala Gln Ile Thr Lys
1               5                   10                  15

<210> SEQ ID NO 2
<211> LENGTH: 13
<212> TYPE: PRT
<213> ORGANISM: Homo sapiens

<400> SEQUENCE: 2

Leu Ser Ser Gly Leu Val Thr Ala Ala Leu Tyr Gly Arg
1               5                   10

<210> SEQ ID NO 3
<211> LENGTH: 10
<212> TYPE: PRT
<213> ORGANISM: Homo sapiens

<400> SEQUENCE: 3

Ser His Leu Ile Ile Ala Gln Val Ala Lys
1               5                   10

<210> SEQ ID NO 4
<211> LENGTH: 12
<212> TYPE: PRT
<213> ORGANISM: Homo sapiens

<400> SEQUENCE: 4

Leu Phe Gly Glu Val Thr Ser Pro Leu Phe Pro Lys
1               5                   10

<210> SEQ ID NO 5
<211> LENGTH: 8
<212> TYPE: PRT
<213> ORGANISM: Homo sapiens
```

```
<400> SEQUENCE: 5

Val Ser Val His Pro Asp Tyr Arg
1               5

<210> SEQ ID NO 6
<211> LENGTH: 11
<212> TYPE: PRT
<213> ORGANISM: Homo sapiens

<400> SEQUENCE: 6

Gly Glu Ser Gly Gly Ala Val Phe Leu Glu Arg
1               5                   10

<210> SEQ ID NO 7
<211> LENGTH: 10
<212> TYPE: PRT
<213> ORGANISM: Homo sapiens

<400> SEQUENCE: 7

His Ala Ile Ile Leu Leu Thr Asp Gly Lys
1               5                   10

<210> SEQ ID NO 8
<211> LENGTH: 12
<212> TYPE: PRT
<213> ORGANISM: Homo sapiens

<400> SEQUENCE: 8

Ser Ser Gly Gln Trp Gln Thr Pro Gly Ala Thr Arg
1               5                   10

<210> SEQ ID NO 9
<211> LENGTH: 10
<212> TYPE: PRT
<213> ORGANISM: Homo sapiens

<400> SEQUENCE: 9

Asp Phe Asp Phe Val Pro Pro Val Val Arg
1               5                   10

<210> SEQ ID NO 10
<211> LENGTH: 9
<212> TYPE: PRT
<213> ORGANISM: Homo sapiens

<400> SEQUENCE: 10

Thr Gly Leu Gln Glu Val Glu Val Lys
1               5

<210> SEQ ID NO 11
<211> LENGTH: 9
<212> TYPE: PRT
<213> ORGANISM: Homo sapiens

<400> SEQUENCE: 11

Ile Thr Gln Val Leu His Phe Thr Lys
1               5

<210> SEQ ID NO 12
<211> LENGTH: 16
<212> TYPE: PRT
<213> ORGANISM: Homo sapiens
```

<400> SEQUENCE: 12

Ala Leu Asn His Leu Pro Leu Glu Tyr Asn Ser Ala Leu Tyr Ser Arg
1               5                   10                  15

<210> SEQ ID NO 13
<211> LENGTH: 13
<212> TYPE: PRT
<213> ORGANISM: Homo sapiens

<400> SEQUENCE: 13

Ser Ile Ser Cys Gln Glu Ile Pro Gly Gln Gln Ser Arg
1               5                   10

<210> SEQ ID NO 14
<211> LENGTH: 11
<212> TYPE: PRT
<213> ORGANISM: Homo sapiens

<400> SEQUENCE: 14

Glu Leu Asp Glu Ser Leu Gln Val Ala Glu Arg
1               5                   10

<210> SEQ ID NO 15
<211> LENGTH: 17
<212> TYPE: PRT
<213> ORGANISM: Homo sapiens

<400> SEQUENCE: 15

Leu Phe Asp Ser Asp Pro Ile Thr Val Thr Val Pro Val Glu Val Ser
1               5                   10                  15

Arg

<210> SEQ ID NO 16
<211> LENGTH: 10
<212> TYPE: PRT
<213> ORGANISM: Homo sapiens

<400> SEQUENCE: 16

Thr Leu Leu Ser Asn Leu Glu Glu Ala Lys
1               5                   10

<210> SEQ ID NO 17
<211> LENGTH: 11
<212> TYPE: PRT
<213> ORGANISM: Homo sapiens

<400> SEQUENCE: 17

Ala Leu Glu Gln Asp Leu Pro Val Asn Ile Lys
1               5                   10

<210> SEQ ID NO 18
<211> LENGTH: 15
<212> TYPE: PRT
<213> ORGANISM: Homo sapiens

<400> SEQUENCE: 18

Glu Trp Val Ala Ile Glu Ser Asp Ser Val Gln Pro Val Pro Arg
1               5                   10                  15

<210> SEQ ID NO 19
<211> LENGTH: 10
<212> TYPE: PRT
<213> ORGANISM: Homo sapiens

```
<400> SEQUENCE: 19

Glu Leu Leu Glu Ser Tyr Ile Asp Gly Arg
1               5                   10

<210> SEQ ID NO 20
<211> LENGTH: 12
<212> TYPE: PRT
<213> ORGANISM: Homo sapiens

<400> SEQUENCE: 20

Glu Thr Ala Ala Ser Leu Leu Gln Ala Gly Tyr Lys
1               5                   10

<210> SEQ ID NO 21
<211> LENGTH: 14
<212> TYPE: PRT
<213> ORGANISM: Homo sapiens

<400> SEQUENCE: 21

Gln Glu Pro Gly Glu Asn Ser Glu Ile Leu Pro Thr Leu Lys
1               5                   10

<210> SEQ ID NO 22
<211> LENGTH: 17
<212> TYPE: PRT
<213> ORGANISM: Homo sapiens

<400> SEQUENCE: 22

Tyr Val Arg Pro Gly Gly Gly Phe Val Pro Asn Phe Gln Leu Phe Glu
1               5                   10                  15

Lys

<210> SEQ ID NO 23
<211> LENGTH: 13
<212> TYPE: PRT
<213> ORGANISM: Homo sapiens

<400> SEQUENCE: 23

Ala Gly Ala Leu Asn Ser Asn Asp Ala Phe Val Leu Lys
1               5                   10

<210> SEQ ID NO 24
<211> LENGTH: 17
<212> TYPE: PRT
<213> ORGANISM: Homo sapiens

<400> SEQUENCE: 24

Gln Thr Gln Val Ser Val Leu Pro Glu Gly Gly Glu Thr Pro Leu Phe
1               5                   10                  15

Lys

<210> SEQ ID NO 25
<211> LENGTH: 8
<212> TYPE: PRT
<213> ORGANISM: Homo sapiens

<400> SEQUENCE: 25

Thr Gly Ala Gln Glu Leu Leu Arg
1               5

<210> SEQ ID NO 26
<211> LENGTH: 11
<212> TYPE: PRT
<213> ORGANISM: Homo sapiens
```

<400> SEQUENCE: 26

Glu Ala Leu Val Pro Leu Val Ala Asp His Lys
1               5                   10

<210> SEQ ID NO 27
<211> LENGTH: 11
<212> TYPE: PRT
<213> ORGANISM: Homo sapiens

<400> SEQUENCE: 27

Val Ala Asn Tyr Val Asp Trp Ile Asn Asp Arg
1               5                   10

<210> SEQ ID NO 28
<211> LENGTH: 9
<212> TYPE: PRT
<213> ORGANISM: Homo sapiens

<400> SEQUENCE: 28

Asp Ser Val Thr Gly Thr Leu Pro Lys
1               5

<210> SEQ ID NO 29
<211> LENGTH: 9
<212> TYPE: PRT
<213> ORGANISM: Homo sapiens

<400> SEQUENCE: 29

Glu Ile Ile Ile His Gln Asn Tyr Lys
1               5

<210> SEQ ID NO 30
<211> LENGTH: 14
<212> TYPE: PRT
<213> ORGANISM: Homo sapiens

<400> SEQUENCE: 30

Ile Ala Tyr Gly Thr Gln Gly Ser Ser Gly Tyr Ser Leu Arg
1               5                   10

<210> SEQ ID NO 31
<211> LENGTH: 13
<212> TYPE: PRT
<213> ORGANISM: Homo sapiens

<400> SEQUENCE: 31

Ile Tyr Ser Gly Ile Leu Asn Leu Ser Asp Ile Thr Lys
1               5                   10

<210> SEQ ID NO 32
<211> LENGTH: 19
<212> TYPE: PRT
<213> ORGANISM: Homo sapiens

<400> SEQUENCE: 32

Asp Ile Pro Thr Asn Ser Pro Glu Leu Glu Glu Thr Leu Thr His Thr
1               5                   10                  15

Ile Thr Lys

<210> SEQ ID NO 33
<211> LENGTH: 11
<212> TYPE: PRT
<213> ORGANISM: Homo sapiens

<400> SEQUENCE: 33

Thr Val Gly Ser Asp Thr Phe Tyr Ser Phe Lys
1               5                   10

<210> SEQ ID NO 34
<211> LENGTH: 8
<212> TYPE: PRT
<213> ORGANISM: Homo sapiens

<400> SEQUENCE: 34

Phe Asn Ala Leu Gln Tyr Leu Arg
1               5

<210> SEQ ID NO 35
<211> LENGTH: 10
<212> TYPE: PRT
<213> ORGANISM: Homo sapiens

<400> SEQUENCE: 35

Ile Ser Asn Ile Pro Asp Glu Tyr Phe Lys
1               5                   10

<210> SEQ ID NO 36
<211> LENGTH: 10
<212> TYPE: PRT
<213> ORGANISM: Homo sapiens

<400> SEQUENCE: 36

Asn Asn Gln Ile Asp His Ile Asp Glu Lys
1               5                   10

<210> SEQ ID NO 37
<211> LENGTH: 14
<212> TYPE: PRT
<213> ORGANISM: Homo sapiens

<400> SEQUENCE: 37

Ala Gly Leu Leu Arg Pro Asp Tyr Ala Leu Leu Gly His Arg
1               5                   10

<210> SEQ ID NO 38
<211> LENGTH: 17
<212> TYPE: PRT
<213> ORGANISM: Homo sapiens

<400> SEQUENCE: 38

Pro Ser Leu Ser His Leu Leu Ser Gln Tyr Tyr Gly Ala Gly Val Ala
1               5                   10                  15

Arg

<210> SEQ ID NO 39
<211> LENGTH: 8
<212> TYPE: PRT
<213> ORGANISM: Homo sapiens

<400> SEQUENCE: 39

Thr Phe Thr Leu Leu Asp Pro Lys
1               5

<210> SEQ ID NO 40
<211> LENGTH: 13
<212> TYPE: PRT
<213> ORGANISM: Homo sapiens

<400> SEQUENCE: 40

Glu Glu Ser Leu Asp Ser Asp Leu Tyr Ala Glu Leu Arg
1               5                   10

<210> SEQ ID NO 41
<211> LENGTH: 10
<212> TYPE: PRT
<213> ORGANISM: Homo sapiens

<400> SEQUENCE: 41

Asn Ile Gln Ser Leu Glu Val Ile Gly Lys
1               5                   10

<210> SEQ ID NO 42
<211> LENGTH: 14
<212> TYPE: PRT
<213> ORGANISM: Homo sapiens

<400> SEQUENCE: 42

Ala Gln Leu Leu Gln Gly Leu Gly Phe Asn Leu Thr Glu Arg
1               5                   10

<210> SEQ ID NO 43
<211> LENGTH: 13
<212> TYPE: PRT
<213> ORGANISM: Homo sapiens

<400> SEQUENCE: 43

Glu Glu Asn Phe Tyr Val Asp Glu Thr Thr Val Val Lys
1               5                   10

<210> SEQ ID NO 44
<211> LENGTH: 9
<212> TYPE: PRT
<213> ORGANISM: Homo sapiens

<400> SEQUENCE: 44

Ser Val Asn Asp Leu Tyr Ile Gln Lys
1               5

<210> SEQ ID NO 45
<211> LENGTH: 9
<212> TYPE: PRT
<213> ORGANISM: Homo sapiens

<400> SEQUENCE: 45

Thr Leu Glu Ala Gln Leu Thr Pro Arg
1               5

<210> SEQ ID NO 46
<211> LENGTH: 13
<212> TYPE: PRT
<213> ORGANISM: Homo sapiens

<400> SEQUENCE: 46

Leu Gly Asn Gln Glu Pro Gly Gly Gln Thr Ala Leu Lys
1               5                   10

<210> SEQ ID NO 47
<211> LENGTH: 10
<212> TYPE: PRT
<213> ORGANISM: Homo sapiens

<400> SEQUENCE: 47

Phe Gln Pro Thr Leu Leu Thr Leu Pro Arg
1               5                   10

<210> SEQ ID NO 48
<211> LENGTH: 10
<212> TYPE: PRT
<213> ORGANISM: Homo sapiens

<400> SEQUENCE: 48

Leu Leu Asp Ser Leu Pro Ser Asp Thr Arg
1               5                   10

<210> SEQ ID NO 49
<211> LENGTH: 12
<212> TYPE: PRT
<213> ORGANISM: Homo sapiens

<400> SEQUENCE: 49

Leu Val Leu Leu Asn Ala Ile Tyr Leu Ser Ala Lys
1               5                   10

<210> SEQ ID NO 50
<211> LENGTH: 11
<212> TYPE: PRT
<213> ORGANISM: Homo sapiens

<400> SEQUENCE: 50

Thr Asn Leu Glu Ser Ile Leu Ser Tyr Pro Lys
1               5                   10

<210> SEQ ID NO 51
<211> LENGTH: 13
<212> TYPE: PRT
<213> ORGANISM: Homo sapiens

<400> SEQUENCE: 51

Ala Ala Asp Asp Thr Trp Glu Pro Phe Ala Ser Gly Lys
1               5                   10

<210> SEQ ID NO 52
<211> LENGTH: 13
<212> TYPE: PRT
<213> ORGANISM: Homo sapiens

<400> SEQUENCE: 52

Gly Ser Pro Ala Ile Asn Val Ala Val His Val Phe Arg
1               5                   10

<210> SEQ ID NO 53
<211> LENGTH: 15
<212> TYPE: PRT
<213> ORGANISM: Artificial Sequence
<220> FEATURE:
<223> OTHER INFORMATION: start amino acid sequence of the PPBP precursor
<220> FEATURE:
<221> NAME/KEY: MISC_FEATURE
<222> LOCATION: (2)..(9)
<223> OTHER INFORMATION: X is any amion acid.

<400> SEQUENCE: 53

Ser Xaa Xaa Xaa Xaa Xaa Xaa Xaa Xaa Asn Leu Ala Lys Gly Lys
1               5                   10                  15

<210> SEQ ID NO 54
<211> LENGTH: 8
<212> TYPE: PRT
<213> ORGANISM: Artificial Sequence
<220> FEATURE:
<223> OTHER INFORMATION: end amino acid sequence of the PPBP precursor

```
<400> SEQUENCE: 54

Leu Ala Gly Asp Glu Ser Ala Asp
1               5
```